(12) United States Patent
Trezza, II et al.

(10) Patent No.: US 11,872,584 B2
(45) Date of Patent: *Jan. 16, 2024

(54) SPRAY DEVICES INCLUDING SIDE-BY-SIDE SPRAY TIPS HAVING FLUID PATHWAYS WITH SWIRL CHAMBERS FOR DISPENSING TWO FLUIDS THAT CHEMICALLY REACT TOGETHER

(71) Applicant: Ethicon, Inc., Somerville, NJ (US)

(72) Inventors: Michael J. Trezza, II, Long Valley, NJ (US); Salim A. Ghodbane, Piscataway, NJ (US); Simon Cohn, Lebanon, NJ (US)

(73) Assignee: Ethicon, Inc., Somerville, NJ (US)

( * ) Notice: Subject to any disclaimer, the term of this patent is extended or adjusted under 35 U.S.C. 154(b) by 8 days.

This patent is subject to a terminal disclaimer.

(21) Appl. No.: 17/667,710

(22) Filed: Feb. 9, 2022

(65) Prior Publication Data

US 2022/0266276 A1   Aug. 25, 2022

Related U.S. Application Data

(62) Division of application No. 16/593,799, filed on Oct. 4, 2019, now Pat. No. 11,358,165.

(51) Int. Cl.
  *B05B 7/08* (2006.01)
  *B05B 7/10* (2006.01)
(52) U.S. Cl.
  CPC .............. *B05B 7/0846* (2013.01); *B05B 7/10* (2013.01)
(58) Field of Classification Search
  CPC .................................. B05B 7/0846; B05B 7/10

USPC .................. 239/404, 420, 426, 433, 434
See application file for complete search history.

(56) References Cited

U.S. PATENT DOCUMENTS

| | | |
|---|---|---|
| 5,152,460 A | 10/1992 | Barty |
| 5,368,563 A | 11/1994 | Lonneman et al. |
| 5,526,981 A | 6/1996 | Sanson |
| 5,759,169 A | 6/1998 | Marx |
| 6,432,084 B1 | 8/2002 | Evinson et al. |
| 6,547,161 B1 | 4/2003 | Huang |

(Continued)

OTHER PUBLICATIONS

"FibriJet Biomaterial Delivery Devices," Nordson Medical, St. Paul, MN, https://www.nordsonmedical.com/Components-and-Technologies/Biomaterial-Delivery-Devices/FibriJet-Delivery-Devices/, Jul. 25, 2018, 32 pages.

(Continued)

*Primary Examiner* — Christopher S Kim
(74) *Attorney, Agent, or Firm* — Troutman Pepper Hamilton Sanders LLP

(57) ABSTRACT

A spray device includes side-by-side spray tips that are spaced from one another at a distal end of the spray device. A first spray tip has a first fluid pathway defining a first flow area. The first fluid pathway has a first swirl chamber having an outer perimeter and flutes having inner ends that direct a first fluid into the outer perimeter of the first swirl chamber for rotating the first fluid in a circular pattern. A second spray tip has a second fluid pathway that defines a second flow area that is larger than the first flow area. The second fluid pathway has a second swirl chamber having an outer perimeter and flutes having inner ends that direct a second fluid into the outer perimeter of the second swirl chamber for rotating the second fluid in a circular pattern.

20 Claims, 33 Drawing Sheets

(56) References Cited

U.S. PATENT DOCUMENTS

| | | |
|---|---|---|
| 6,612,506 B1 | 9/2003 | Huang |
| 7,163,160 B2 | 1/2007 | Liu |
| 7,694,944 B2 | 4/2010 | Gottlieb et al. |
| 8,408,480 B2 | 4/2013 | Hull et al. |
| 11,358,165 B2 * | 6/2022 | Trezza, II ................. B05B 7/10 |
| 2003/0069537 A1 | 4/2003 | Spero et al. |
| 2006/0253082 A1 | 11/2006 | McIntosh et al. |
| 2009/0108091 A1 | 4/2009 | Steffan |
| 2013/0325059 A1 | 12/2013 | O'Neill |
| 2016/0067423 A1 | 3/2016 | Goodman et al. |
| 2016/0354803 A1 | 12/2016 | Smith |
| 2018/0177978 A1 | 6/2018 | Spivey et al. |
| 2019/0029660 A1 | 1/2019 | Hull et al. |

OTHER PUBLICATIONS

"Rely on EVICEL Fibrin Sealant," Ethicon US, LLC, 2015, 6 pages.
Blasterparts: "NERF—Super Soaker FlashFlood," www.blasterparts. com/en/p/nerf-super-soaker-flashflood--560280, Jul. 13, 2019, pp. 1-6.
Tamer, et al., "Fibrin: A Versatile Scaffold for Tissue Engineering Applications," Tissue Engineering Part B—Reviews, Jun. 1, 2008, p. 203, Figure 3, vol. 14, No. 2, Publisher—Mary Ann Liebert, Inc., US.
International Search Report issued in corresponding International Application No. PCT/IB2020/059183, dated Apr. 6, 2021, 8 pages.

* cited by examiner

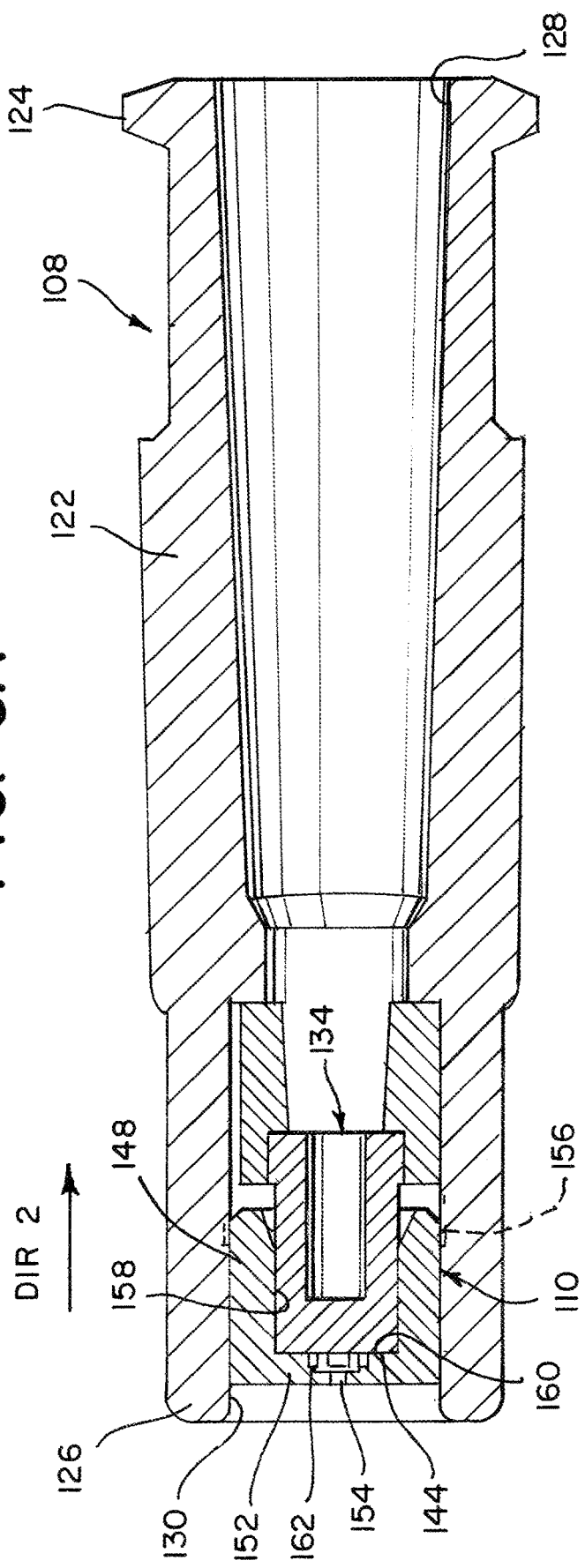

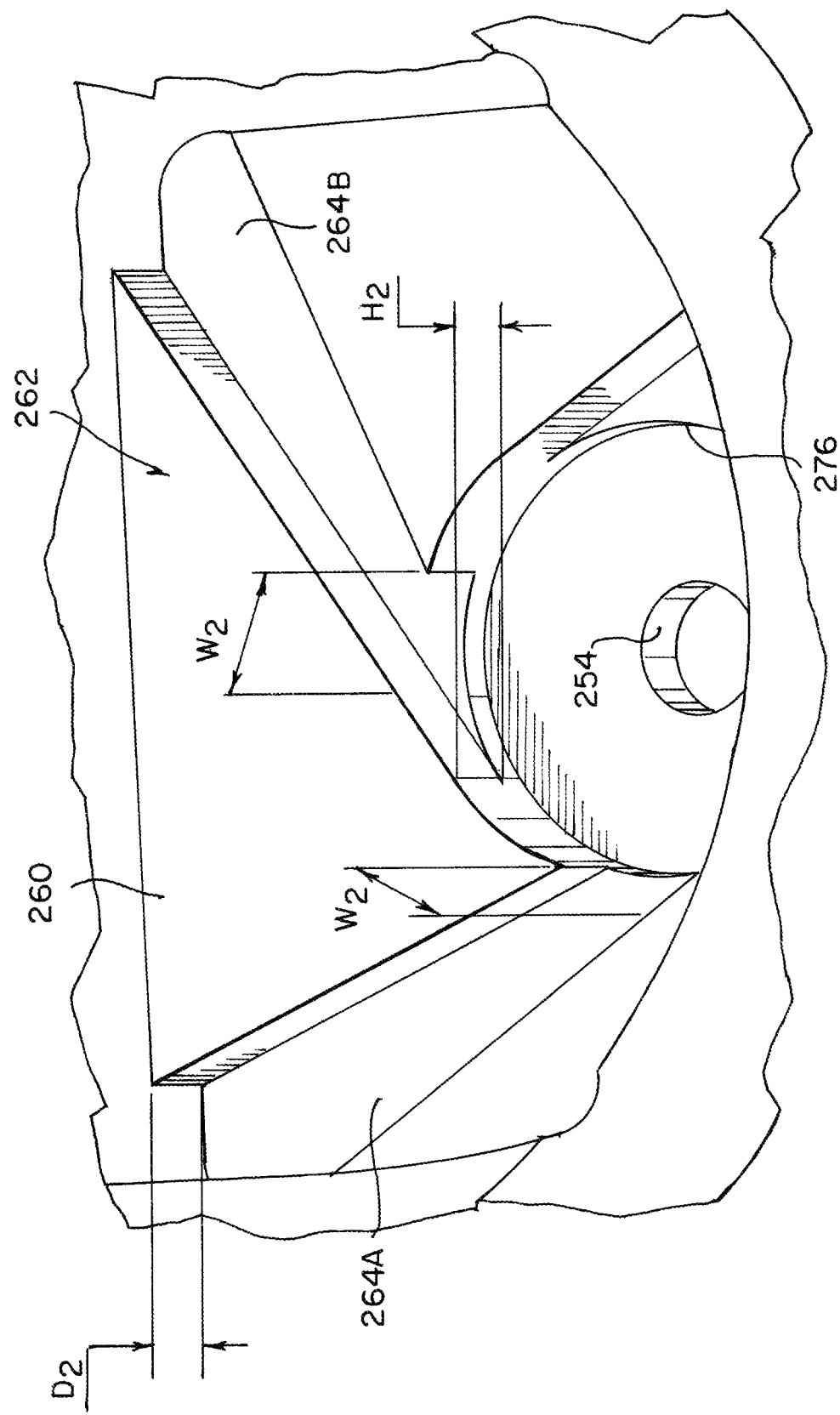

SPRAY DEVICES INCLUDING SIDE-BY-SIDE SPRAY TIPS HAVING FLUID PATHWAYS WITH SWIRL CHAMBERS FOR DISPENSING TWO FLUIDS THAT CHEMICALLY REACT TOGETHER

CROSS-REFERENCE TO RELATED APPLICATIONS

The present patent application is a divisional application of U.S. patent application Ser. No. 16/593,799, filed on Oct. 4, 2019, now allowed, the disclosure of which is hereby incorporated by reference herein.

BACKGROUND OF THE INVENTION

Field of the Invention

The present patent application is generally related to medical devices for dispensing fluids, and is more specifically related to spray devices having spray tips that dispense fluids that react together for use in medical and surgical procedures.

Description of the Related Art

Recently, minimally invasive surgery (MIS) techniques have emerged as an alternative to conventional surgical techniques for performing a wide range of surgical procedures. MIS procedures differ from conventional surgical procedures in that a plurality of devices and/or surgical tools may be introduced into the body through cannulas and/or trocars that are inserted into small incisions made in the body. As a result of using MIS techniques, trauma to the body is greatly reduced, which decreases recovery time for patients.

One type of minimally invasive surgery involves laparoscopic surgical procedures, which are used to treat hernias, colon dysfunctions, gastroesophageal reflux disease, gallbladder disorders, etc. Typically, a patient undergoing a laparoscopic surgical procedure is able to return home within hours after undergoing surgery.

One challenge presented when performing MIS procedures relates to controlling bleeding at the surgical site. In contrast to conventional open surgical procedures, during a laparoscopic procedure a surgeon's access to a surgical site or surgical cavity is greatly reduced.

In response, tissue sealants and other biological adhesive materials have been developed for use in closing incisions at surgical sites. Tissue sealants may include fibrin sealants, which is composed of thrombin, and a fibrinogen material, although other formulations are also available. Typically, the individual components of the tissue sealants (e.g., thrombin and fibrinogen) are stored separately in isolated reservoirs because the components will rapidly react once they come in contact with one another. In many instances, the two separate components are mixed together for the first time immediately prior to being applied to tissue.

Medical devices for spraying fluids are disclosed in U.S. Pat. Nos. 5,152,460, 5,526,981, 6,432,084, 6,547,161, 6,612,506, 7,163,160, 7,694,944, and U.S. Patent Application Publication No. 2009/0108091.

Once mixed, the components coagulate very quickly, yielding an adhesive gel within a short period of time (e.g., within 10-20 seconds). When applied to the exterior of the body, or when access to the application site is possible, the rapid coagulative properties of the tissue sealant are advantageous. However, the fast-acting properties of tissue sealants often clog the spray tips that are used for dispensing the components.

Commercially available spray tips that are used to atomize tissue sealants typically operate by mixing the components of the tissue sealant inside the spray tip and prior to spraying. Due to the quick acting nature of the biologics, the spray tips typically clog as soon as the flow of fluid through the spray tip stops (e.g., typically within one to two seconds). Once the spray tips become clogged, they can no longer be used to atomize biologics and must be replaced with new spray tips.

Surgeons would prefer to have the ability to spray, evaluate the results of the spray (has hemostasis occurred), and then continue spraying without the need changing spray tips. This need is particularly valuable in minimally invasive/robotic surgery where removing the device to change the spray tip and reposition the device for spraying is a more time-consuming procedure.

For example, FIG. 1 shows a prior art spray device 50 used to spray two fluids that react together. The spray device 50 has a manifold 52 with a first lumen 54 adapted to receive a first fluid and a second lumen 56 adapted to receive a second fluid that is mixed with the first fluid prior to the two fluids being sprayed from the device. The manifold 52 has fluid conduits that join together the first and second fluids that flow into the first and second lumens 54, 56 for combining and mixing the first and second fluids together at the spray tip 58. The spray device 50 includes a spray tip having a spray orifice 60 that sprays the two fluids after they have been mixed together. The mixed together first and second fluids are sprayed from the spray orifice 60 located at the distal end of the spray tip 58. The mixing of the first and second fluids, which typically occurs at the distal end of the spray tip 58, often leads to almost instant clogging of the spray tip 58 when spraying is stopped. Thus, the spray device may be used to spray one time only, and then the spray tip 58 must be replaced with a new spray tip to continue spraying the first and second fluids.

FIG. 2 shows a second prior art spray device 70 used to spray two fluids that react together. The spray device 70 includes a manifold 72 that brings together a first fluid flowing through a first lumen 74 and a second fluid flowing through a second lumen 76. The manifold 72 directs the first and second fluids downstream for spraying the first fluid from a first spray orifice 80A and the second fluid from a second spray orifice 80B. After spraying, the first and second fluids tend to puddle over a distal end face 82 of the manifold 72, which clogs the first and second spray orifices 80A, 80B. The spray orifices must be unclogged, or the entire manifold 72 replaced with a new manifold to continue spraying the first and second fluids.

In view of the above-noted deficiencies, there is a continuing need for fluid dispensing devices having spray tips that provide surgeons with the ability to spray biologics and quick-acting tissue sealants, evaluate the results of the spray (e.g., has hemostasis occurred?), and then continue spraying without the need for changing the spray tips. Satisfying this need is particularly valuable in minimally invasive/robotic surgery where removing the device from a cannula or from inside a patient in order to change a spray tip and/or reposition a device for spraying is a more time-consuming procedure.

Moreover, there is a need for improved anti-clogging spray tips for dispensing tissue sealants onto tissue. In addition, there is a need for medical devices for spraying two components that react together rapidly and in close proximity to a target surface.

There is also a need for fluid dispensing devices capable of effectively delivering a multiple component tissue sealant to a location in vivo from a remote location, whereby the devices may be easily, efficiently, and uniformly mass-produced. In addition, there is a need for fluid dispensing devices capable of effectively delivering a multiple component tissue sealant that may be used during open surgical procedures.

SUMMARY OF THE INVENTION

Atomization of a fluid results from differences in velocity between the fluid and the air. Using similarly constructed spray devices, it is easier to atomize a lower viscosity fluid than a higher viscosity fluid. For example, it is easier to atomize a lower viscosity fluid, Thrombin, because it comprises a low viscosity fluid. In contrast, a higher viscosity fluid, Fibrinogen, is significantly more viscous than Thrombin, which makes atomization of Fibrinogen more difficult. Thus, if an identical spray device is used to first atomize Thrombin and then later atomize Fibrinogen, the lower viscosity Thrombin spray would have a broader spray pattern with finer liquid particles, while the higher viscosity Fibrinogen spray would have a narrower spray pattern with larger liquid particles, or the higher viscosity fluid would form a stream of fluid rather than an atomized spray.

To date, prior art designs for spray devices have focused on minimizing the lengths of fluid pathways to increase the flow rate or velocity of fluids. In one embodiment, the spray device disclosed herein provides an improved, novel way for atomizing higher viscosity fluids, such as Fibrinogen. In one embodiment, a spray device changes the fluid pathway, and more specifically the flow area of fluid pathways that are provided on orifice cups having spray openings.

In one embodiment, a spray device effectively sprays fluids having higher viscosities by increasing the flow rate of the higher viscosity fluid before it is dispensed from a spray tip. This method relies on a principle of fluid dynamics, which dictates that an incompressible fluid's velocity will increase as it passes through a constriction. In other words, if the fluid pathway for a fluid narrows in cross-sectional area, the flow rate or velocity of the fluid will increase as it passes through the narrower section of the fluid pathway.

Thus, in one embodiment, a more viscous fluid, such as Fibrinogen, is passed through a spray tip having a first fluid pathway with a smaller flow area to speed up the flow rate of the more viscous fluid in a swirl chamber to make the more viscous fluid atomize to an acceptable level. In contrast, a less viscous fluid, such as Thrombin, may be passed through a spray tip having a second fluid pathway with a larger flow area because less energy is required to atomize the less viscous fluid to an acceptable level.

In one embodiment, a spray device having side-by-side spray tips preferably includes a first spray tip including a first fluid pathway that defines a first flow area, and a second spray tip adjacent the first spray tip, the second spray tip including a second fluid pathway that defines a second flow area that is larger than the first flow area of the first spray tip. The first and second spray tips are preferably side-by-side and spaced from one another at a distal end of the spray device.

In one embodiment, when a first fluid (e.g., Fibrinogen) having a volumetric flow rate is introduced into the first spray tip and a second fluid (e.g., Thrombin) having the same volumetric flow rate as the first fluid is introduced into the second spray tip, the first fluid will flow through the first fluid pathway of the first spray tip at a greater velocity than the second fluid will flow through the second fluid pathway of the second spray tip.

In one embodiment, the first spray tip may include a first spray housing and a first orifice cup assembled with a distal end of the first spray housing. In one embodiment, the first orifice cup has a distal end wall with an inner face having the first fluid pathway formed therein.

In one embodiment, the second spray tip preferably includes a second spray housing and a second orifice cup assembled with a distal end of the second spray housing. In one embodiment, the second orifice cup has a distal end wall with an inner face having the second fluid pathway formed therein.

In one embodiment, the first fluid pathway formed in the inner face of the distal end wall of the first orifice cup desirably includes a first swirl chamber having an outer perimeter and flutes having inner ends that direct the first fluid into the outer perimeter of the first swirl chamber for rotating the first fluid in a circular pattern within the first swirl chamber.

In one embodiment, the second fluid pathway formed in the inner face of said distal end wall of the second orifice cup preferably includes a second swirl chamber having an outer perimeter and flutes having inner ends that direct the second fluid into the outer perimeter of the second swirl chamber for rotating the second fluid in a circular pattern within the second swirl chamber.

In one embodiment, the inner ends of the flutes that direct the first fluid into the outer perimeter of the first swirl chamber define a first cross-sectional area and the inner ends of the flutes that direct the second fluid into the outer perimeter of the second swirl chamber define a second cross-sectional area that is different than the first cross-sectional area.

In one embodiment, the second cross-sectional area of the flutes of the second fluid pathway is at least twice as large as the first cross-sectional area of the flutes of the first fluid pathway.

In one embodiment, the second cross-sectional area of the flutes of the second fluid pathway is at least four times as large as the first cross-sectional area of the flutes of the first fluid pathway.

In one embodiment, the first swirl chamber has a first diameter and said second swirl chamber has a second diameter that is the same as the first diameter of the first swirl chamber.

In one embodiment, the first orifice cup may include a cylindrical outer wall having a proximal end with a proximal opening and a distal end that is closed by the distal end wall, and a first spray opening that passes through the distal end wall and that is in fluid communication with the first swirl chamber.

In one embodiment, the first spray housing may include a first tubular body having a proximal end with a proximal opening, a distal end with a distal opening and an elongated conduit extending from the proximal opening to the distal opening of the first tubular body.

In one embodiment, the first spray housing may include a first cylindrical insert disposed within the elongated conduit and located at the distal end of the first tubular body. In one embodiment, the first cylindrical insert preferably has a distal end wall at the distal end thereof. In one embodiment, the first orifice cup is assembled with the first cylindrical insert so that the distal end of the first cylindrical insert is disposed inside the cylindrical outer wall of the first orifice cup with the inner face of the distal end wall of the first orifice cup in contact with an outer surface of the distal end wall of the first cylindrical insert.

In one embodiment, when the first orifice cup is assembled with the first cylindrical insert of the first spray housing, the first swirl chamber and the flutes of the first orifice cup are disposed between the outer surface of the distal end wall of the first cylindrical insert and the distal end wall of the first orifice cup.

In one embodiment, the flutes of the first orifice cup preferably include a first flute having an outer end adjacent the cylindrical outer wall of the first orifice cup and an inner end located at the outer periphery of the first swirl chamber, and a second flute having an outer end adjacent the cylindrical outer wall of the first orifice cup and an inner end located at the outer periphery of the first swirl chamber. In one embodiment, the first and second flutes preferably direct the first fluid into the outer perimeter of the first swirl chamber for rotating the first fluid within the first swirl chamber in a circular pattern.

In one embodiment, the second orifice cup may include a cylindrical outer wall having a proximal end with a proximal opening and a distal end that is closed by the distal end wall, and a second spray opening that passes through the distal end wall and that is in fluid communication with the second swirl chamber.

In one embodiment, the second spray housing may include a second tubular body having a proximal end with a proximal opening, a distal end with a distal opening, and an elongated conduit extending from the proximal opening to the distal opening of the second tubular body.

In one embodiment, the second spray housing preferably includes a second cylindrical insert disposed within the elongated conduit and located at the distal end of the second tubular body. In one embodiment, the second cylindrical insert desirably includes a distal end wall at the distal end thereof. In one embodiment, the second orifice cup is assembled with the second cylindrical insert so that the distal end of the second cylindrical insert is disposed inside the cylindrical outer wall of the second orifice cup with the inner face of the distal end wall of the second orifice cup in contact with an outer surface of the distal end wall of the second cylindrical insert.

In one embodiment, when the second orifice cup is assembled with the second cylindrical insert, the second swirl chamber and the flutes of the second orifice cup are disposed between the outer surface of the distal end wall of the second cylindrical insert and the distal end wall of the second orifice cup.

In one embodiment, the flutes of the second orifice cup may include a first flute having an outer end adjacent the cylindrical outer wall of the second orifice cup and an inner end located at the outer periphery of the second swirl chamber, a second flute having an outer end adjacent the cylindrical outer wall of the second orifice cup and an inner end located at the outer periphery of the second swirl chamber, a third flute having an outer end adjacent the cylindrical outer wall of the second orifice cup and an inner end located at the outer periphery of the second swirl chamber, and a fourth flute having an outer end adjacent the cylindrical outer wall of the second orifice cup and an inner end located at the outer periphery of the second swirl chamber.

In one embodiment, the first, second, third and fourth flutes of the second orifice cup desirably direct the second fluid into the outer perimeter of the second swirl chamber for rotating the second fluid within the second swirl chamber in a circular pattern.

In one embodiment, a spray device having side-by-side spray tips preferably includes a first syringe containing a higher viscosity fluid (e.g., Fibrinogen) and a second syringe containing a lower viscosity fluid (e.g., Thrombin) that reacts with the higher viscosity fluid.

In one embodiment, the spray device preferably has a first spray tip for spraying the higher viscosity fluid. In one embodiment, the first spray tip is in fluid communication with the first syringe and includes a first fluid pathway that defines a first flow area.

In one embodiment, the spray device preferably has a second spray tip for spraying the lower viscosity fluid. In one embodiment, the second spray tip is in fluid communication with the second syringe and includes a second fluid pathway that defines a second flow area that is larger than the first flow area of the first spray tip.

In one embodiment, the first and second spray tips of the spray device are desirably side-by-side and spaced from one another at a distal end of the spray device.

In one embodiment, when a volume of the higher viscosity fluid is directed into the first spray tip at a flow rate and the lower viscosity fluid is directed into the second spray tip at the same volume and flow rate that are used for the higher viscosity fluid, the higher viscosity fluid will preferably flow through the first fluid pathway of the first spray tip at a greater flow rate than the lower viscosity fluid will flow through the second fluid pathway of the second spray tip.

In one embodiment, the higher viscosity fluid, Fibrinogen, and the lower viscosity fluid, Thrombin, chemically react with one another after being sprayed from distal ends of the respective first and second spray tips for forming a sealant on a surface, such as a tissue sealant.

In one embodiment, the spray device may include a first one-way check valve disposed between a distal end of the first syringe and a proximal end of the first spray tip for allowing the higher viscosity fluid to flow in only one direction toward the distal end of the spray device.

In one embodiment, the spray device may include a second one-way check valve disposed between a distal end of the second syringe and a proximal end of the second spray tip for allowing the lower viscosity fluid to flow in only one direction toward the distal end of the spray device.

In one embodiment, the spray device may include a first pressure control valve disposed between the distal end of the first syringe and the proximal end of the first spray tip. In one embodiment, the first pressure control valve opens when the higher viscosity fluid reaches a first predetermined pressure level.

In one embodiment, the spray device may include a second pressure control valve disposed between the distal end of the second syringe and the proximal end of the second spray tip. In one embodiment, the second pressure control valve opens when the lower viscosity fluid reaches a second predetermined pressure level.

In one embodiment, a spray device may include two pressure control valves that are coupled together such that they actuate at the same time for directing a first fluid into a first fluid path and a second fluid into a second fluid path.

In one embodiment, a spray device having first and second spray tips that are side-by-side and spaced from one another at a distal end of the spray device desirably includes a first spray tip including a first spray housing and a first orifice cup assembled with a distal end of the first spray housing, whereby the first orifice cup has a distal end wall with an inner face having a first fluid pathway formed therein that defines a first flow area, and a second spray tip including a second spray housing and a second orifice cup assembled with a distal end of the second spray housing, whereby the second orifice cup has a distal end wall with an inner face having a second fluid pathway formed therein that defines a second flow area that is larger than the first flow area of the first orifice cup.

In one embodiment, a first syringe containing a higher viscosity fluid is in fluid communication with the first spray tip, and a second syringe containing a lower viscosity fluid is in fluid communication with the second spray tip. The higher and lower viscosity fluids are adapted to chemically react with one another after being sprayed from distal ends of the respective first and second spray tips.

In one embodiment, the plungers of the syringes are physically coupled together such that the syringes express the same volumetric flow rate.

In one embodiment, when a higher viscosity fluid is directed into the first spray tip at a volumetric flow rate and the lower viscosity fluid is directed into the second spray tip at the same volumetric flow rate that is used for the higher viscosity fluid, the higher viscosity fluid will flow through the first fluid pathway of the first orifice cup at a greater velocity than the lower viscosity fluid will flow through the second fluid pathway of the second orifice cup.

In one embodiment, the first fluid pathway formed in the inner face of the distal end wall of the first orifice cup desirably includes a first swirl chamber having an outer perimeter and flutes having inner ends that direct the higher viscosity fluid into the outer perimeter of the first swirl chamber for rotating the higher viscosity fluid in a circular pattern within the first swirl chamber.

In one embodiment, the second fluid pathway formed in the inner face of the distal end wall of the second orifice cup desirably includes a second swirl chamber having an outer perimeter and flutes having inner ends that direct the lower viscosity fluid into the outer perimeter of the second swirl chamber for rotating the lower viscosity fluid in a circular pattern within the second swirl chamber.

These and other preferred embodiments of the present invention will be described in more detail below.

BRIEF DESCRIPTION OF THE DRAWINGS

FIG. 8E-1 is a magnified view of the first swirl chamber of the first orifice cup shown in FIG. 8E.

FIG. 9A is a cross-sectional view of the first orifice cup shown in FIGS. 8A-8I assembled with the distal end of the first spray housing shown in FIGS. 4A-4C, in accordance with one embodiment of the present patent application.

FIG. 10E-1 is a magnified view of the second swirl chamber of the second orifice cup shown in FIG. 10E.

FIG. 10H is still another perspective view of the proximal end of the second orifice cup shown in FIGS. 10F and 10G.

FIG. 10I is a cross-sectional view of the second orifice cup shown in FIGS. 10A-10H.

DETAILED DESCRIPTION OF PREFERRED EMBODIMENTS

Figure 3:
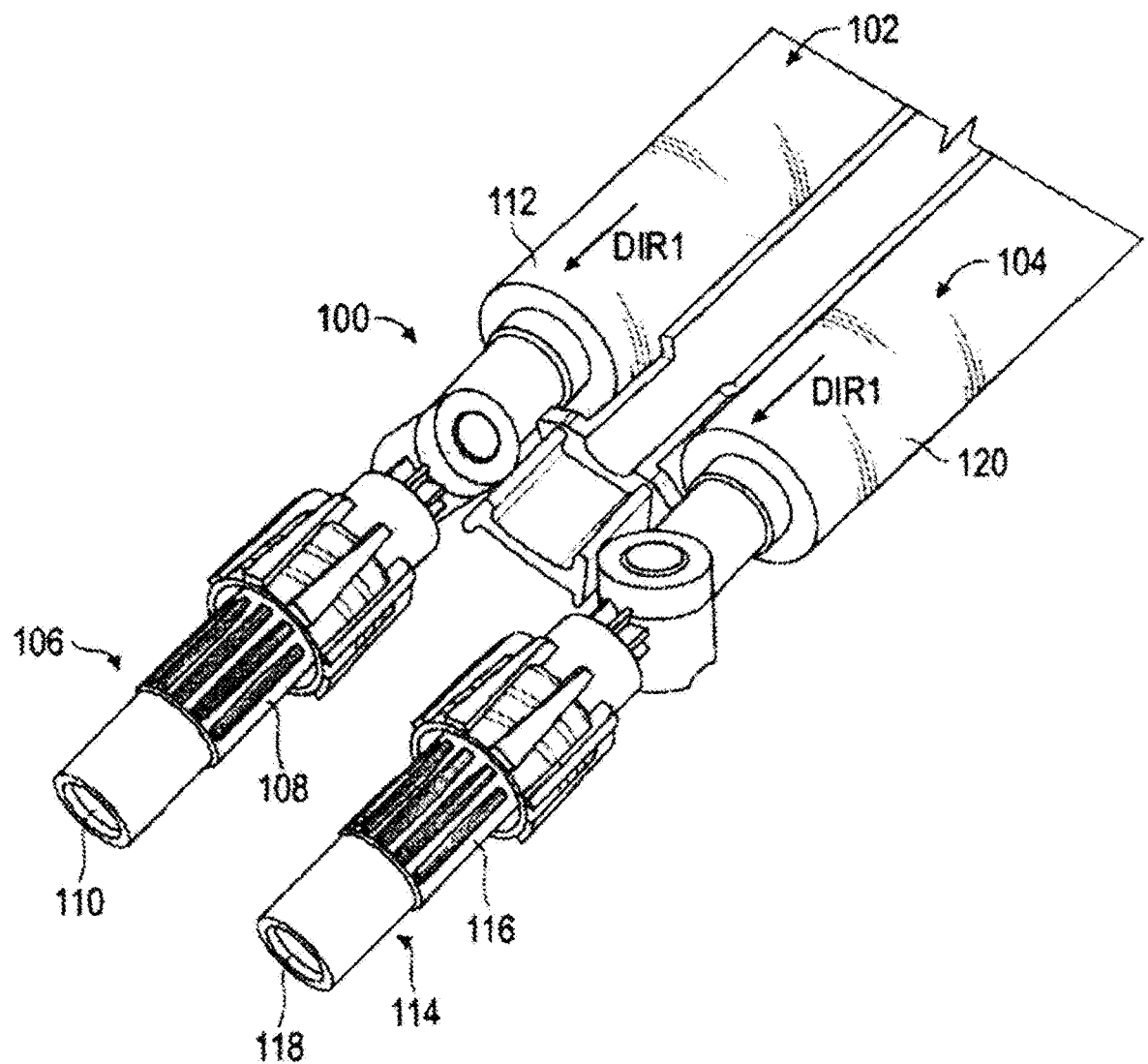
FIG. 3 is a perspective view of a spray device used for spraying two fluids that react together including a first spray housing containing a first orifice cup and second spray housing containing a second orifice cup, in accordance with one embodiment of the present patent application.

Referring to FIG. 3, in one embodiment, a spray device 100 for spraying first and second fluids that react together preferably includes a first flow path 102 for a first fluid (e.g., a higher viscosity fluid such as Fibrinogen) and a second flow path 104 for a second fluid (e.g., a lower viscosity fluid such as Thrombin). In one embodiment, the spray device 100 preferably includes a first spray tip 106 having a first spray housing 108 and a first orifice cup 110 assembled with the distal end of the first spray housing 108. The first spray tip 106 is preferably located downstream from a first syringe 112 that contains the first fluid (e.g., Thrombin). In one embodiment, the spray device 100 desirably includes a second spray tip 114 having a second spray housing 116 and a second orifice cup 118 assembled with the distal end of the second spray housing 116. The second spray tip 114 is preferably located downstream from and in fluid communication with a second syringe 120 that desirably contains a second fluid (e.g., Fibrin).

In one embodiment, each of the first and second syringes 112, 120 may include plungers for forcing the first and second fluids toward the first and second spray tips. The plungers may be depressed in the distal direction designed DIR1 toward the distal ends of the respective first and second syringes 112, 120 for spraying the first and second fluids from the distal ends of the respective first and second spray tips 106, 114. After being sprayed from the two spray tips, the first and second fluids preferably mix and/or chemically react with one another. In one embodiment, the first and second fluids may be the components of a tissue sealant (e.g., Fibrinogen and Thrombin), whereby the two fluids are sprayed onto a surface and then chemically react with one another on the surface to function as a tissue sealant.

Figure 4A:
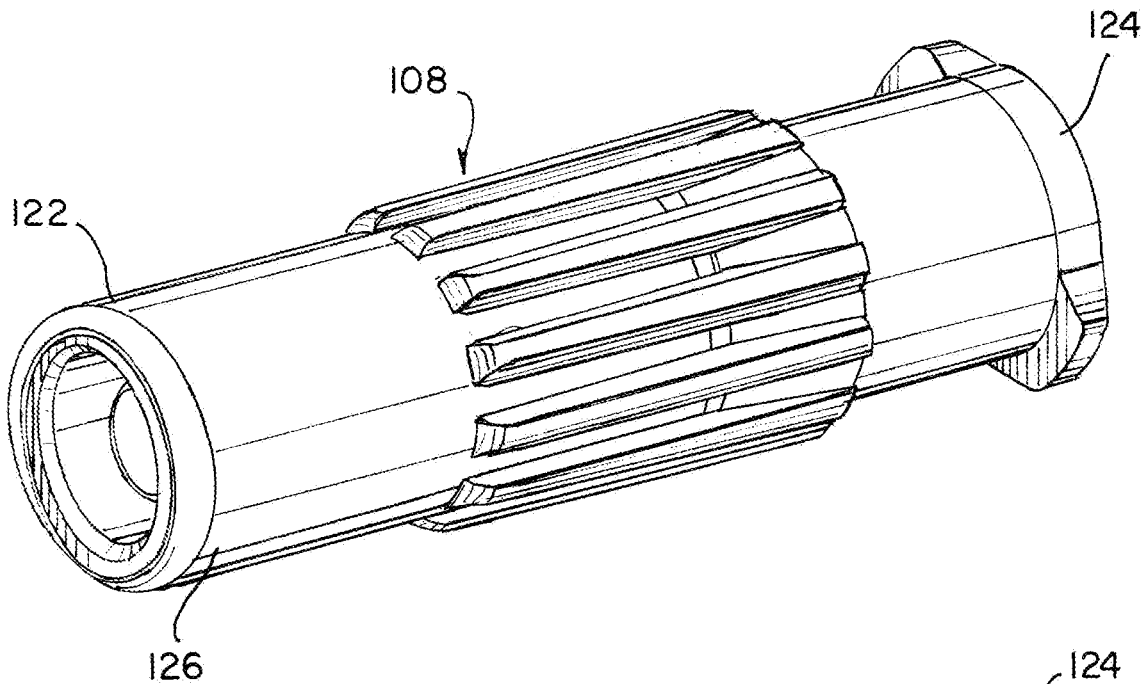
FIG. 4A is a perspective view of the first spray housing shown in FIG. 3, in accordance with one embodiment of the present patent application.
Figure 4B:
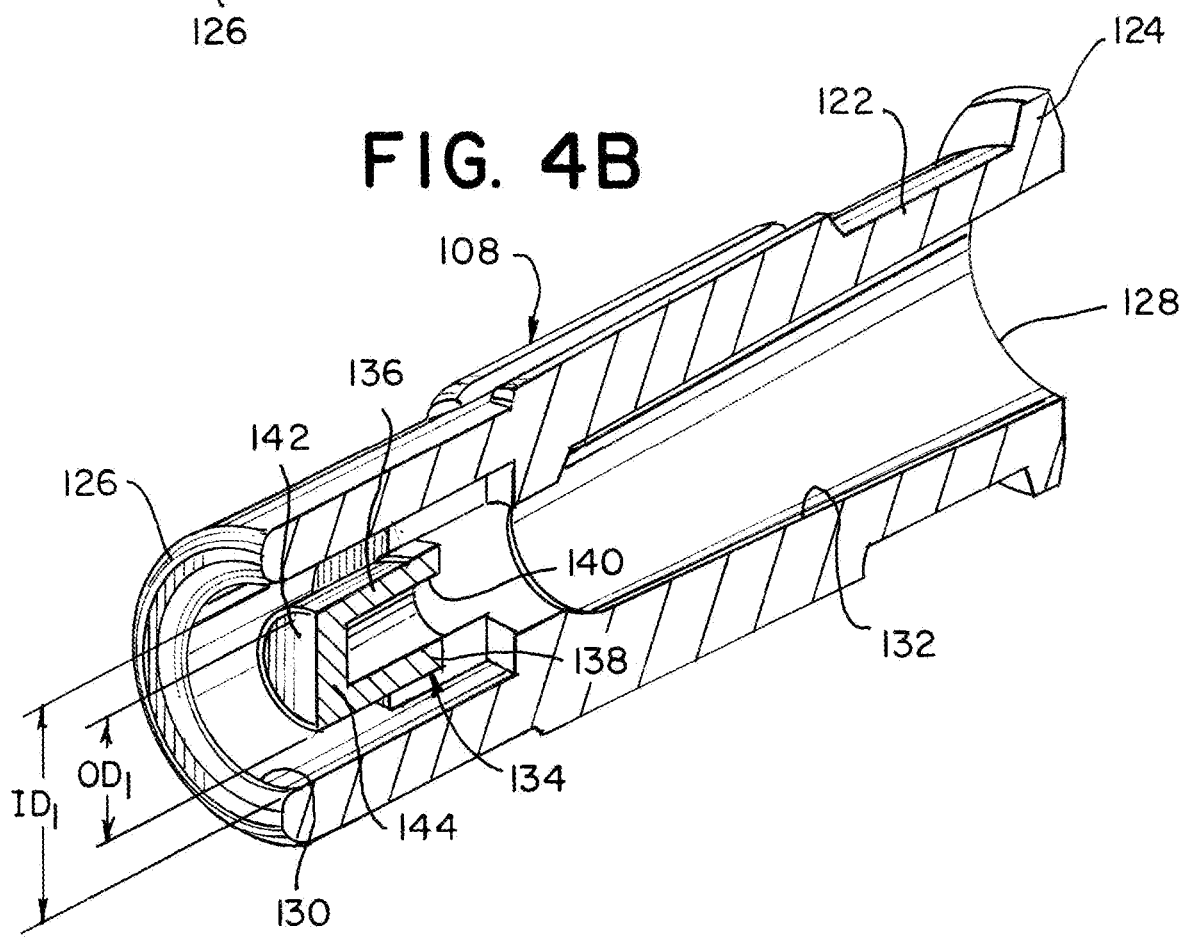
FIG. 4B is a cross-sectional view of the first spray housing shown in FIG. 4A.

Referring to FIGS. 4A and 4B, in one embodiment, the first spray housing 108 preferably includes a hollow tube 122 having a proximal end 124 and a distal end 126. The hollow tube 122 may have a cylindrical shape. The first spray housing 108 desirably includes a proximal opening 128 located at the proximal end 124 of the hollow tube 122 and a distal opening 130 located at the distal end 126 of the hollow tube 122. The first spray housing 108 desirably includes a first elongated conduit 132 that extends along the length of the hollow tube 122 between the proximal opening 128 and the distal opening 130.

Figure 4C:
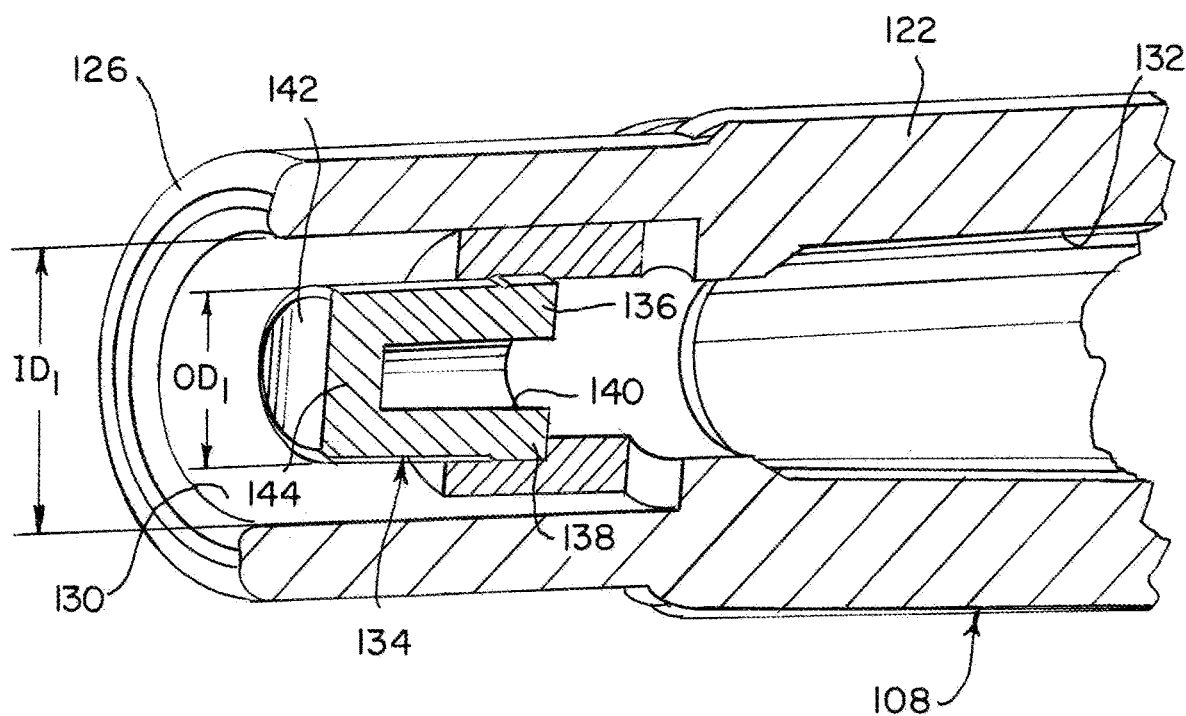
FIG. 4C is a magnified cross-sectional view of the distal end of the first spray housing shown in FIG. 4B.

Referring to FIGS. 4B and 4C, in one embodiment, the first spray housing 108 desirably includes an insert 134 that is located within the elongated conduit 132 and that is preferably positioned adjacent the distal end 126 of the hollow tube 122. In one embodiment, the insert 134 preferably includes a cylindrical wall 136 having a proximal end 138 defining a proximal opening 140 and a distal end 142 having a distal end wall 144. The distal end 142 of the cylindrical wall 136 of the insert 134 preferably defines an outer diameter $OD_1$. The distal opening 130 of the hollow tube 122 defines an inner diameter $ID_1$, which is desirably larger than the outer diameter $OD_1$ of the distal end 142 of the cylindrical wall 136 of the insert 134. As will be described in more detail herein, in one embodiment, the first orifice cup 110 (FIG. 3) may be inserted into the distal opening 130 of the hollow tube 122 of the first spray housing 108 and pressed against the distal end wall 144 of the insert 134 for assembling the first orifice cup 110 (FIG. 3) with the distal end 126 of the hollow tube 122 of the first spray housing 108.

Figure 5:
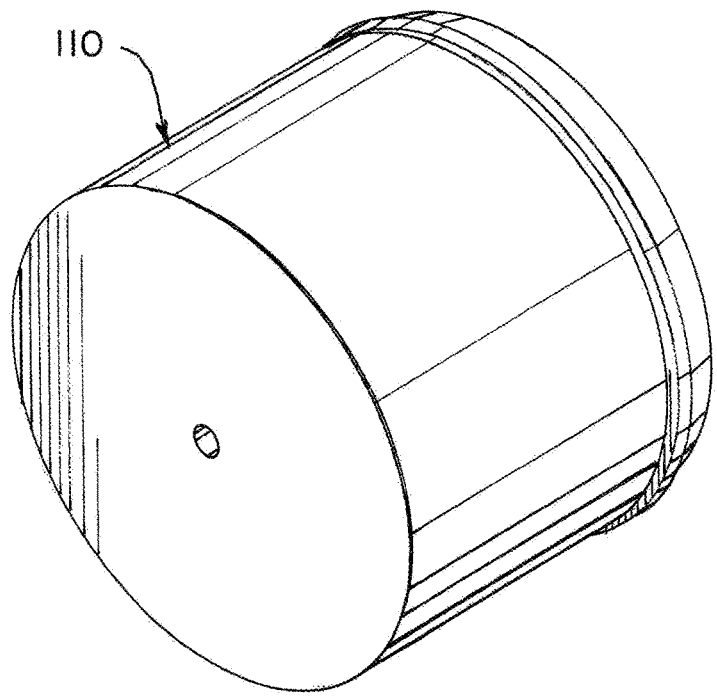
FIG. 5 is a perspective view of the first orifice cup shown in FIG. 3, in accordance with one embodiment of the present patent application.
Figure 6:
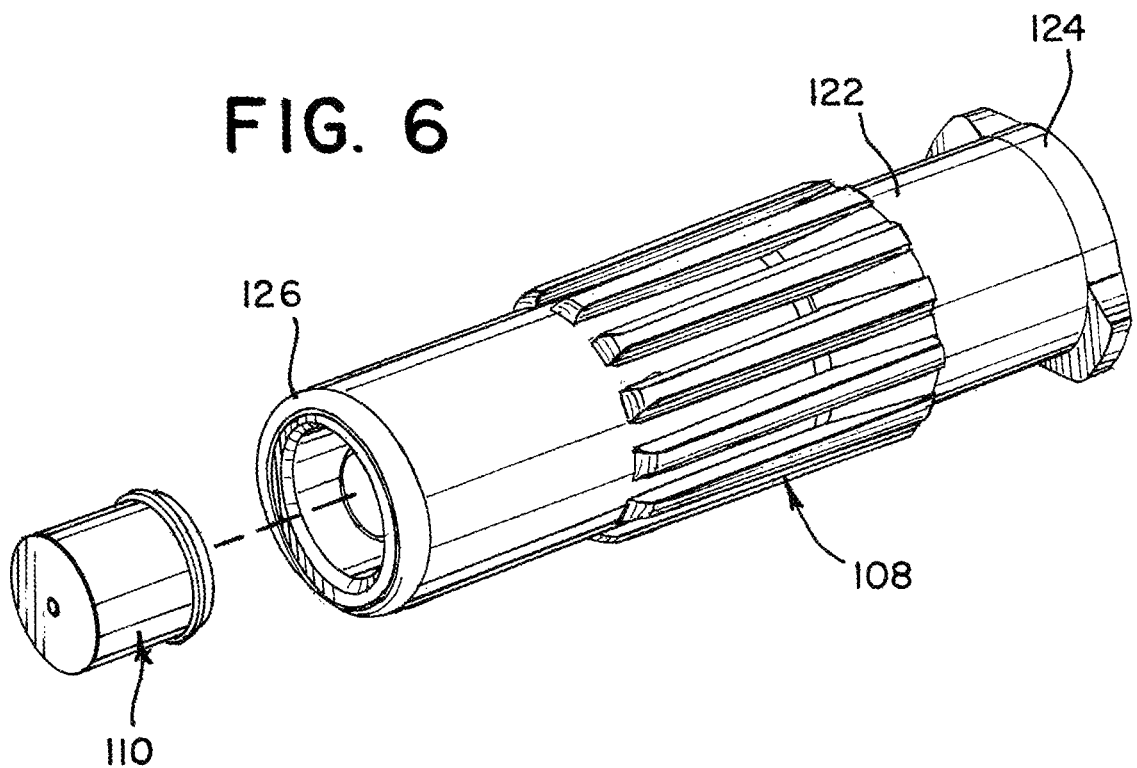
FIG. 6 illustrates a first step of a method of assembling the first orifice cup shown in FIG. 5 with a distal end of the first spray housing shown in FIGS. 4A-4C.
Figure 7:
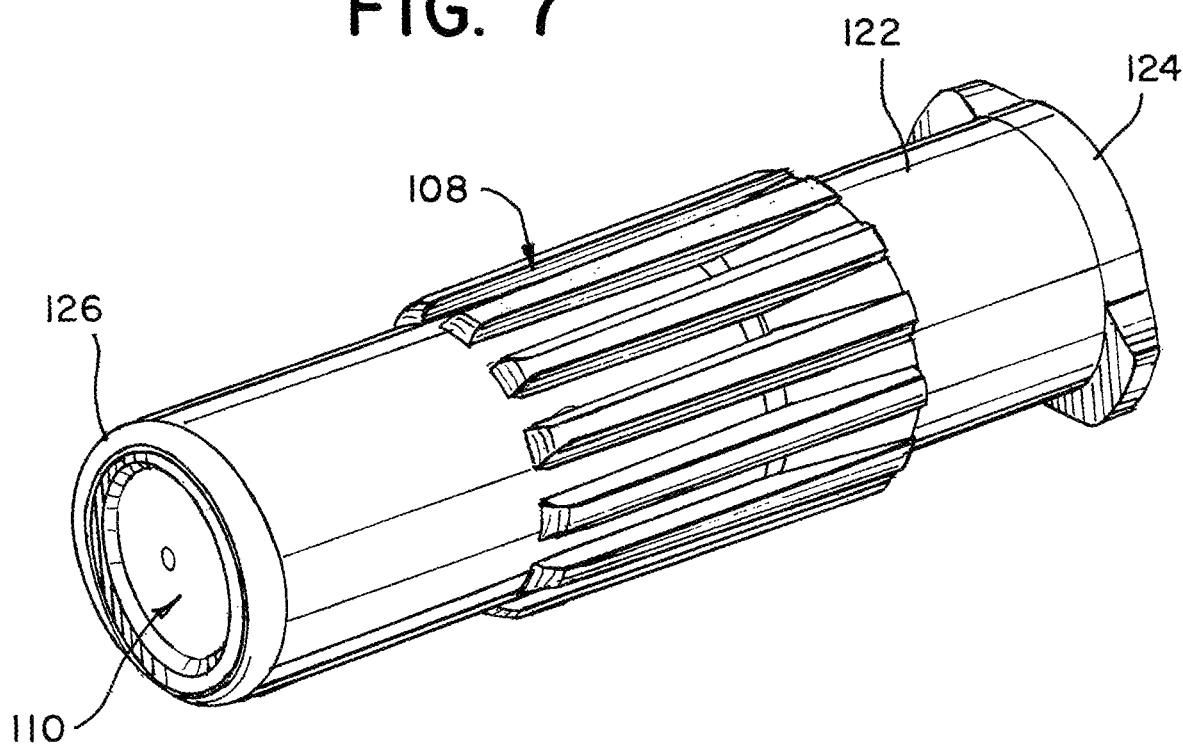
FIG. 7 illustrates a second step of a method of assembling the first orifice cup shown in FIG. 5 with the distal end of the first spray housing shown in FIGS. 4A-4C, in accordance with one embodiment of the present patent application.

Referring to FIGS. 5 and 6, in one embodiment, the first orifice cup 110 may be assembled with the first spray housing 108 by inserting a proximal end of the first orifice cup into the distal opening 130 located at the distal end 126 of the hollow tube 122 of the first spray housing 108 (FIG. 4C). FIG. 6 shows the first orifice cup 110 prior to insertion into the distal opening 130 located at the distal end 126 of the hollow tube 122 of the first spray housing 108. FIG. 7 shows the first orifice cup 110 after it has been inserted into the distal opening 130 (FIG. 6) located at the distal end 126 of the hollow tube 122 of the first spray housing 108. In one embodiment, the first orifice cup is preferably secured over the distal end of the insert of the hollow body of the first spray housing 108 (FIG. 7C).

Figure 8A:
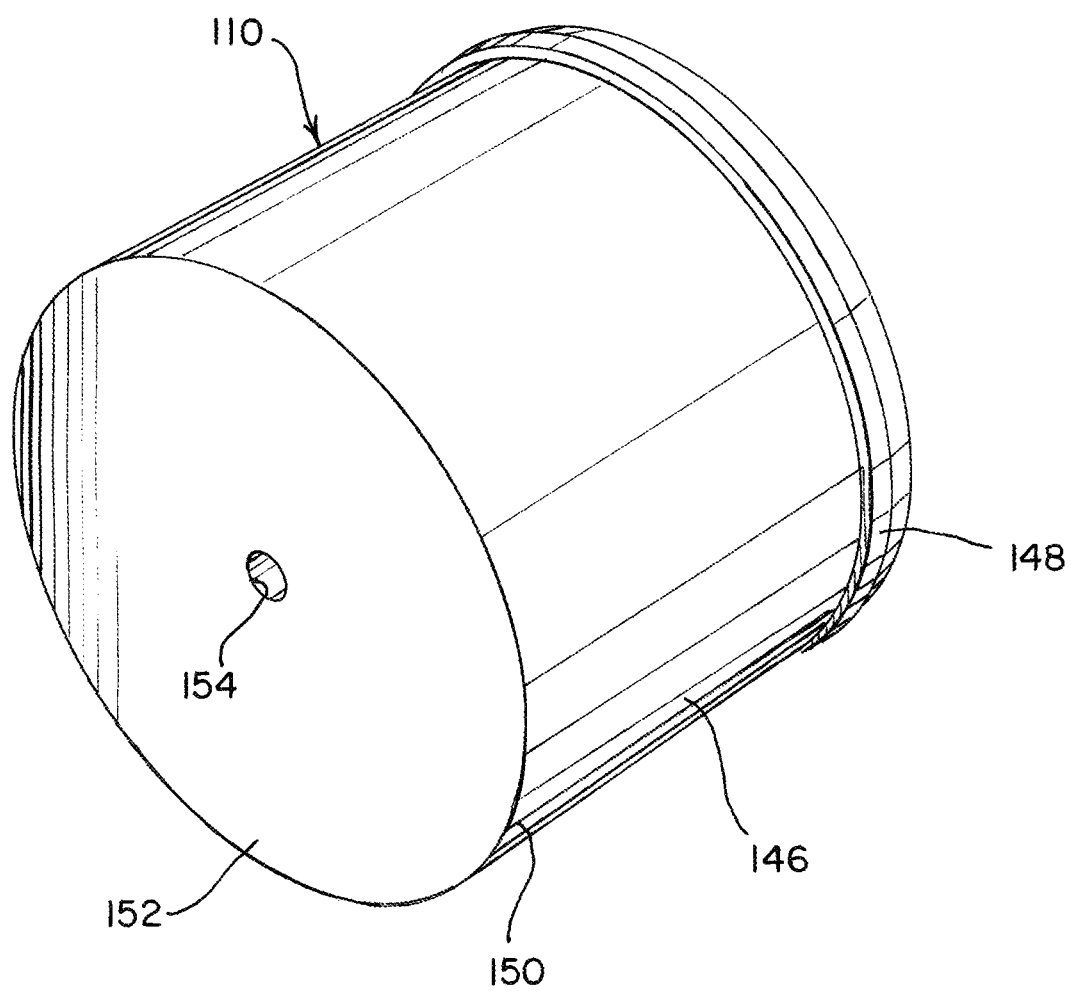
FIG. 8A is a perspective view of a distal end the first orifice cup shown in FIGS. 5-7, in accordance with one embodiment of the present patent application.
Figure 8B:
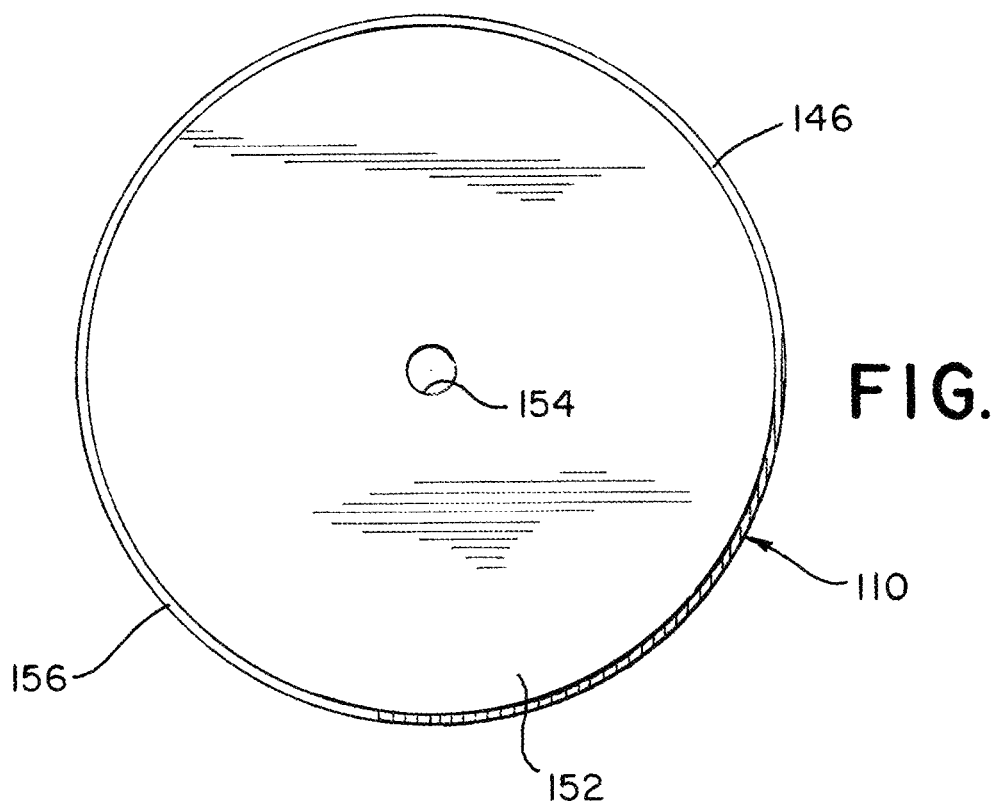
FIG. 8B is a distal end view of the first orifice cup shown in FIG. 8A.
Figure 8C:
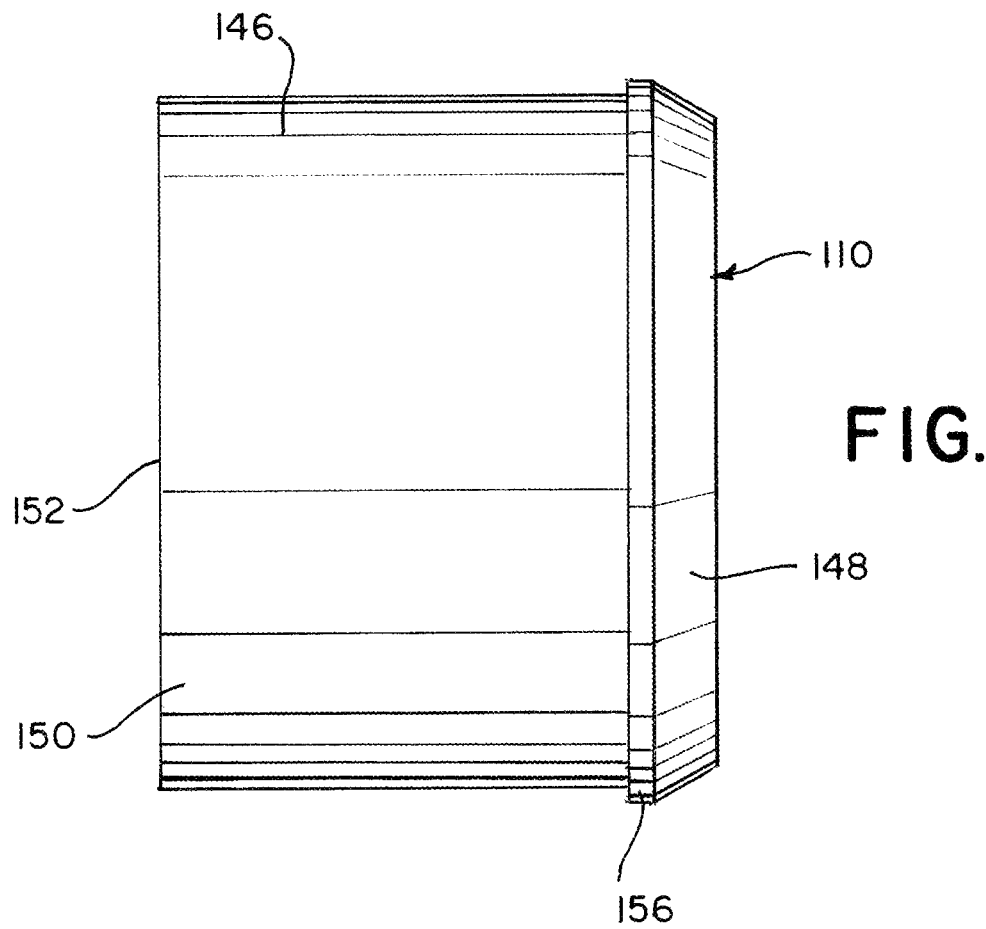
FIG. 8C is a side elevation view of the first orifice cup shown in FIGS. 8A and 8B.

Referring to FIGS. 8A-8C, in one embodiment, the first orifice cup 110 preferably includes an outer wall 146 having a proximal end 148 and a distal end 150. The outer wall 146 may have a cylindrical shape. In one embodiment, the first orifice cup 110 is open at the proximal end 148 of the outer wall 146 and is closed at the distal end 150 of the outer wall. In one embodiment, the distal end of the first orifice cup 110 is closed by a distal end wall 152 that includes a first spray opening 154 for spraying a fluid from the first orifice cup. The first spray opening may be centered on the distal end wall 152. In one embodiment, a first fluid may be introduced into a proximal opening at the proximal end 148 of the first orifice cup 110 and be directed toward the distal end of the first orifice cup for being sprayed through the first spray opening 154 formed in the distal end wall 152.

Referring to FIG. 8C, in one embodiment, the proximal end 148 of the first orifice cup 110 desirably includes an annular connecting flange 156 projecting therefrom that facilitates forming a connection between the first orifice cup 110 and an inner surface of the first spray housing that is located at the distal end 126 of the first spray housing 108 (FIGS. 6 and 7).

Figure 8D:
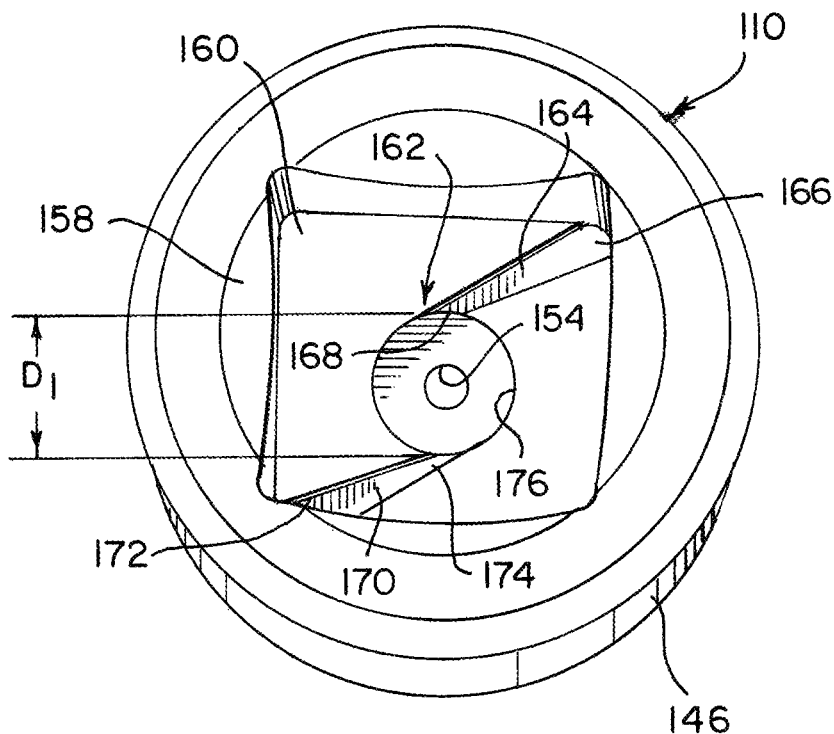
FIG. 8D is a perspective view of a proximal end of the first orifice cup shown in FIGS. 8A-8C.
Figure 8E:
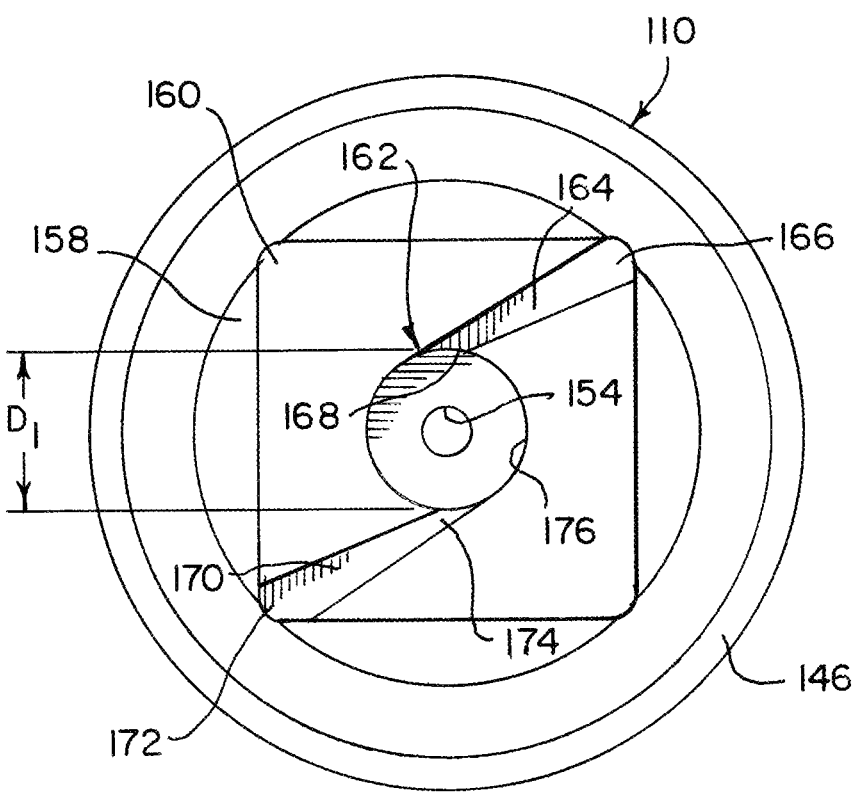
FIG. 8E is a proximal end view of the first orifice cup shown in FIGS. 8A-8D, whereby the first orifice cup has a first swirl chamber including swirl flutes and a first swirl chamber diameter, in accordance with embodiment of the present patent application.
Figures 1, 8E:
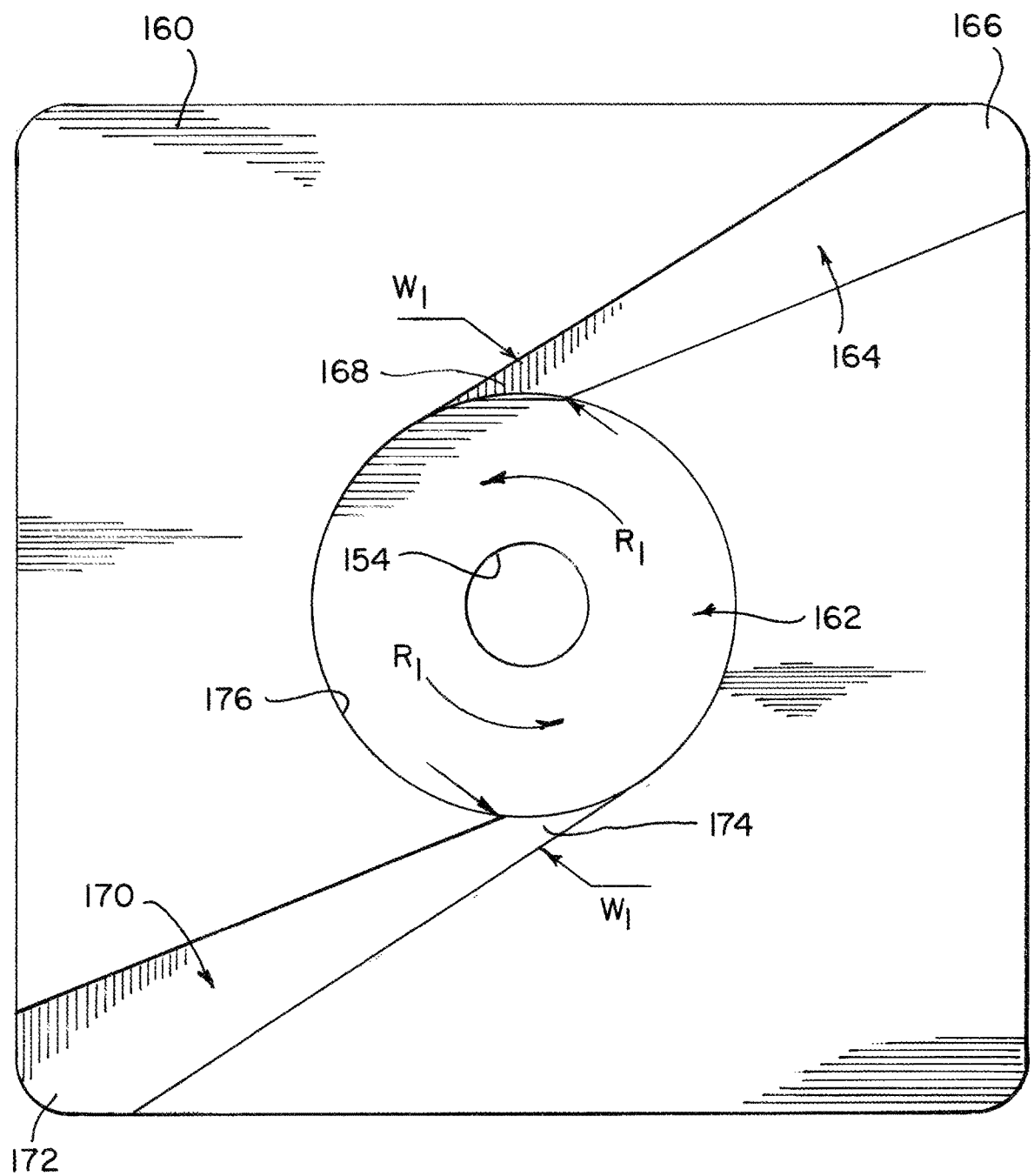

Referring to FIGS. 8D and 8E, in one embodiment, the first orifice cup 110 has a proximal opening 158 at the proximal end 148 of the outer wall 146. The proximal opening 158 extends preferably extends from the proximal end of the first orifice cup 110 to the distal end wall 152 (FIGS. 8A-8C) of the first orifice cup 110. The distal end wall 152 (FIG. 8C) of the first orifice cup preferably has an inner face 160 having a first fluid pathway 162 formed therein. In one embodiment, the first fluid pathway 162 is centered on the first spray opening 154 for rotating and directing a first fluid through the first spray opening. In one embodiment, the first fluid pathway 162 desirably includes a first flute 164 having an outer end 166 and an inner end 168. The first fluid pathway 162 preferably includes a second flute 170 having an outer end 172 and an inner end 174. The first and second flutes 164, 170 preferably direct the first fluid into an outer perimeter of a first swirl chamber 176 that extends around the first spray opening 154. In one embodiment, the first swirl chamber 176 preferably has a diameter $D_1$ of about 0.020-0.040 inches, and more preferably about 0.030 inches.

Figure 1:
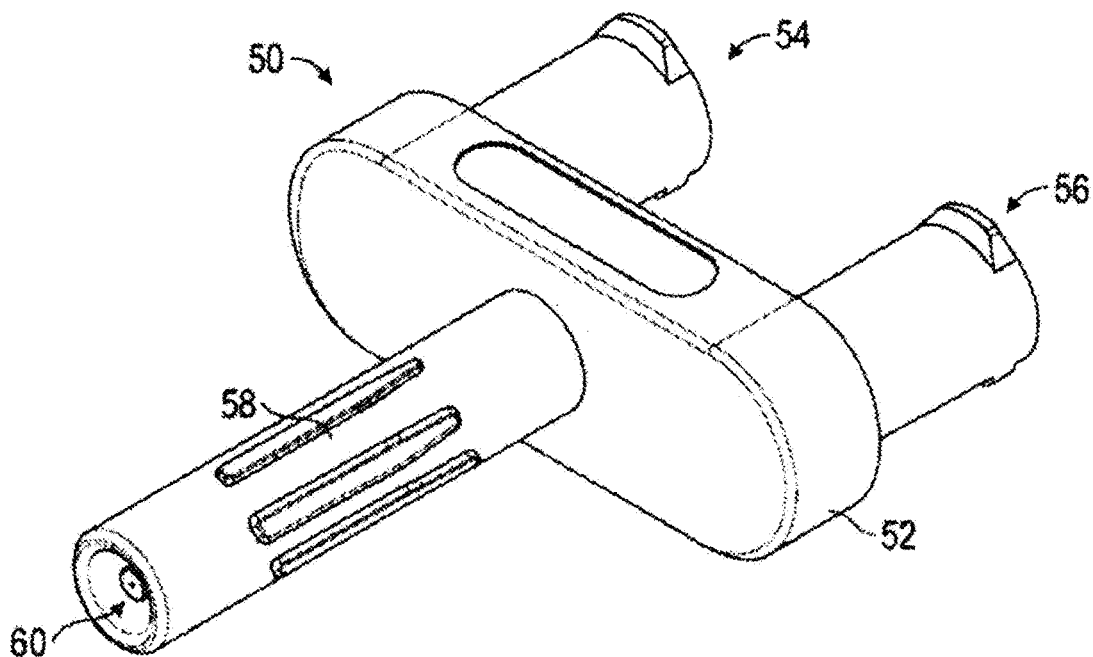
FIG. 1 is a perspective view of a prior art spray tip used to spray two fluids that react together.
Figure 2:
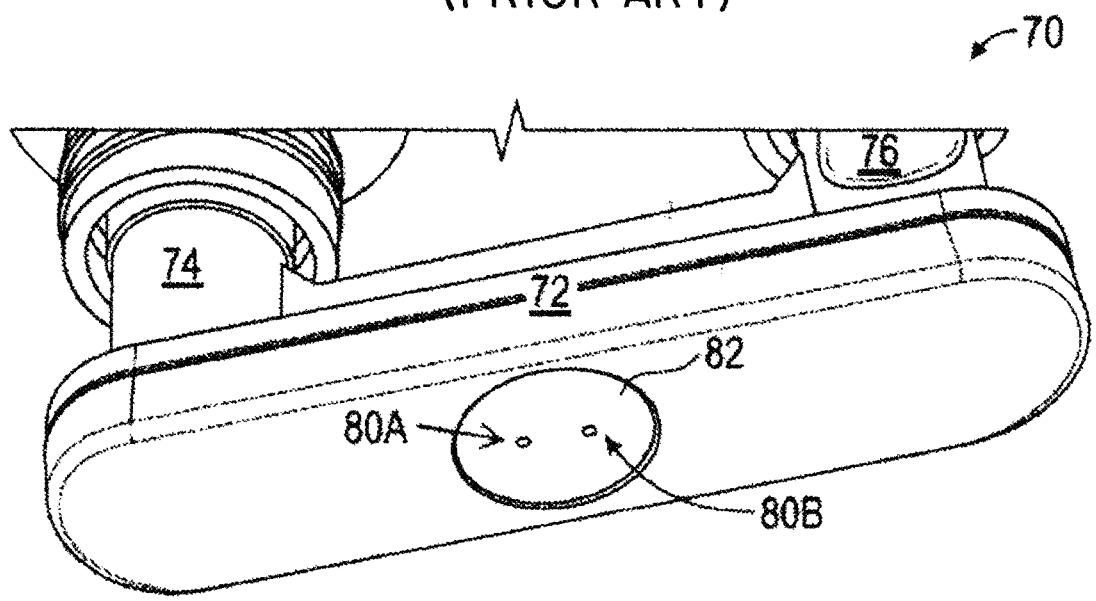
FIG. 2 is a perspective view of a distal end of a second prior art spray device used to spray two fluids that react together.

Referring to FIG. 8E-1, in one embodiment, the first fluid pathway 162 includes the first flute 164 that extends inwardly from an outer end 166 to an inner end 168 thereof. In one embodiment, the inner end 168 of the first flute 164 (i.e., the section of the first flute that directs a fluid into the outer perimeter of the first swirl chamber) preferably has a width $W_1$ of about 0.005 inches. In one embodiment, the second flute 170 extends between the outer end 172 and the inner end 174 thereof. In one embodiment, the inner end 174 of the second flute 170 (i.e., the section of the second flute that directs a fluid into the outer perimeter of the first swirl chamber) preferably has a width $W_1$ of about 0.005 inches that matches the width $W_1$ of the inner end 168 of the first flute 164. In one embodiment, the first and second flutes 164, 170 may have widths that narrow between the respective outer and inner ends thereof. In one embodiment, the width $W_1$ measurement that is used for determining the cross-sectional area of the first and second flutes 164, 170 is located at the respective inner ends 168, 174 of the first and second flutes, which are the sections of the flutes that are immediately adjacent the outer perimeter of the first swirl chamber 176.

In one embodiment, the first fluid is introduced into the proximal opening 158 (FIG. 8E) at the proximal end of the first orifice cup 110 and is directed into the outer ends 166, 172 of the respective first and second flutes 164, 170. The inwardly flowing first and second fluids are then directed into the outer perimeter of the first swirl chamber 176 whereupon the first fluid is rotated and/or spun in a counterclockwise direction designated $R_1$. The rotation of the fluid is preferably in a circular pattern. The first fluid continues to rotate in the counterclockwise direction $R_1$ within the first swirl chamber 176 for atomizing the fluid as it is sprayed from the first spray opening 154 formed in the distal end wall 152 (FIG. 8C) of the first orifice cup 110.

Figure 8F:
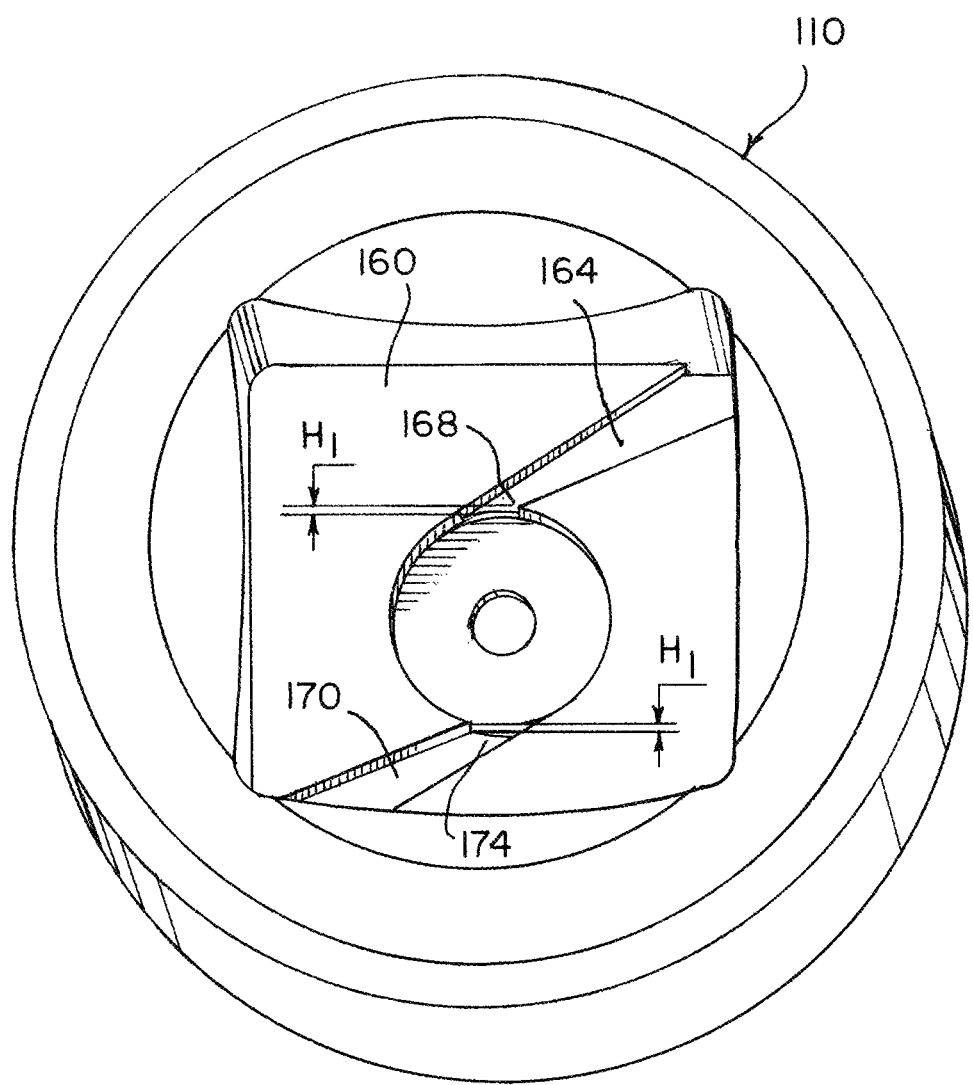
FIG. 8F is another perspective view of the proximal end of the first orifice cup shown in FIGS. 8A-8E.
Figure 8G:
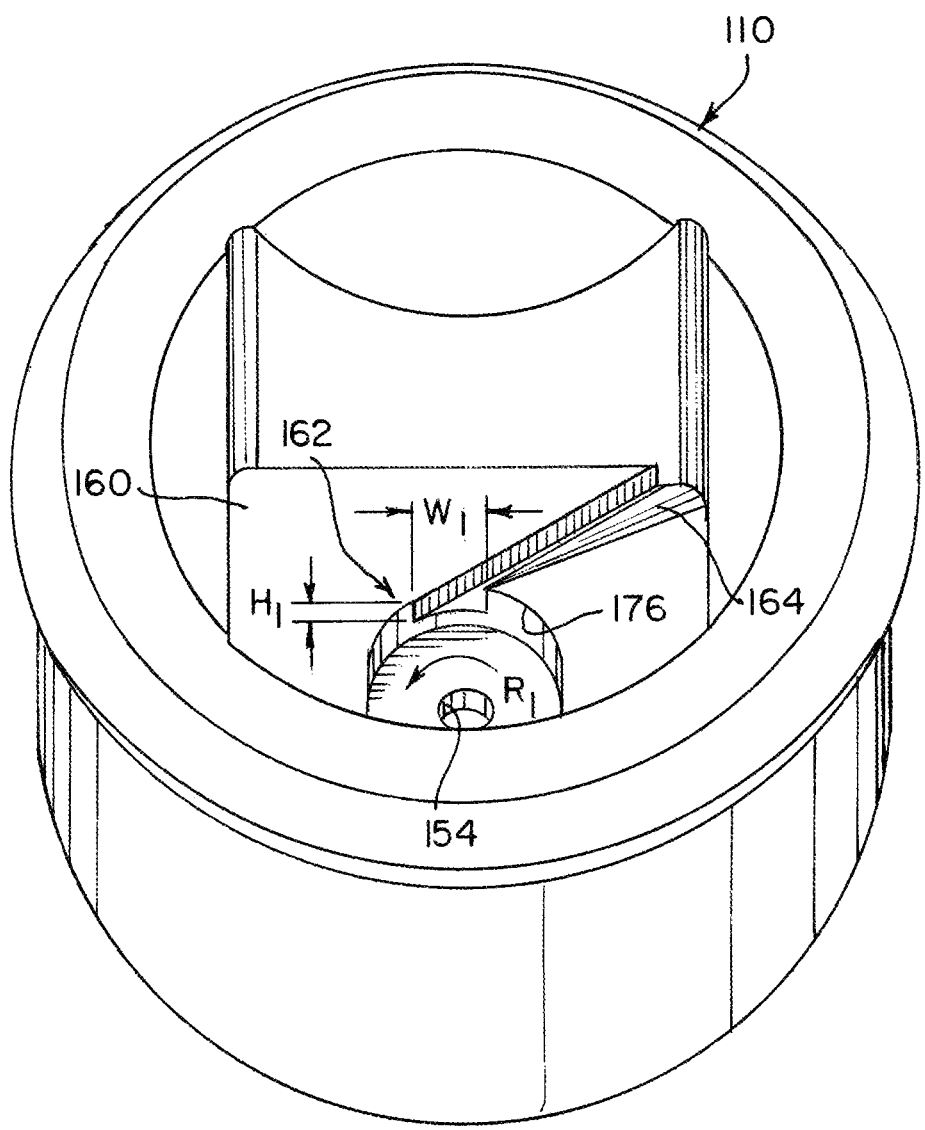
FIG. 8G is still another perspective view of the proximal end of the first orifice cup shown in FIG. 7F.

Referring to FIGS. 8F and 8G, in one embodiment, the first and second flutes 164, 170 have respective heights that are cut into the inner face 160 of the distal end wall 152 (FIG. 8C) of the first orifice cup 110. In one embodiment, the first flute 164 has a height $H_1$ of about 0.005 inches and the second flute 170 has a height $H_1$ that is also about 0.005 inches. In one embodiment, the height $H_1$ measurement that is used for determining the cross-sectional area of the first and second flutes 164, 170 is located at the respective inner ends 168, 174 of the first and second flutes, which are the sections of the flutes that are immediately adjacent the outer perimeter of the first swirl chamber 176.

Figure 8H:
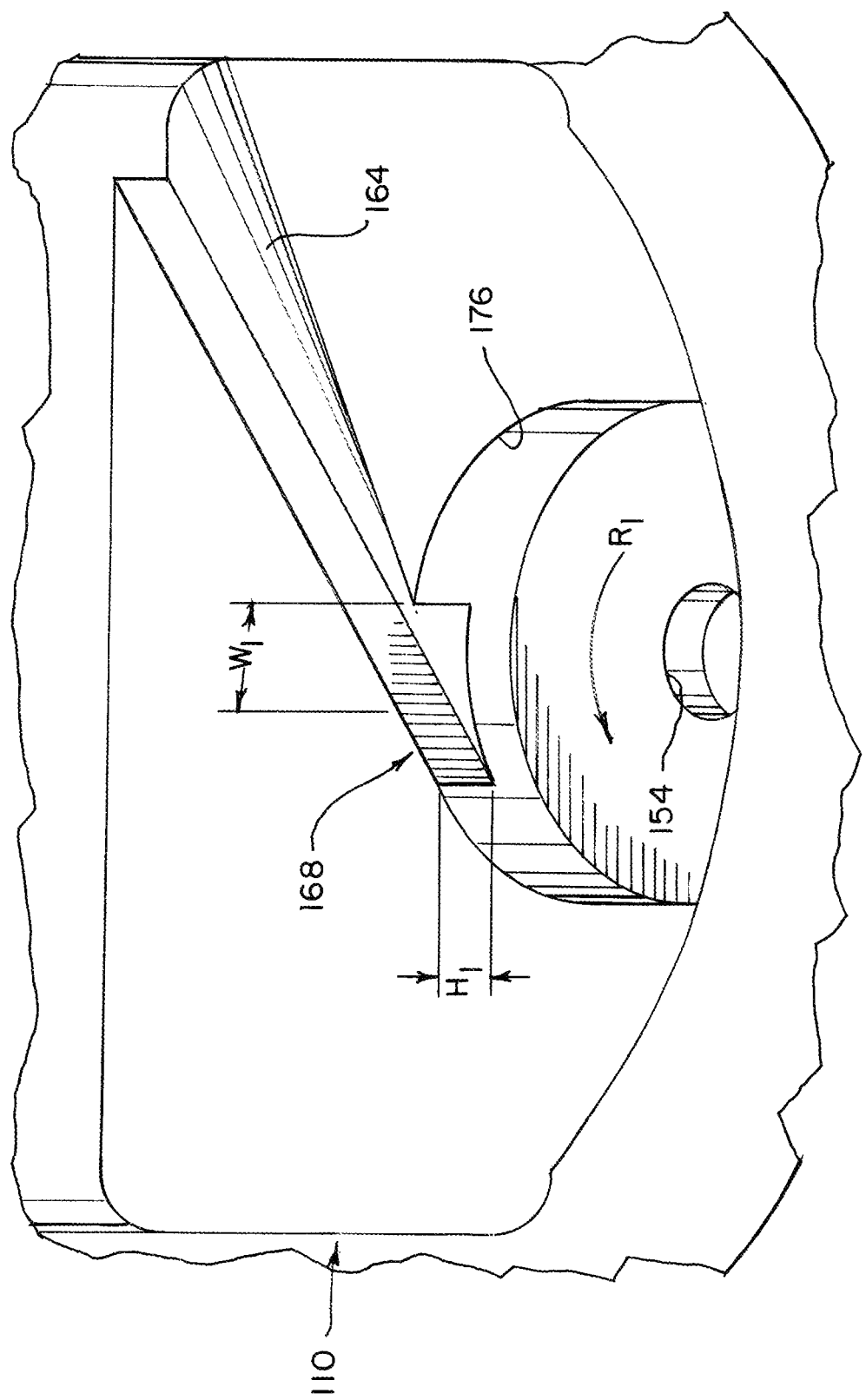
FIG. 8H is yet another perspective view of the proximal end of the first orifice cup shown in FIGS. 8F and 8G.

Referring to FIGS. 8G and 8H, in one embodiment, the first flute 164 of the first fluid pathway 162 is formed in the inner face 160 of the distal end wall 152 (FIG. 8C) of the first orifice cup 110. The first flute 164 has a height $H_1$ of about 0.005 inches and a width $W_1$ of about 0.005 inches. The first flute 164 directs the first fluid into the outer perimeter of the first swirl chamber 176, whereupon the first fluid is rapidly rotated within the first swirl chamber in the counterclockwise direction $R_1$ before being sprayed through the first spray opening 154 of the first orifice cup 110.

Figure 8I:
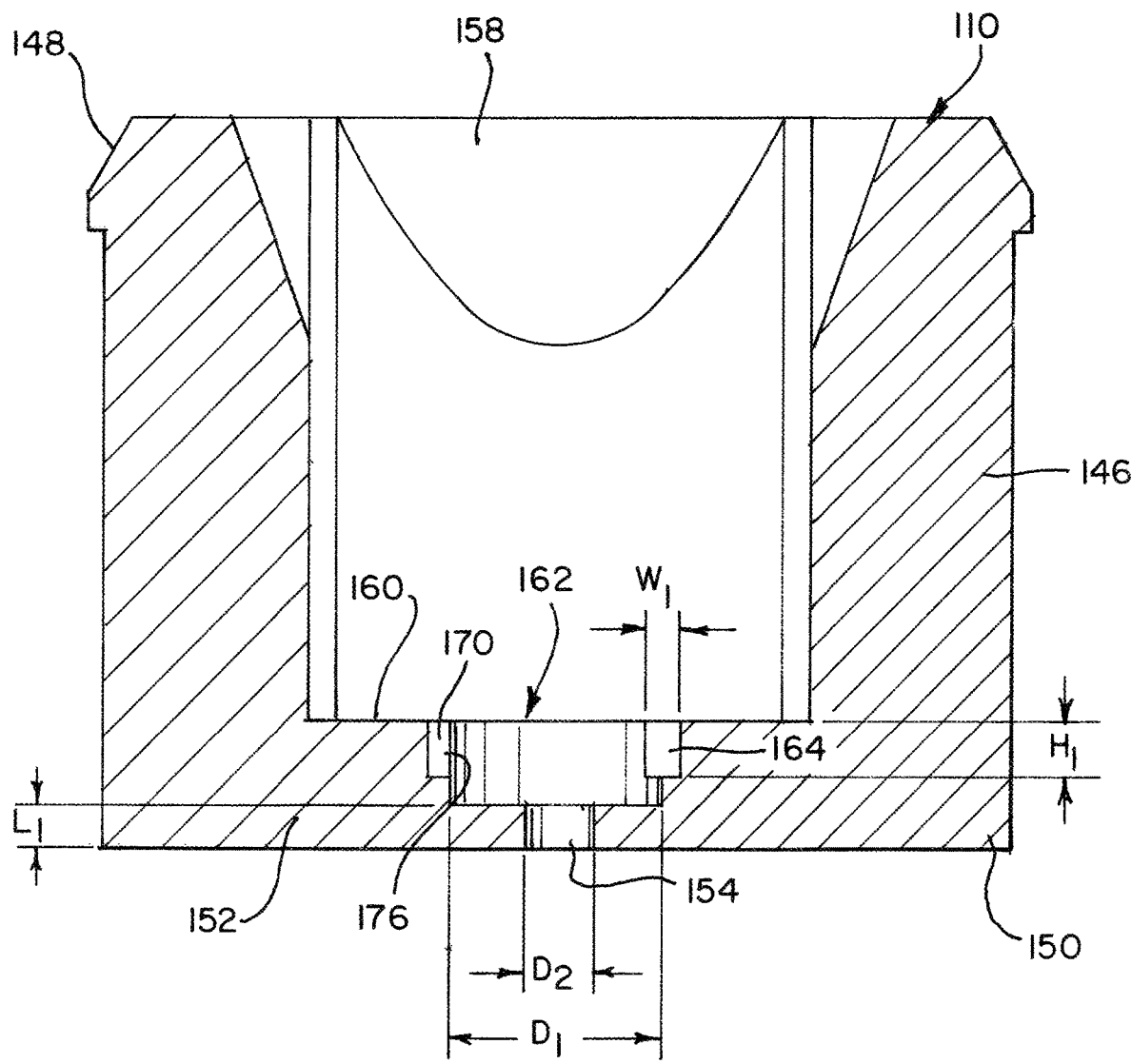
FIG. 8I is a cross-sectional view of the first orifice cup shown in FIGS. 8A-8H.

Referring to FIG. 8I, in one embodiment, the first orifice cup 110 includes the outer wall 146 with a cylindrical shape having a proximal end 148 and a distal end 150. The distal end 150 of the outer wall 146 is closed by the distal end wall 152. The proximal end 148 of the outer wall 146 has a proximal opening 158 that enables a first fluid to be directed into the proximal end of the first orifice cup 110. The proximal opening 158 also desirably enables the first orifice cup 110 to be secured over the first insert 134 of the first spray housing 108 (FIG. 4C).

In one embodiment, the distal end wall 152 of the first orifice cup 110 has the inner face 160. The first fluid pathway 162 is preferably formed (e.g., cut) in the inner face 160 of the distal end wall 152. The first fluid pathway 162 preferably includes the first flute 164 and the second flute 170 that direct the first fluid into the outer perimeter of the first swirl chamber 176. The first swirl chamber 176 is preferably aligned with the first spray opening 154 for spraying the first fluid from the distal end 150 of the first orifice cup 110. In one embodiment, the first swirl chamber 176 has a diameter $D_1$ of about 0.020-0.040 inches, and more preferably about 0.030 inches. In one embodiment, the first flute 164 has a width $W_1$ of about 0.005 inches and a height $H_1$ of about 0.005 inches. In one embodiment, the first spray opening 154 has a length $L_1$ of about 0.010 inches and an inner diameter $ID_2$ of about 0.010 inches.

Figure 9B:
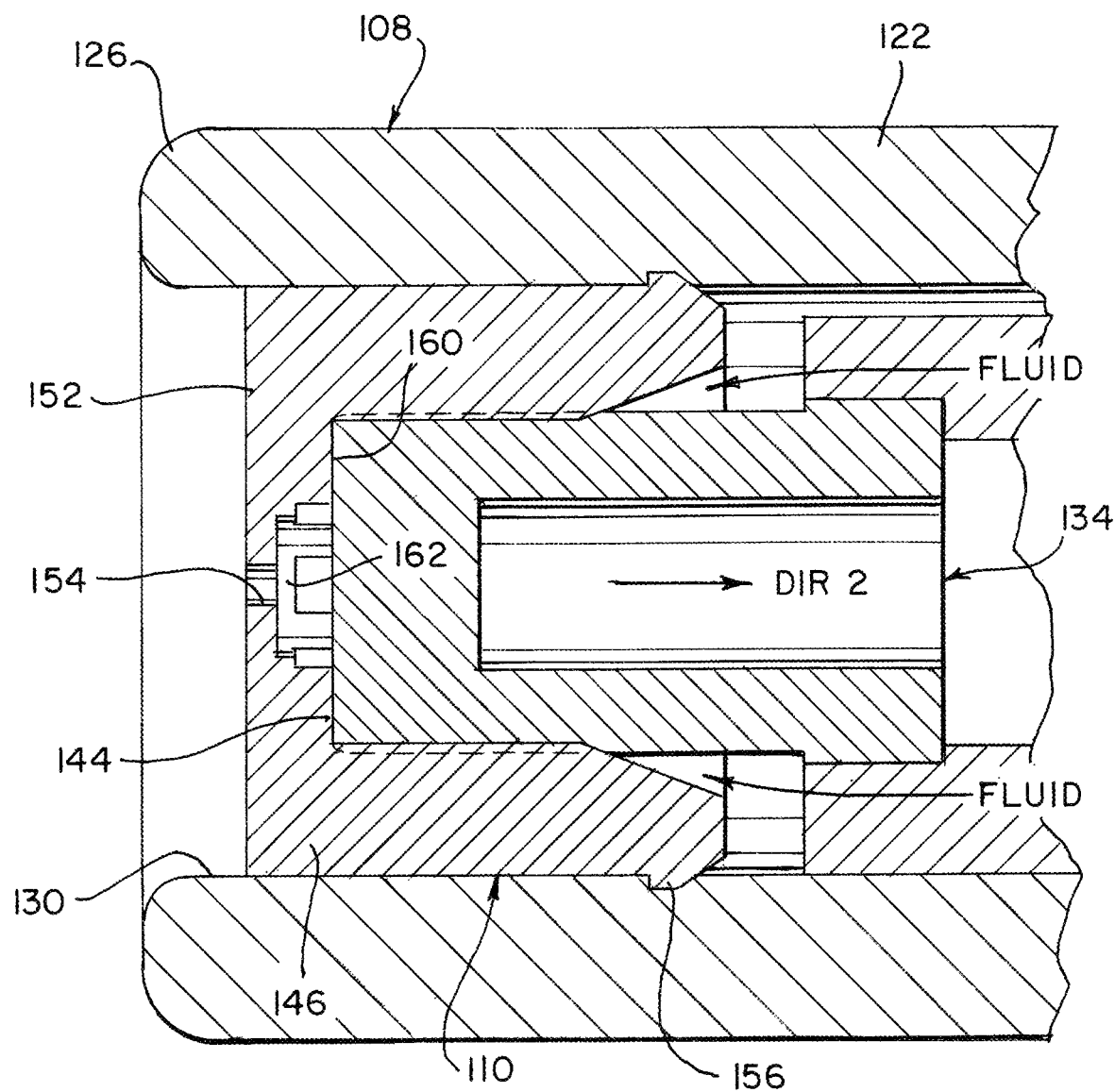
FIG. 9B is a magnified view of the first orifice cup and the distal end of the spray housing shown in FIG. 9A.

Referring to FIGS. 9A and 9B, in one embodiment, the first orifice cup 110 is assembled with the distal end 126 of the hollow tube 122 of the first spray housing 108 by juxtaposing the proximal opening 158 (FIG. 8I) at the proximal end 148 of the first orifice cup 110 with the distal end face 144 of the insert 134 located at the distal end 126 of the hollow tube 122. The outer diameter of the insert may closely match the inner diameter of the outer wall of the first orifice cup. In one embodiment, the first orifice cup 110 is pressed in the proximal direction designated DIR2 toward the proximal end 124 of the hollow tube 122 of the first spray housing 108. The first orifice cup 110 is advanced proximally until the inner surface 160 of the distal end wall 152 of the first orifice cup 110 contacts the distal end face 144 of the insert 134 of the first spray housing 108. The annular securing flange 152 at the proximal end of the first orifice cup 110 preferably engages an inner surface of the hollow tube of the first spray housing for holding the first orifice cup 110 within the distal opening 130 at the distal end 126 of the hollow tube 122 of the first spray housing 108.

In one embodiment, the first fluid is directed into the proximal opening 128 at the proximal end 124 of the hollow tube 122 and flows downstream between the inner surface of the outer wall of the first orifice cup and the outer surface of the cylindrical wall of the insert. The first fluid is directed into one or more spaces located between the outer surface of the cylindrical wall 136 of the insert 134 and the inner surface of the outer wall 146 of the first orifice cup 110. The first fluid preferably flows distally toward the distal end of the insert 134 whereupon the first fluid is directed into the outer ends of the respective first and second flutes 164, 170 (FIG. 8E) of the first orifice cup 110, and further directed into the outer perimeter of the first swirl chamber 176 that is aligned with the first spray opening 154 of the first orifice cup 110. The first fluid is rotated in the counterclockwise direction $R_1$ within the first swirl chamber 176 (FIG. 8E-1) as it is atomized and sprayed from the first spray opening 154 of the first orifice cup 110.

In one embodiment, the second spray housing 116 of the spray device 100 (FIG. 3) may have the same size, shape and/or configuration as the first spray housing shown and described above in FIGS. 4A-4C. The second orifice cup 118 (FIG. 3) may be inserted into a distal opening at the distal end of the second spray housing for assembling the second orifice cup with the second spray housing.

Figure 10A:
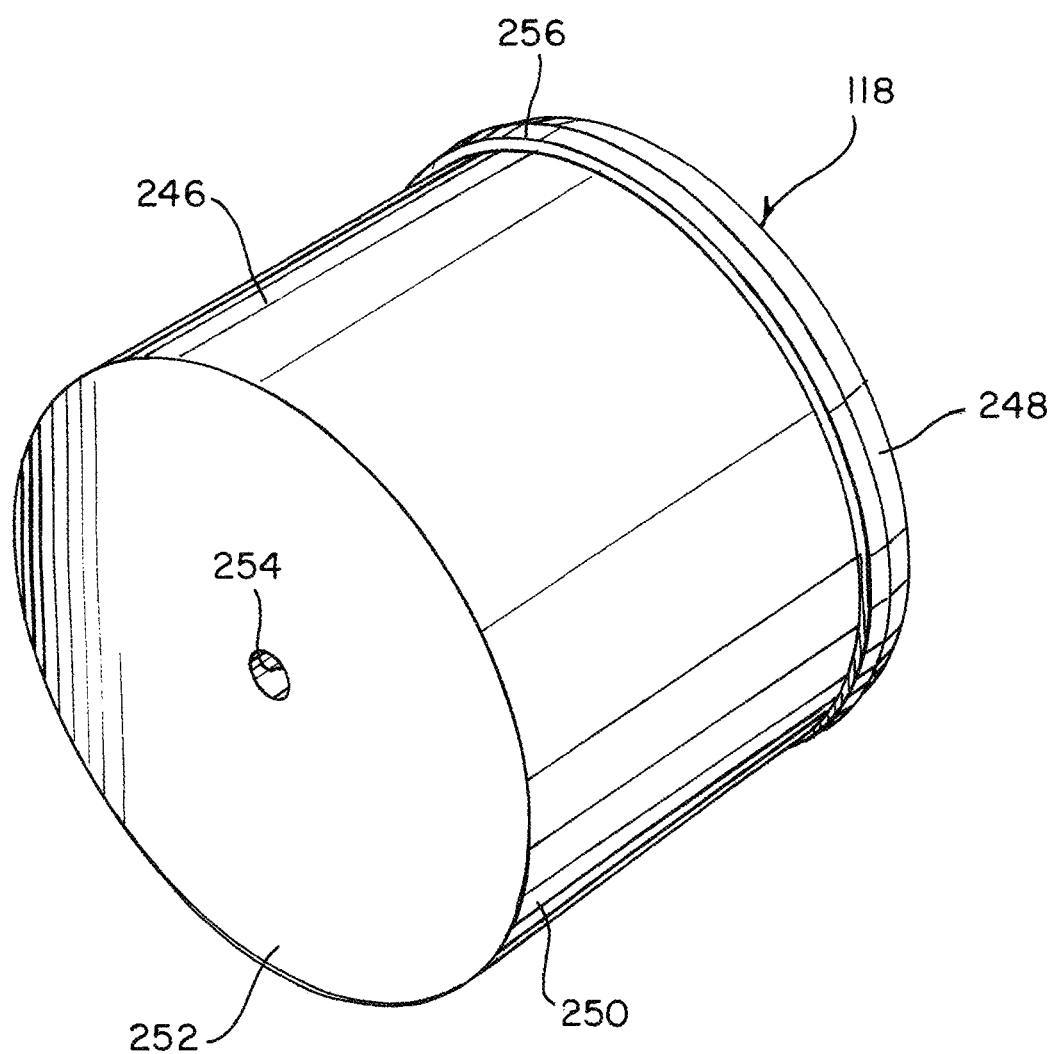
FIG. 10A is a perspective view of a distal end the second orifice cup shown in FIG. 3, in accordance with one embodiment of the present patent application.
Figure 10B:
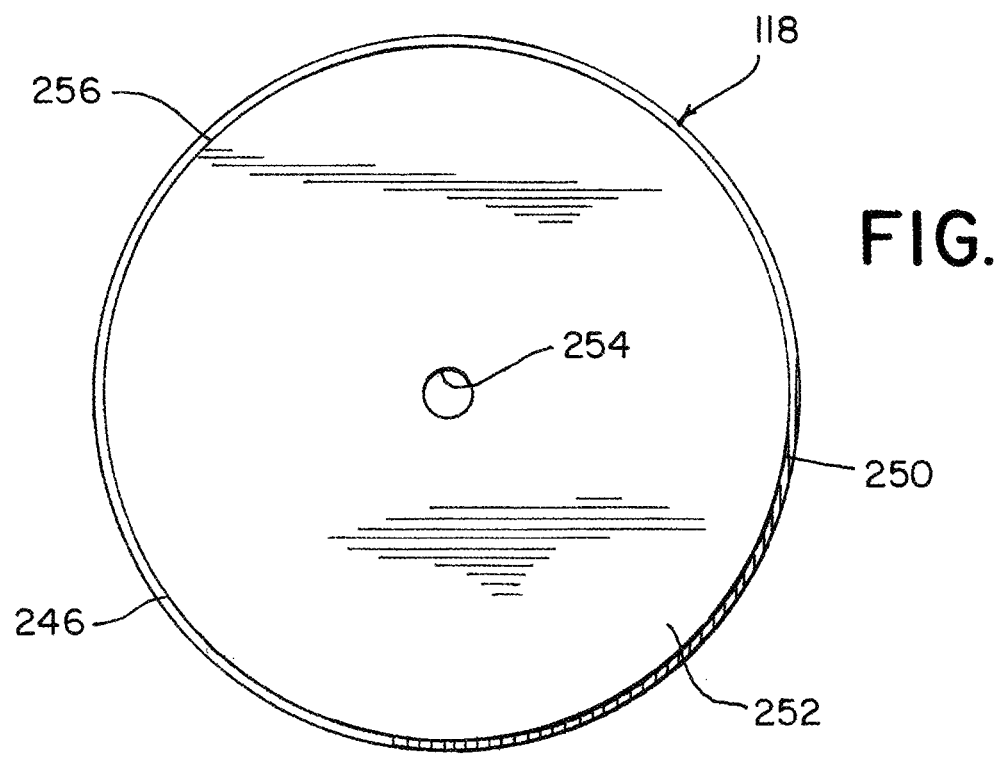
FIG. 10B is a distal end view of the second orifice cup shown in FIG. 10A.
Figure 10C:
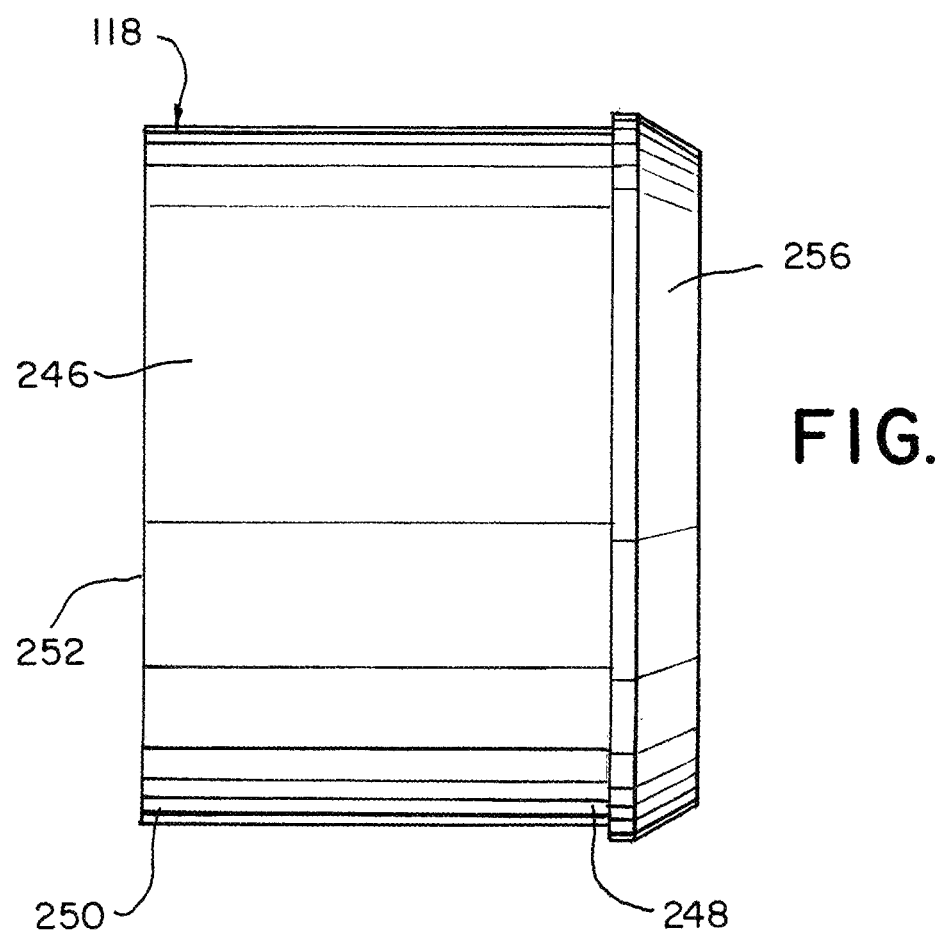
FIG. 10C is a side elevation view of the second orifice cup shown in FIGS. 10A and 10B.

Referring to FIGS. 10A-10C, in one embodiment, the second orifice cup 118 preferably includes an outer wall 246 having a proximal end 248 and a distal end 250. The outer wall 246 of the second orifice cup may have a cylindrical shape. In one embodiment, the second orifice cup 118 is open at the proximal end 248 of the outer wall 246 and is closed at the distal end 250 of the outer wall. In one embodiment, the distal end of the second orifice cup 118 is closed by a distal end wall 252 that includes a second spray opening 254 for dispensing/spraying a second fluid that reacts with the first fluid that is dispensed/sprayed from the first spray tip. The second spray opening may be centered on the distal end wall 252. In one embodiment, a second fluid may be introduced into a proximal opening at the proximal end 248 of the second orifice cup 210 and directed toward a distal end of the second orifice cup for being sprayed through the second spray opening 254 formed in the distal end wall 252.

Referring to FIG. 10C, in one embodiment, the proximal end 248 of the second orifice cup 118 desirably includes an annular connecting flange 256 projecting therefrom that facilitates forming a connection between the second orifice cup 118 and an inner surface of the second spray housing that is located at the distal end of the second spray housing 116 (FIG. 3).

Figure 10D:
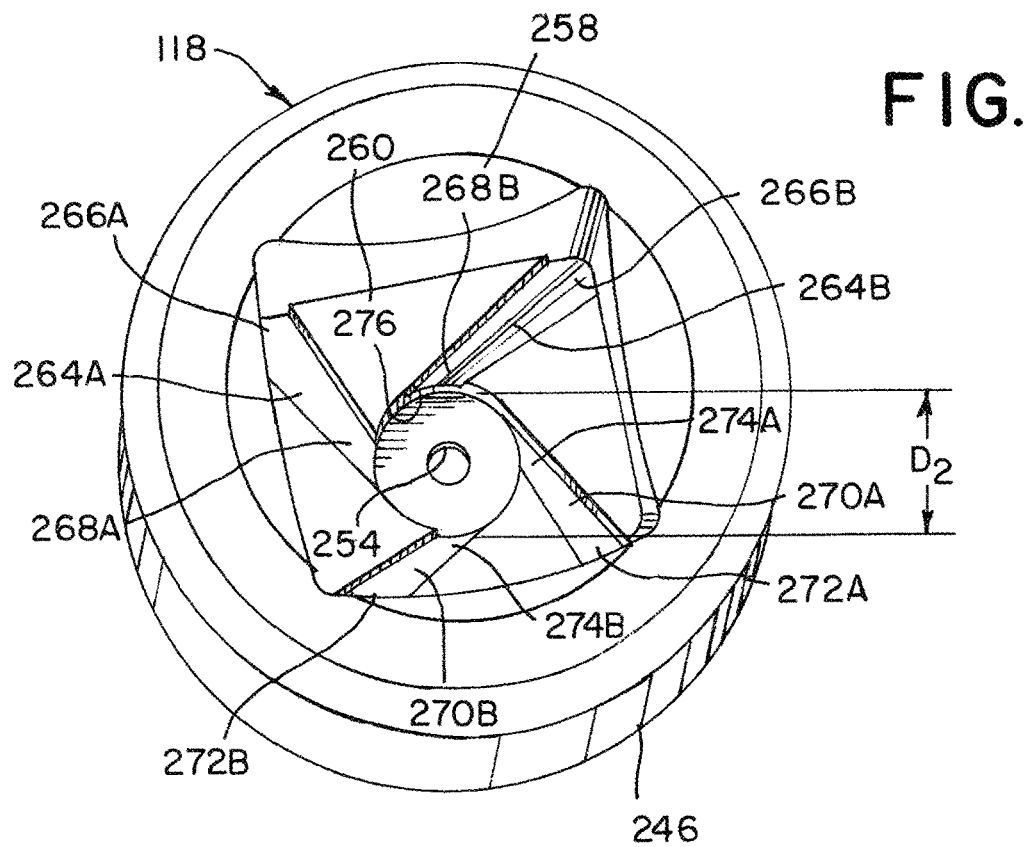
FIG. 10D is a perspective view of a proximal end of the second orifice cup shown in FIGS. 10A-10C.
Figure 10E:
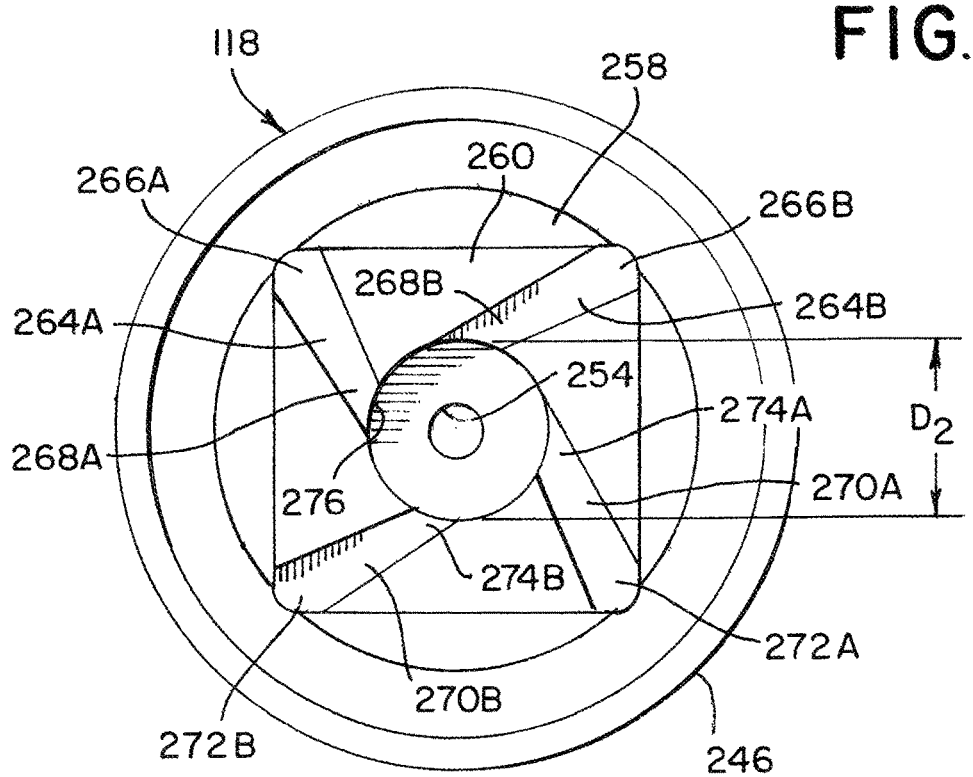
FIG. 10E is a proximal end view of the second orifice cup shown in FIGS. 10A-10D, whereby the second orifice cup has a second swirl chamber including swirl flutes and a second swirl chamber diameter, in accordance with embodiment of the present patent application.
Figures 1, 10E:
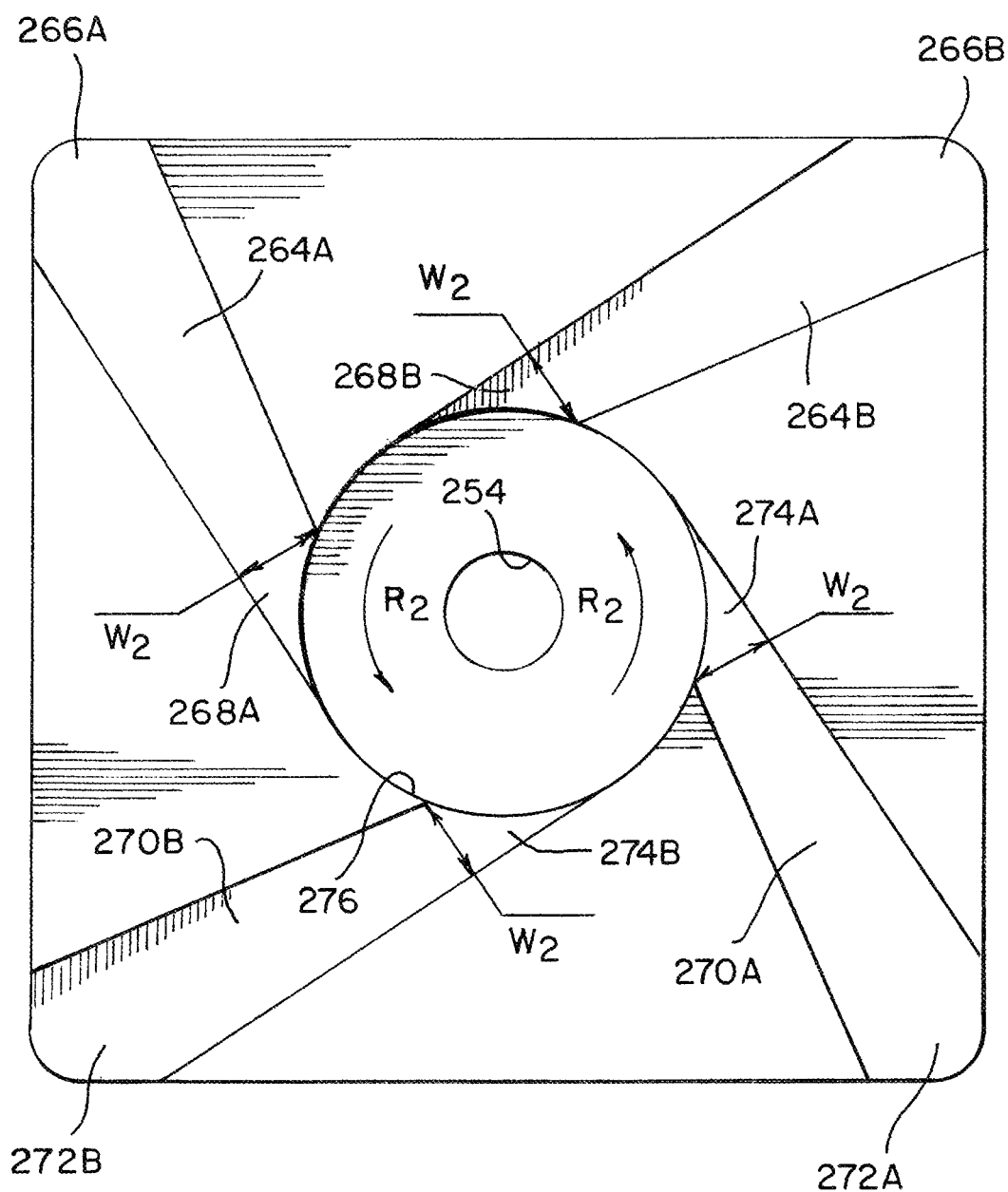

Referring to FIGS. 10D and 10E, in one embodiment, the second orifice cup 118 desirably has a proximal opening 258 at the proximal end 248 (FIG. 10C) of the outer wall 246. The proximal opening 258 preferably extends to the distal end wall 252 (FIGS. 10A-10C) of the second orifice cup 118. The distal end wall 252 (FIG. 10C) of the second orifice cup preferably has an inner face 260 having a second fluid pathway 262 formed therein. In one embodiment, the second fluid pathway 262 is preferably centered on the second spray opening 254 for directing a second fluid through the second spray opening. In one embodiment, the second fluid pathway 262 desirably includes a first flute 264A having an outer end 266A and an inner end 268A, a second flute 264B having an outer end 266B and an inner end 268B, a third flute 270A having an outer end 272A and an inner end 274A, and a fourth flute 270B having an outer end 272B and an inner end 274B. The four flutes 264A, 264B, 270A and 270B preferably direct the second fluid into an outer perimeter of a second swirl chamber 276 that surrounds the second spray opening 254 of the second orifice cup 118. In one embodiment, the second swirl chamber 276 has a diameter $D_2$ of about 0.020-0.040 inches, and more preferably about 0.030 inches. In one embodiment, the diameter $D_1$ of the first swirl chamber 176 (FIG. 8E) and the diameter $D_2$ of the second swirl chamber are the same.

Referring to FIG. 10E-1, in one embodiment, the second fluid pathway 262 preferably includes the first flute 264A that extends inwardly from an outer end 266A to an inner end 268A thereof. In one embodiment, the inner end 268A of the first flute 264A has a width $W_2$ of about 0.005 inches. In one embodiment, the second flute 264B extends between the outer end 266B and the inner end 268B thereof. In one embodiment, the inner end 268B of the second flute 264B has a width $W_2$ of about 0.005 inches that matches the width $W_2$ of the second end 268A of the first flute 264A. In one embodiment, the third flute 270A extends between the outer end 272A and the inner end 274A thereof. In one embodiment, the inner end 274A of the third flute 270A has a width $W_2$ of about 0.005 inches that matches the widths $W_2$ of the inner ends 268A, 268B of the first and second flutes 264A, 264B, respectively. In one embodiment, the fourth flute 270B extends between the outer end 272B and the inner end 274B thereof. In one embodiment, the inner end 274B of the fourth flute 270B preferably has a width $W_2$ of about 0.005 inches that matches the widths $W_2$ of the inner ends 268A, 268B, 274A of the first, second, and third flutes 264A, 264B, 270A, respectively. In one embodiment, the four width $W_2$ measurements that are used for determining the cross-sectional areas of the four flutes 264A, 264B, 270A, 270B are located at the respective inner ends of the four flutes, which are the sections of the four flutes that are immediately adjacent the outer perimeter of the second swirl chamber 276.

In one embodiment, the second fluid may be introduced into the proximal opening 258 (FIG. 10E) located at the proximal end of the second orifice cup 118, whereupon the second fluid is directed into the outer ends 266A, 266B, 272A, and 272B of the respective flutes 264A, 264B, 270A, 270B of the second orifice cup. The second fluid is preferably directed into the outer perimeter of the second swirl chamber 276, whereupon the second fluid is rapidly rotated in a counterclockwise direction designated $R_2$. The second fluid continues to rotate within the second swirl chamber 276 in the counterclockwise direction designated $R_2$ as the second fluid is sprayed from the second spray opening 254 formed in the distal end wall 252 (FIG. 10C) of the second orifice cup 118.

Figure 10F:
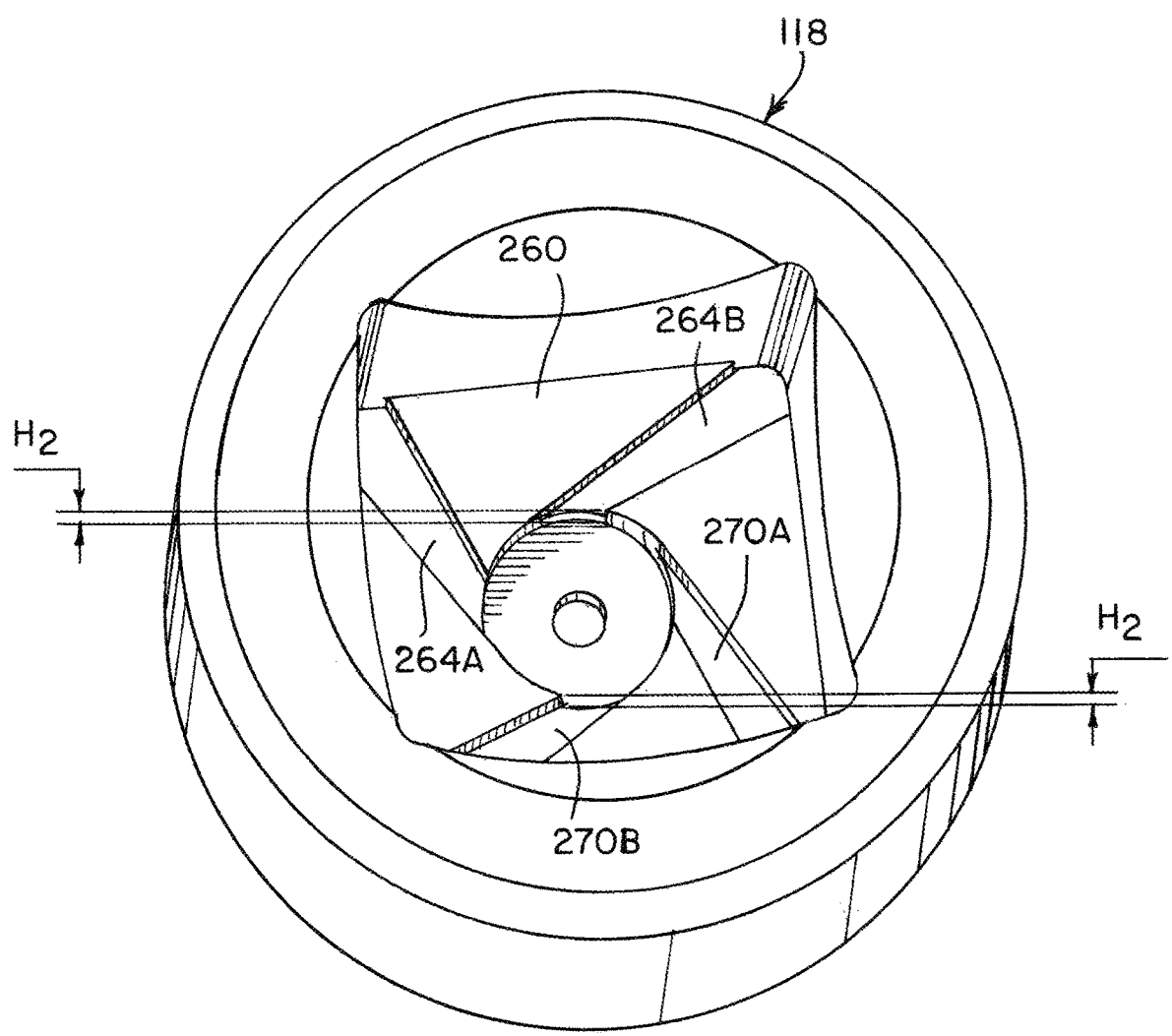
FIG. 10F is another perspective view of the proximal end of the second orifice cup shown in FIGS. 10A-10E.
Figure 10G:
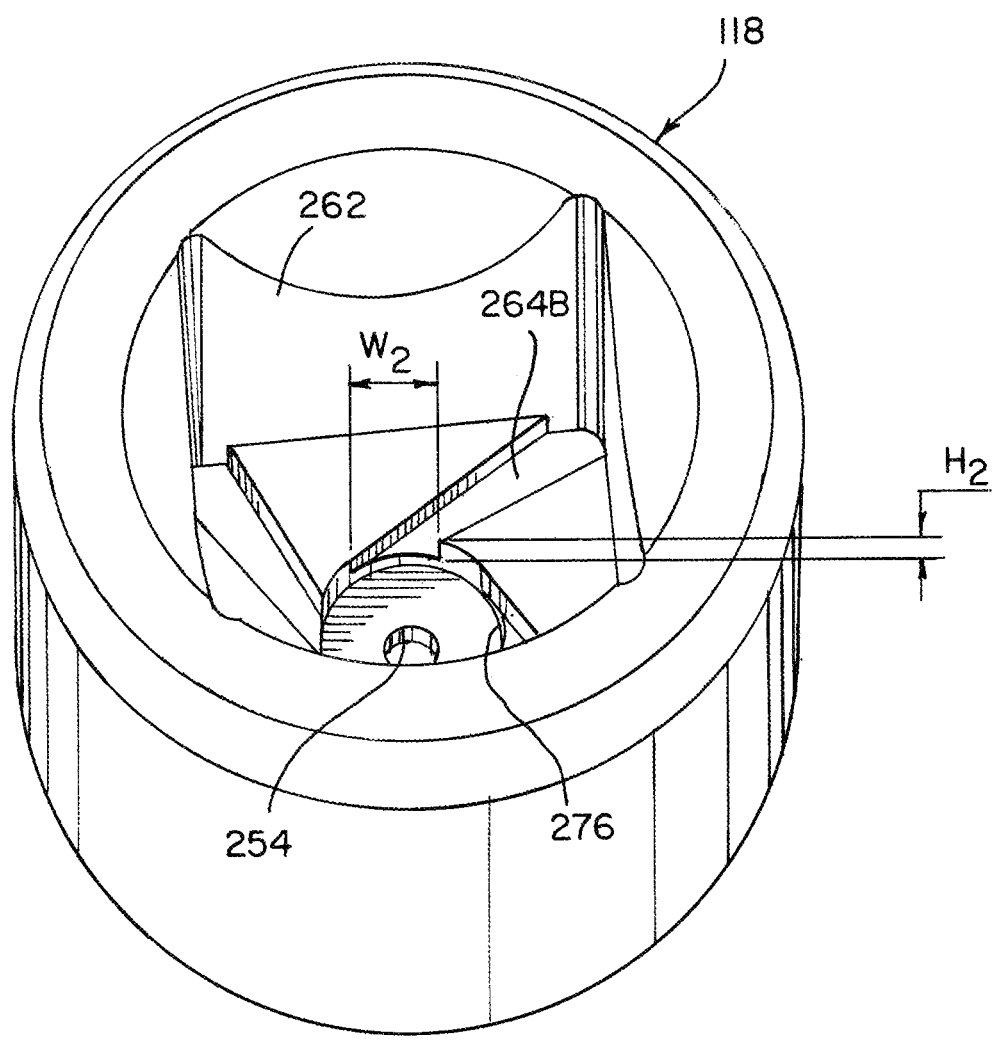
FIG. 10G is yet another perspective view of the proximal end of the second orifice cup shown in FIG. 10F.
Figure 101:
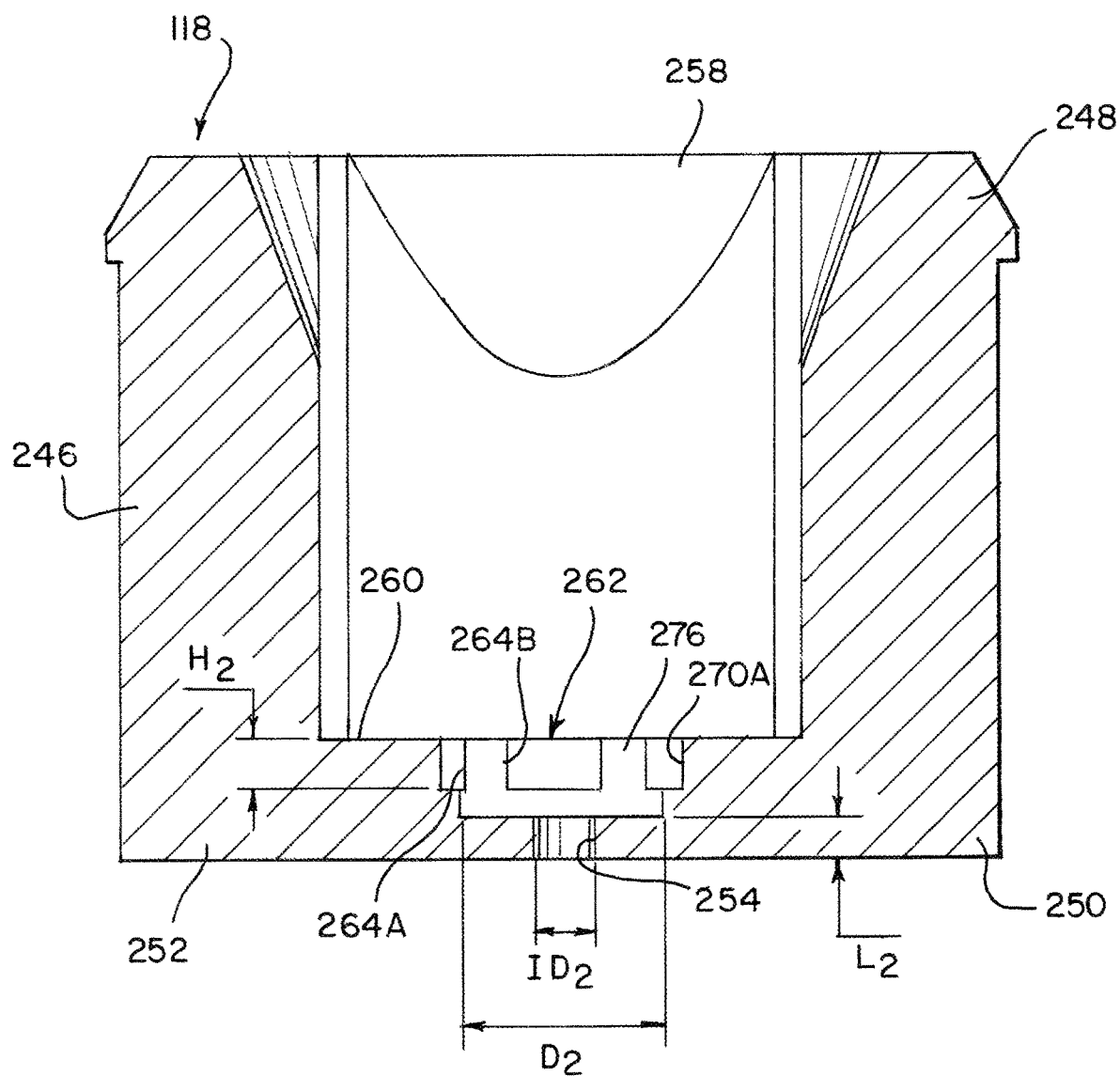

Referring to FIGS. 10F and 10G, in one embodiment, the four flutes 264A, 264B, 270A, 270B have respective heights that are formed in (e.g., cut) the inner face 260 of the distal end wall 252 (FIG. 10C) of the second orifice cup 118. In one embodiment, each of the four flutes 264A, 264B, 270A and 270B desirably has a height $H_2$ of about 0.010 inches. In one embodiment, the height $H_2$ measurements that are used for determining the cross-sectional areas of the four flutes 264A, 264B, 270A, 270B are located at the respective inner ends of the four flutes, which are the sections of the four flutes that are immediately adjacent the outer perimeter of the second swirl chamber 276.

Referring to FIGS. 10G and 10H, in one embodiment, the first flute 264A of the second fluid pathway 262 is formed in the inner face 260 of the distal end wall 252 (FIG. 10C) of the second orifice cup 118. The first flute 264A preferably has a height $H_2$ of about 0.010 inches and a width $W_2$ of about 0.005 inches. The first flute 264A directs the second fluid into the outer perimeter of the second swirl chamber 276, whereupon the second fluid is rotated in the counter-clockwise direction $R_2$ as it is sprayed from the second spray opening 254 of the second orifice cup 118.

In one embodiment, the second flute 264B of the second swirl chamber 262 is formed in the inner face 260 of the distal end wall 252 (FIG. 10C) of the second orifice cup 118. The second flute 264B has a height $H_2$ of about 0.010 inches and a width $W_2$ of about 0.005 inches. The second flute 264B directs the second fluid into the outer perimeter of the second swirl chamber 276, whereupon the second fluid is rotated in the counterclockwise direction $R_2$ as it is sprayed from the second spray opening 254 of the second orifice cup 118. The third and fourth flutes 270A, 270B (FIG. 10F) preferably have similar heights and widths and perform similar functions as the first and second flutes shown in FIG. 10G.

Referring to FIG. 10I, in one embodiment, the second orifice cup 118 preferably includes the outer wall 246 having a proximal end 248 and a distal end 250. The distal end 250 of the outer wall 246 is closed by a distal end wall 252. The proximal end 248 of the outer wall 246 has a proximal opening 258 for directing the second fluid into the proximal end of the second orifice cup 118.

In one embodiment, the distal end wall 252 has the inner face 260. The second fluid pathway 262 is preferably formed in the inner face 260 of the distal end wall 252. The second fluid pathway 262 preferably includes the four flutes 264A, 264B, 270A, 270B (FIG. 10E) that direct the second fluid into the second swirl chamber 276. The second swirl chamber 276 is preferably aligned with the second spray opening 254 for spraying the second fluid from the distal end 250 of the second orifice cup 118. In one embodiment, four flutes 264A, 264B, 270A, and 270B have respective widths $W_2$ (FIG. 10H) of about 0.005 inches and respective heights $H_2$ of about 0.010 inches (FIG. 10E). In one embodiment, the second spray orifice 154 has a length $L_1$ of about 0.010 inches and an inner diameter $ID_2$ of about 0.010 inches. In one embodiment, the second swirl chamber 276 has a diameter $D_2$ of about 0.020-0.040 inches, and more preferably about 0.030 inches. In one embodiment, the diameter $D_1$ of the first swirl chamber (FIG. 9D) matches the diameter $D_2$ of the second swirl chamber 276.

In one embodiment, the second spray housing 116 (FIG. 3) has a structure and dimensions that are similar to the first spray housing 108 shown and described above in FIGS. 4A-4C. In one embodiment, the second orifice cup 118 (FIGS. 10A-10I) is assembled with the distal end of the second spray housing in a manner that is similar to that shown and described above in the embodiment of FIGS. 9A and 9B.

Figure 11:
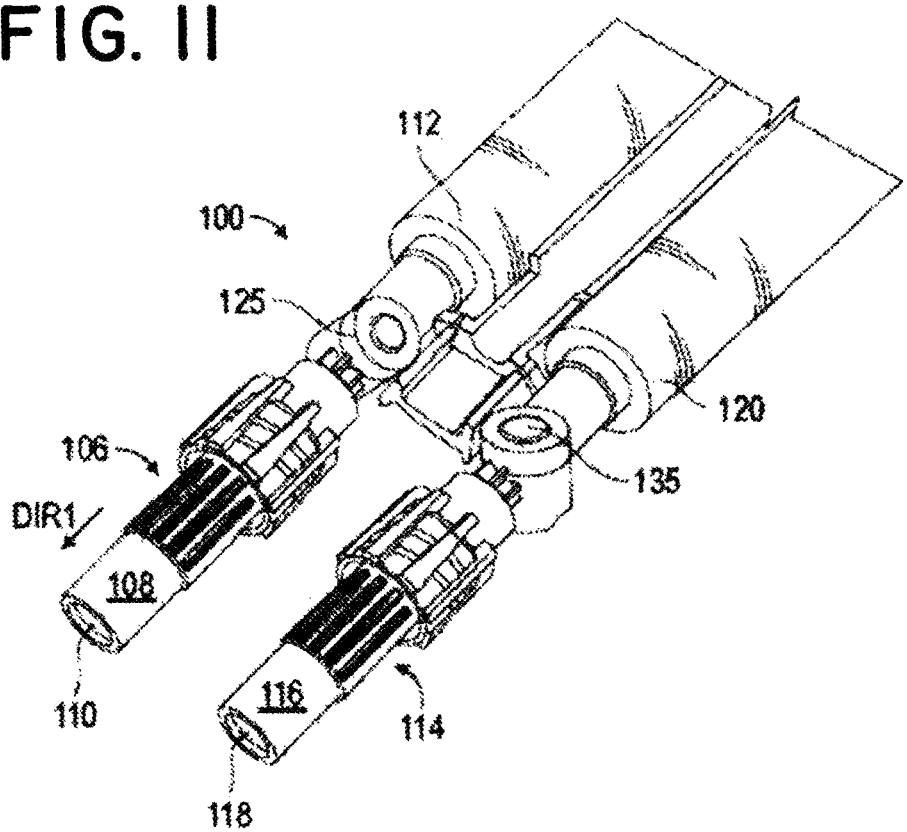
FIG. 11 is a perspective view of a distal end of a spray device used for spraying two fluids that react together, in accordance with one embodiment of the present patent application.

Referring to FIG. 11, in one embodiment, a spray device 100 for spraying two fluids that react together preferably includes a first spray tip 106 including a first spray housing 108 with a first orifice cup 110 and a second spray tip 114 including a second spray housing 116 with a second orifice cup 118. The first and second spray housings 108, 116 are desirably side-by-side and spaced from one another at the distal end of the spray device 100 so that a physical gap G is present between the side-by-side first and second spray housings 108, 116. In one embodiment, the proximal end of the first spray housing 108 is preferably in fluid communication with a first syringe 112 that contains a first fluid (e.g., Fibrinogen), and the proximal end of the second spray housing 116 is preferably in fluid communication with a second syringe 120 that contains a second fluid (e.g., Thrombin). In one embodiment, the first and second fluids preferably chemically interact with one another after being sprayed from the distal ends of the respective first and second spray housings 108, 116.

In one embodiment, the spray device 100 preferably includes a first one-way check valve 125 located between the first syringe 112 and the first spray housing 108, which enables the first fluid to flow in only one direction, namely, the distal direction designated DIR1 while preventing any part of the second fluid from backing up into or contacting the first spray tip, which would result in clogging of the first spray tip. Similarly, the spray device 100 preferably includes a second one-way check valve 135 located between the second syringe 120 and the second spray housing 116, which enables the second fluid to flow in only one direction, namely, the distal direction designated DIR1 while preventing any part of the first fluid from backing up into or contacting the second spray tip, which would result in clogging of the second spray tip.

In one embodiment, the first and second fluids in the respective first and second syringes 112, 120 are simultaneously forced into the proximal ends of the first and spray housings 108, 116 for spraying the first fluid from the distal end of the first spray housing 108 and the second fluid from the distal end of the second spray housing 116. After being sprayed from the respective first and second spray housings 108, 116, the first and second fluids desirably mix together in the air and/or on a surface for reacting with one another. The gap between the first and second spray housings ensures that the first and second fluids contact one another only after being sprayed from the distal ends of the first and second spray housings 108, 116, and prevents the two fluids with reacting with one another on the surfaces of the spray housings, which could clog the spray openings of the spray tips.

Figure 12:
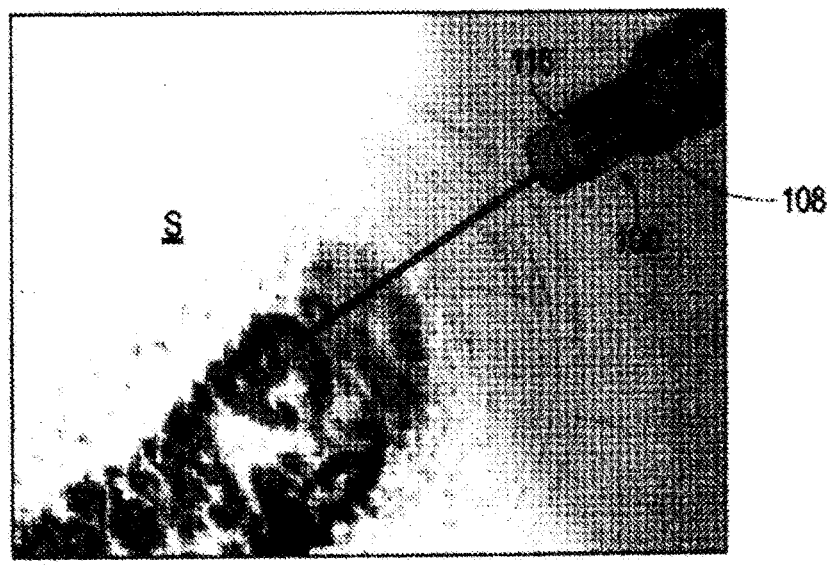
FIG. 12 illustrates the spray device of FIG. 11 while spraying first and second fluids onto a surface, in accordance with one embodiment of the present patent application.

Referring to FIGS. 11 and 12, in one embodiment, the plungers (not shown) within the first and second syringes 112, 120 may be depressed in the distal direction DIR1 toward the distal end of the spray device 100 for spraying the first and second fluids from the respective first and second spray housings 108, 116. The first and second fluids are preferably sprayed onto a surface S (FIG. 12), whereupon the first and second fluids mix together and react with one another. The gap or spacing between the side-by-side first and second spray housings 108, 116 preferably prevents the first and second fluids from contacting one another on the surfaces of the first and second spray housings 108, 116, thereby preventing clogging of the first and second spray openings associated with the respective first and second spray housings.

As used herein, the terminology "volumetric flow rate" means a volume of fluid that passes through a given cross-sectional area per unit time. The volumetric flow rate may be measured in liters per second (L/s), or in meters cubed per second (m³/s). The volumetric flow rate depends on the flow area A of the channel or fluid pathway that the fluid is moving through, and the velocity of the fluid. If the fluid is flowing through a rectangular fluid pathway, the flow area is A=H×W, wherein H is the height of the pathway and W is the width of the pathway. Volumetric flow rate is calculated using the equation Q=V/t, where Q is the volumetric flow rate, V is the volume of the fluid, and t is time.

The volumetric flow rate of a fluid may also be represented by the mathematical formula Q=Av, where A is the area of a conduit (e.g., the area defined by one or more flutes that make up a fluid flow path) through which the fluid flows, and v is the velocity of the fluid. Thus, if a fluid is flowing through a conduit at a constant volumetric flow rate (Q) and the cross-sectional area (A) of the conduit decreases in size, the velocity (v) of the fluid flowing through the conduit must increase in order to maintain the constant volumetric flow rate (Q).

Fluids are incompressible and maintain their volume as they flow through conduits (e.g., flutes). As used in the present patent application, this means that the volume of the fluid that flows into a first end of a conduit (e.g., the flutes 164, 170 shown in FIG. 8D; the flutes 264A, 264B, 270A, 270B shown in FIG. 10D) in a given amount of time must equal the volume of the fluid that flows out of the second end of the conduit in the same amount of time. Thus, the volumetric flow rate Q for an incompressible fluid, such as Fibrinogen, at any point along the length of a conduit (e.g., a flute) is the same as the volumetric flow rate at any other point along the length of the conduit, which is represented mathematically using the formula Q1=Q2.

Substituting the equation for volumetric flow rate, Q=Av, into the formula Q1=Q2, provides the equation $A_1v_1=A_2v_2$. The above equation is known as the equation of continuity for incompressible fluids. It dictates that if the area A of a section of a conduit decreases in size, then the speed v of the fluid at the section of the conduit having the decreased size must increase so that the product Av remains the same. In other words, fluid will speed up when it reaches a narrow section of a conduit and will slow down when it reaches a wider section of the conduit.

In the orifice cup embodiments disclosed in FIGS. 8A-8I and 10A-10I, the flutes are described as having square or rectangular dimensions, whereby the area A of the flute is calculated using the formula A=H×W, where H is the height of the flute and W is the width of the flute. In other embodiments, however, the flutes may have other cross-sectional shapes such as circular cross-sectional shapes, oval cross-sectional shapes, semi-circular cross-sectional shapes, etc. Well known mathematical formulas may be used for calculating the flow areas of flutes having the different cross-sectional shapes listed above. For example, for flutes having circular cross-sectional shapes, the area A of the flute is calculated using the formula $A=\pi r^2$, where π represents Pi (i.e., the number 22/7), and r is the radius of the flute.

Referring to FIGS. 8A-8I, in one embodiment, the volumetric flow rate of a fluid passing through the first orifice cup 110 is calculated using the cross-sectional areas (i.e., $A=H_1 \times W_1$) of the flutes at the inner ends 168, 174 of the respective first and second flutes 164, 170. Referring to FIGS. 10A-10I, in one embodiment, the volumetric flow rate of a fluid passing through the second orifice cup 118 is calculated using the cross-sectional areas (i.e., $A=H_2 \times W_2$) of the flutes at the inner ends 268A, 268B, 274A, 274B of the respective flutes 264A, 264B, 270A, and 270B.

In one embodiment, the spray devices disclosed in the present patent application may be used for atomizing first and second fluids that are sprayed from respective first and second spray housings. As used herein, the term atomizing means separating a fluid or liquid into fine liquid particles and/or small liquid droplets.

Atomization of a fluid results from differences in velocity between the fluid and the air. Using similar spraying components, it is easier to atomize a lower viscosity fluid than a higher viscosity fluid. For example, it is easier to atomize Thrombin because it comprises a low viscosity fluid. In contrast, Fibrinogen is significantly more viscous than Thrombin, which makes atomization of Fibrinogen more difficult. Thus, if an identical spray device is first used to atomize Thrombin, and is later used to atomize Fibrinogen, the lower viscosity Thrombin spray would have a broader spray pattern with finer liquid particles, while the higher viscosity Fibrinogen spray would have a narrower spray pattern with larger liquid particles.

More energy is required to atomize a higher viscosity fluid, such as Fibrinogen, than a lower viscosity fluid, such as Thrombin. In one embodiment, in order to account for the viscosity differences and effectively atomize both a higher viscosity fluid and a lower viscosity fluid, the more viscous fluid (e.g., Fibrinogen) is passed through a first fluid pathway with a smaller flow area A, while the less viscous fluid (e.g., Thrombin) is passed through a second fluid pathway having a larger flow area A. In one embodiment, when both fluids are directed into the respective first and second fluid pathways at the same volumetric flow rate, the more viscous fluid (flowing through a first fluid pathway defining a smaller flow area) will have a greater velocity as it directed into a first swirl chamber, and the less viscous fluid (flowing through a second fluid pathway having a larger flow area) will have a relatively lower velocity as it is introduced into the second swirl chamber. Thus, because it is introduced into the first swirl chamber at a greater velocity, the more viscous fluid will spin more rapidly within the first swirl chamber than the less viscous fluid will spin within the second swirl chamber.

In one embodiment, an increase in the amount of energy applied to a fluid may be provided by increasing the pressure that is applied to a syringe that contains the fluid.

To date, prior art designs for spray devices have focused on minimizing the lengths of fluid pathways to increase the velocity of fluids. The present patent application discloses a spray device that provides an improved, novel way for atomizing higher viscosity fluids, such as Fibrinogen, which includes changing the fluid pathway, and more specifically the geometry or flow area A of fluid pathways that are provided on orifice cups having spray openings (e.g., the orifice cups shown and described in FIGS. 8A-8I and 10A-10I).

Referring to FIGS. 8A-8I and 9A-9B, in one embodiment, the first spray housing 108 preferably includes the first orifice cup 110 having the first fluid pathway 162 for the first, higher viscosity fluid (e.g., Fibrinogen). The first fluid pathway defined by the first orifice cup 110 is designed to effectively atomize the more viscous fluid (e.g., Fibrinogen). In one embodiment, the inner face 160 of the first orifice cup 110 has the first fluid pathway 162 formed therein. In one embodiment, when the inner face 160 of the first orifice cup 110 is pressed against the distal end face 144 of the insert 134 (FIG. 9A), the first fluid pathway includes the two flutes 164, 170 that extend inwardly to the first swirl chamber 176. Each of the two flutes 164 and 170 preferably has a width of about 0.005 inches and a height of about 0.005 inches. Thus, the flow area A defined by the first fluid pathway 162 is preferably 0.00005 square inches (0.005 inches×0.005 inches×2 swirl flutes=0.00005 square inches).

Referring to FIGS. 9A-9B and 10A-10I, in one embodiment, the second spray housing 116 preferably includes the second orifice cup 118 having the second fluid pathway 262 for the second, less viscous fluid (e.g., Thrombin). The second fluid pathway defined by the second orifice cup 118 is designed to effectively atomize the less viscous fluid (e.g., Thrombin). In one embodiment, the inner face 260 of the second orifice cup 118 has the second fluid pathway 262 formed therein. In one embodiment, when the inner face 260 of the second orifice cup 118 is pressed against the distal end face of the insert 134, the second fluid pathway includes the four flutes 264A, 264B, 270A, and 270B that extend inwardly to the second swirl chamber 276. Each of the flutes 264A, 264B, 270A, and 270B preferably has a width $W_2$ of about 0.006 inches and a height $H_2$ of about 0.010 inches. Thus, the flow area A defined by the second fluid pathway 262 is preferably 0.00024 square inches (0.006 inches× 0.010 inches×4 swirl flutes=0.00024 square inches).

Thus, in one embodiment of the present patent application, the flow area A defined by the first fluid pathway of the first orifice cup 110 (FIGS. 8A-8I) that is used for a more viscous fluid may be five times (5×) smaller than the flow area A defined by the second fluid pathway of the second orifice cup 118 (FIGS. 10A-10I) used for a less viscous fluid. As a result, if a first fluid having a volumetric flow rate is introduced into first orifice cup 110 (FIGS. 8A-8I) and a second fluid having the same volumetric flow rate (as the first fluid) is introduced into the second orifice cup 118 (FIGS. 10A-10I), the velocity of the first fluid flowing through the first fluid pathway of the first orifice cup, at the location where the first fluid is introduced into the first swirl chamber 176 (FIG. 8E-1), will be five times (5×) greater (i.e., faster) than the velocity of the second fluid flowing through the second fluid pathway of the second orifice cup, at the location where the second fluid is introduced into the second swirl chamber 276 (FIG. 10E-1). The greater velocity that is applied to the first fluid (e.g., Fibrinogen) will spin the first fluid at a greater rate within the first swirl chamber (relative to the spin rate within the second swirl chamber) for applying greater energy to the first fluid, which will enable effective atomization of more viscous fluid (e.g., Fibrinogen).

Figure 13A:
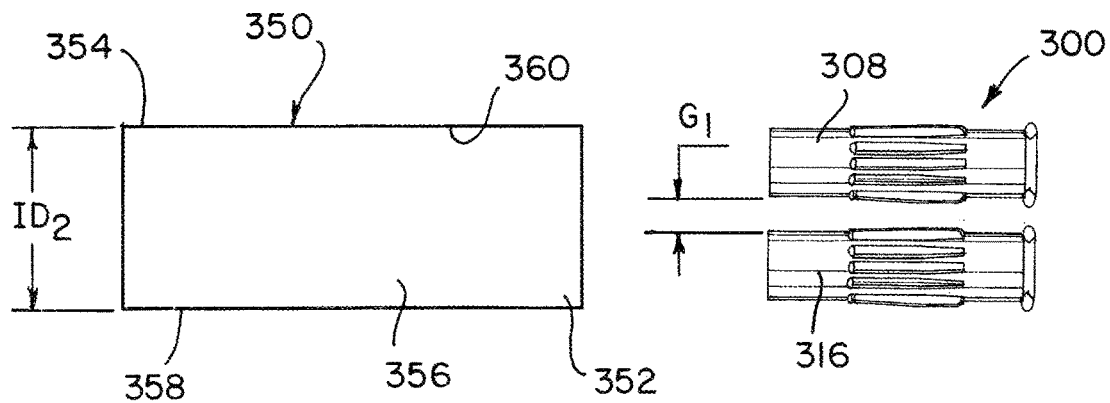
FIG. 13A is a first step of a method of passing a spray device having first and second spray housings through a cannula, in accordance with one embodiment of the present patent application.

Referring to FIG. 13A, in one embodiment, a spray device 300 may be passed through a small tube such as a cannula 350 for reaching a surgical site located inside a patient. In one embodiment, the spray device 300 preferably includes a first spray tip with a first spray housing 308 containing a first orifice cup and a second spray tip with a second spray housing 316 containing a second orifice cup. Although not shown in FIGS. 13A-13C in order to simplify the presentation of the spray device, the spray device 300 may include one or more of the structural components shown and described in the present patent application (e.g., the spray device shown in FIG. 3).

In one embodiment, the cannula 350 includes a proximal opening at a proximal end 352 thereof and a distal opening at a distal end 354 thereof. The cannula 350 preferably defines an elongated conduit 356 that extends from the proximal end 352 to the distal end 354 thereof. In one embodiment, the cannula has an outer wall 358 having an inner surface 360 that defines an inner diameter $ID_2$ of the cannula of about 5 mm-12 mm.

In one embodiment, the first and second spray housings 308, 316 of the spray device 300 are movable between a contracted configuration, in which the first and second spray housings are closer together, for passing through the inner diameter of the cannula 350, and an extended configuration, in which the first and second spray housings are further apart from one another than when in the contracted configuration, for spraying first and second fluids at a surgical site. In FIG. 13A, the first and second spray housings 308, 316 are in the contracted configuration with a gap $G_1$ defining the spacing between the side-by-side first and second spray housings.

Figure 13B:
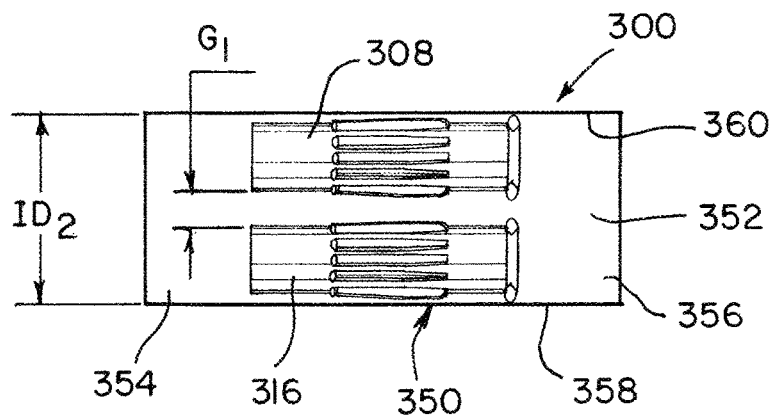
FIG. 13B is a second step of a method of passing the spray device of FIG. 13A through a cannula, in accordance with one embodiment of the present patent application.

Referring to FIG. 13B, in one embodiment, with the first and second spray housings 308, 316 in the contracted configuration, the spray device 300 may be passed distally through the elongated conduit 356 of the cannula 350 for advancing the spray device to a surgical site. The spray device 300 is preferably advanced distally through the elongated conduit 356 of the cannula 300 for passing the first and second spray housings through the distal opening at the distal end 354 of the cannula 350. As the first and second spray housings 308, 316 are passed distally through the elongated conduit 356 of the cannula 350, the first and second spray housings are maintained in the contracted configuration so that the spray housings may readily pass through the inner diameter $ID_2$ defined by the inner surface 360 of the outer wall 358 of the cannula 350.

Figure 13C:
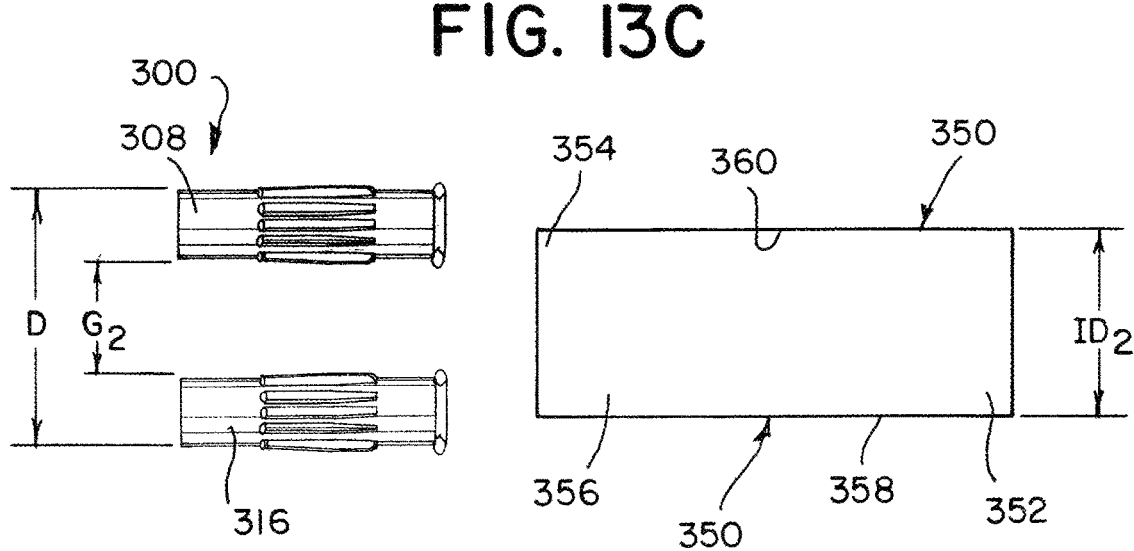
FIG. 13C is a third step of a method of passing the spray device of FIGS. 13A and 13B through a cannula, in accordance with one embodiment of the present patent application.

Referring to FIG. 13C, after the first and second spray housings 308, 316 of the spray device have been advanced through the distal opening at the distal end 354 of the cannula 350, the first and second spray housings may be moved into an extended configuration defining a gap $G_2$ that is greater than the gap $G_1$ when the first and second spray housings 308, 316 are in the contracted configuration (FIG. 13A). Moreover, the combined distance D between the outer sides of the first and second spray housings 308, 316 is greater than the inner diameter $ID_2$ defined by the inner surface 360 of the outer wall 358 of the cannula 350. As a result, the spacing between the side-by-side first and second spray housings 308, 316 may be increased after passing the spray device 300 through the cannula 350 to insure appropriate spacing between the spray orifices located at the distal ends of the respective first and second spray housings so that the first and second fluids sprayed through the spray orifices do not mix with one another on the surfaces of the respective first and second spray housings 308, 316.

At the conclusion of a surgical procedure, the spacing between the first and second spray housings 308, 316 may be transformed back to the contracted configuration shown in FIGS. 13A and 13B for removing the spray device 308 from the surgical site and withdrawing the spray device through the inner diameter $ID_2$ of the cannula 350

Figure 14:
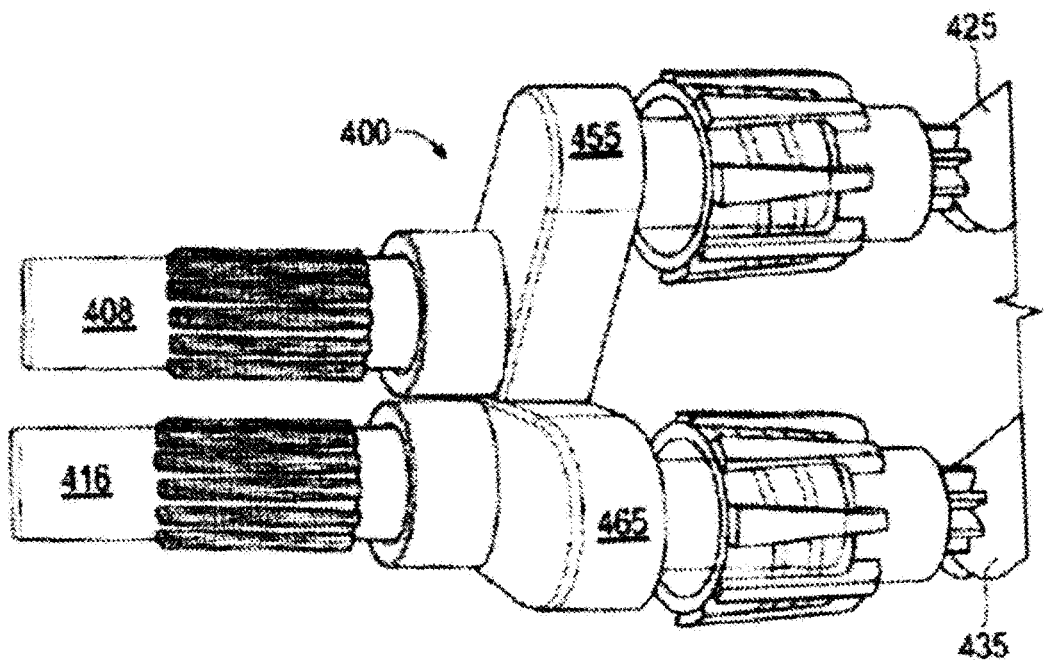
FIG. 14 is a side view of a spray device used for spraying first and second fluids that react together, in accordance with one embodiment of the present patent application.

Referring to FIG. 14, in one embodiment, a spray device 400 for spraying first and second fluids that react together may include a first spray housing 408 having a proximal end coupled with a first manifold 452, which directs a first fluid into the first spray housing 408 for spraying the first fluid from the distal end of the first spray housing. In one embodiment, the spray device preferably includes a first one-way check valve 425 that is located between the first manifold 455 and a first syringe containing a first fluid to ensure that the first fluid may only flow in a distal direction DIR1, and may not reverse direction and flow proximally back into the first syringe containing the first fluid.

In one embodiment, the spray device 400 desirably includes a second spray housing 416 having a proximal end coupled with a second manifold 465 that is configured for directing a second fluid into the second spray housing 416. In one embodiment, the spray device preferably includes a second one-way check valve 435 that is located between the second manifold 465 and a second syringe containing a second fluid to ensure that the second fluid may flow only in a distal direction DIR1, and may not reverse direction and flow proximally back into the second syringe containing the second fluid.

Figure 15:
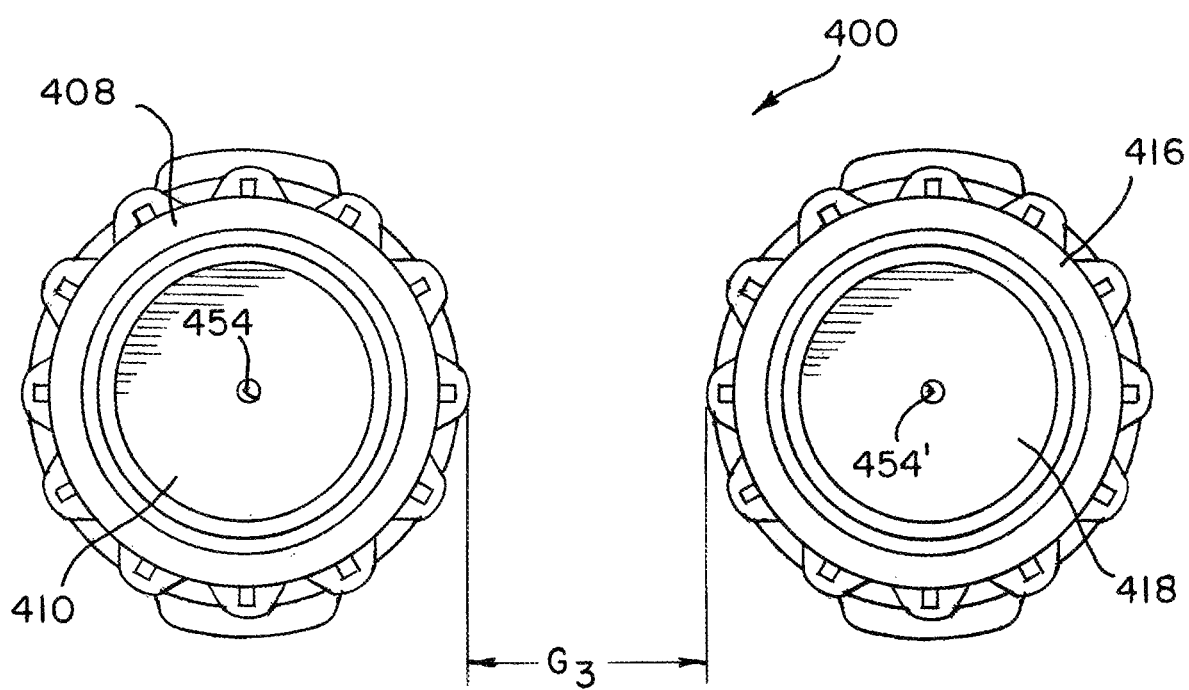
FIG. 15 is a distal end view of two spray housings, which are side-by-side at a distal end of a spray device, in accordance with one embodiment of the present patent application.

Referring to FIG. 15, in one embodiment, the distal end of the spray device 400 preferably includes the first and second spray housings 408, 416 that are spaced from one another. In one embodiment, the spray device 400 includes a first orifice cup 410 with a first spray opening 454 secured to a distal end of the first spray housing 408. In one embodiment, a first fluid is preferably sprayed from the first spray opening 454 of the first orifice cup 410. In one embodiment, the spray device 400 preferably includes a second orifice cup 418 with a second spray opening 454' secured to a distal end of the second spray housing 416. In one embodiment, a second fluid is preferably sprayed from the second spray orifice 454' of the second orifice cup 418. In one embodiment, the first and second fluids react with one another downstream from the first and second spray housings 408, 416. In one embodiment, the first and second fluids preferably contact one another for the first time only after being sprayed from the distal ends of the respective first and second spray housings 408, 416 of the spray device 400.

In one embodiment, the size of the gap G that is between the side-by-side first and second spray housings 408, 416 may be changed for passing the distal end of the spray device through a smaller cannula or tube. In one embodiment, the spray device 400 may be transformed from a contracted configuration (i.e., a smaller gap) to an extended configuration (i.e., a larger gap) for changing the size of the gap G between the first and second spray housings 408, 416.

During medical procedures, when positioning a spray device at a surgical site, a surgeon may inadvertently advance and/or depress the plungers of syringes, which may prematurely dispense the tissue sealant fluids, resulting in premature tip clogging and/or variation in spray performance.

In order to avoid inadvertent and/or premature dispensing of the tissue sealant fluids, in one embodiment, a spray device may include one or more pressure control valves that preferably eliminate inadvertent plunger advancement and/or reduce variation in spray performance by requiring a preset minimum pressure in order to open the pressure control valve and permit flow of the tissue sealant fluids. In one embodiment, a spray device may include a first pressure control valve located between a first syringe for a first fluid and a first spray tip, and a second pressure control valve located between a second syringe for a second fluid and a second spray tip. In one embodiment, a spray device may include a series of two pressure control valves located between a syringe for a fluid and a spray tip, whereby the fluid passes through a first pressure control valve and then a second pressure control valve before reaching the spray tip.

In one embodiment, the first and second pressure control valves may have a similar design. In one embodiment, a pressure control valve may have a pressure control valve cap, a pressure control valve diaphragm including a flexible membrane, and a pressure control valve body that has a fluid inlet and a fluid outlet.

In one embodiment, the pressure control valve cap preferably applies pressure on the top of pressure control valve diaphragm and the base of the pressure control valve body for keeping the pressure control valve diaphragm in contact with a raised mound of body. In one embodiment, when dispensing a fluid, the fluid pressure builds up inside the pressure control valve body until the fluid pressure elastically deforms the flexible membrane of the pressure control valve diaphragm for allowing fluid to flow through the pressure control valve body. The pressure control valve preferably prevents accidental expression of the fluid, and eliminates poor spray due to slow expression of the fluid.

Figure 16:
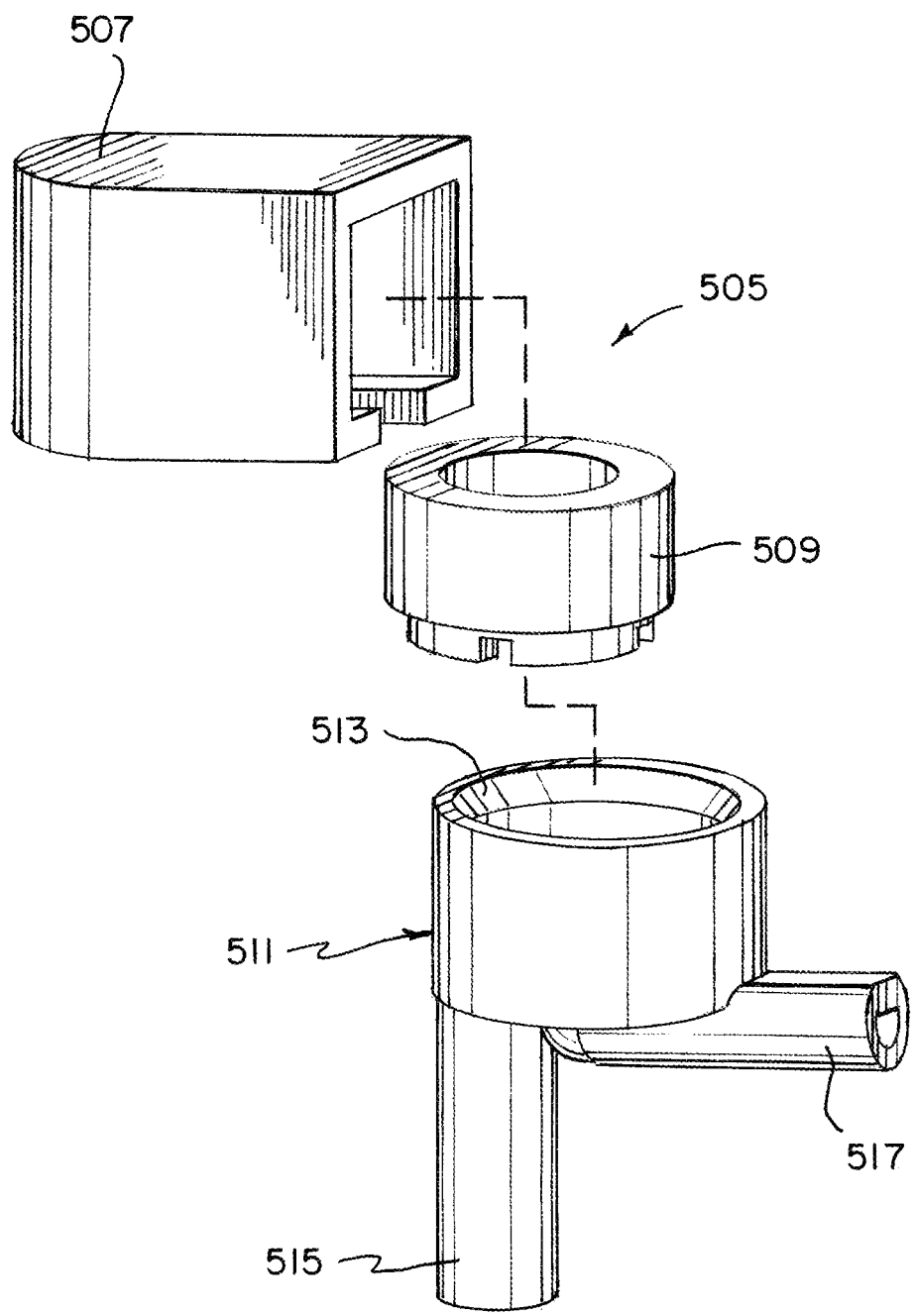
FIG. 16 is an exploded view of a pressure control valve of a spray device, the pressure control valve including a cap, a diaphragm, and a base, in accordance with one embodiment of the present patent application.

Referring to FIG. 16, in one embodiment, a spray device may include a pressure control valve 505 incorporated therein for ensuring that a predetermined pressure level for a fluid is attained before the fluid is able to pass through the pressure control valve and flow downstream into one of the spray tips. In one embodiment, the pressure control valve 505 preferably includes a pressure control valve cap 507, a pressure control valve diaphragm 509 and a pressure control valve base 511 that are assembled together to form the pressure control valve.

In one embodiment, the pressure control valve base 511 preferably has a central chamber 513 adapted to receive the pressure control valve diaphragm 509, a fluid inlet 515 that enables a fluid to enter into the central chamber 513, and a fluid outlet 517 that enables the fluid to flow out of the central chamber 513 of the pressure control valve 505.

Figure 17A:
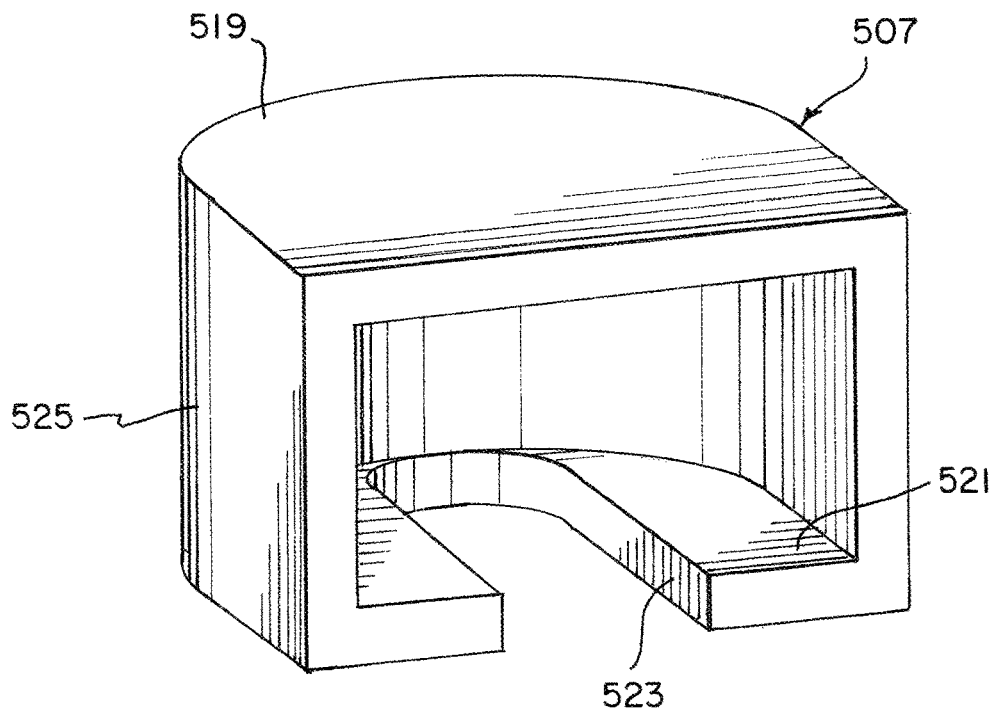
FIG. 17A is a perspective view of an open end of the pressure control valve cap shown in FIG. 16.
Figure 17B:
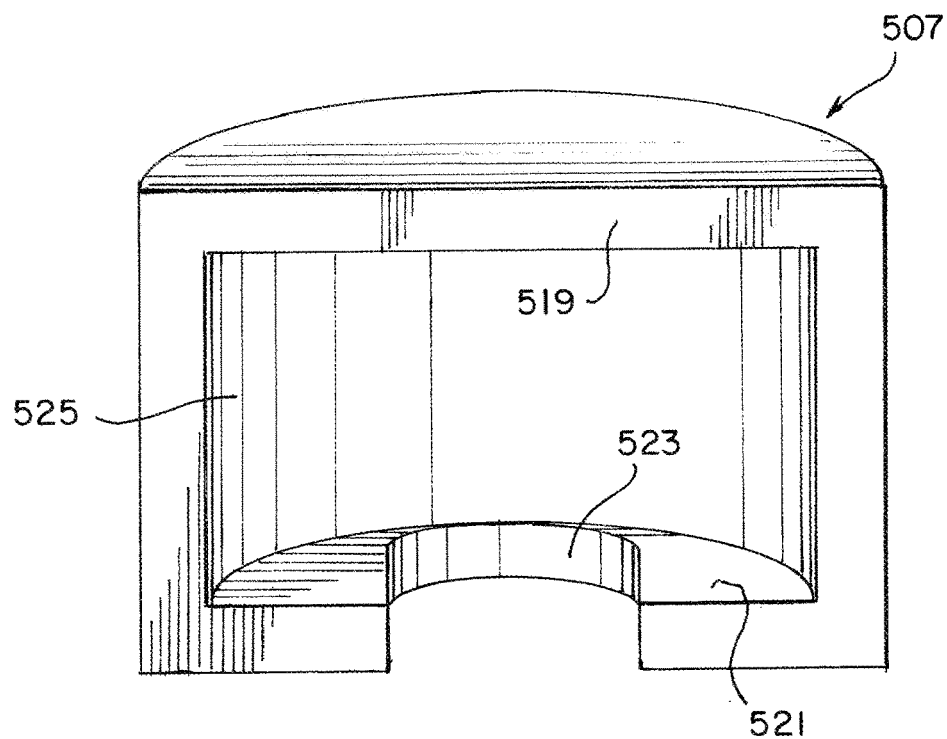
FIG. 17B is a front elevation view of the open end of the pressure control valve cap shown in FIGS. 16 and 17A.

Referring to FIGS. 17A and 17B, in one embodiment, the pressure control valve cap 507 preferably includes a ceiling 519, a floor 521 with a cutout 523 formed therein, and an annular wall 525 that extends between the ceiling 519 and the floor 521 for defining a closed end of the pressure control valve cap 507. The pressure control valve cap 507 desirably has an open end 527 that is located at the open end of the cutout 523 formed in the floor 521 thereof.

Figure 18A:
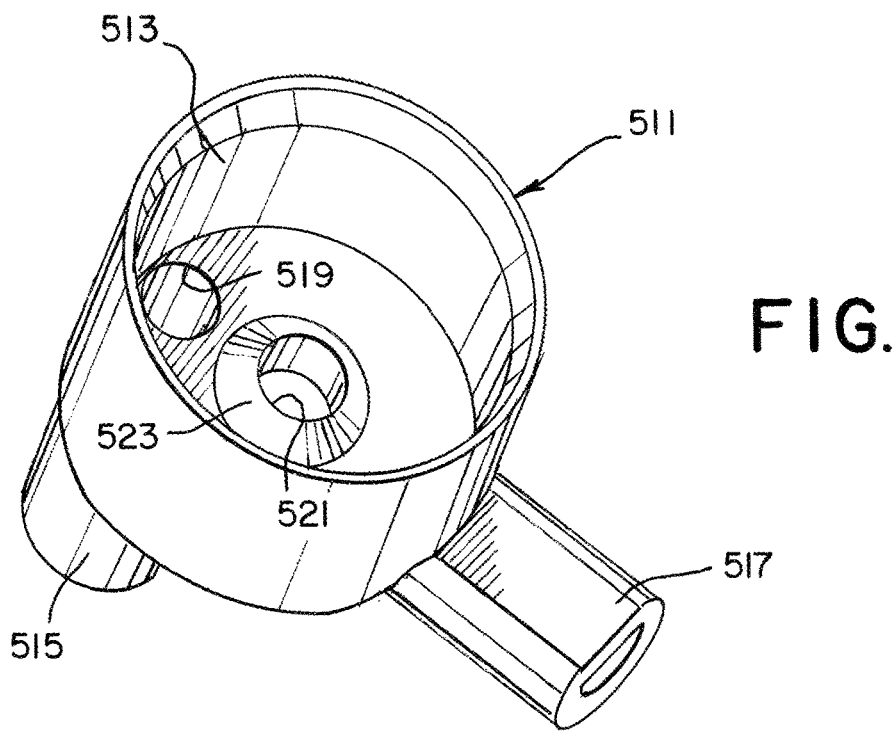
FIG. 18A is a perspective view of a top side of the pressure control valve base shown in FIG. 16.
Figure 18B:
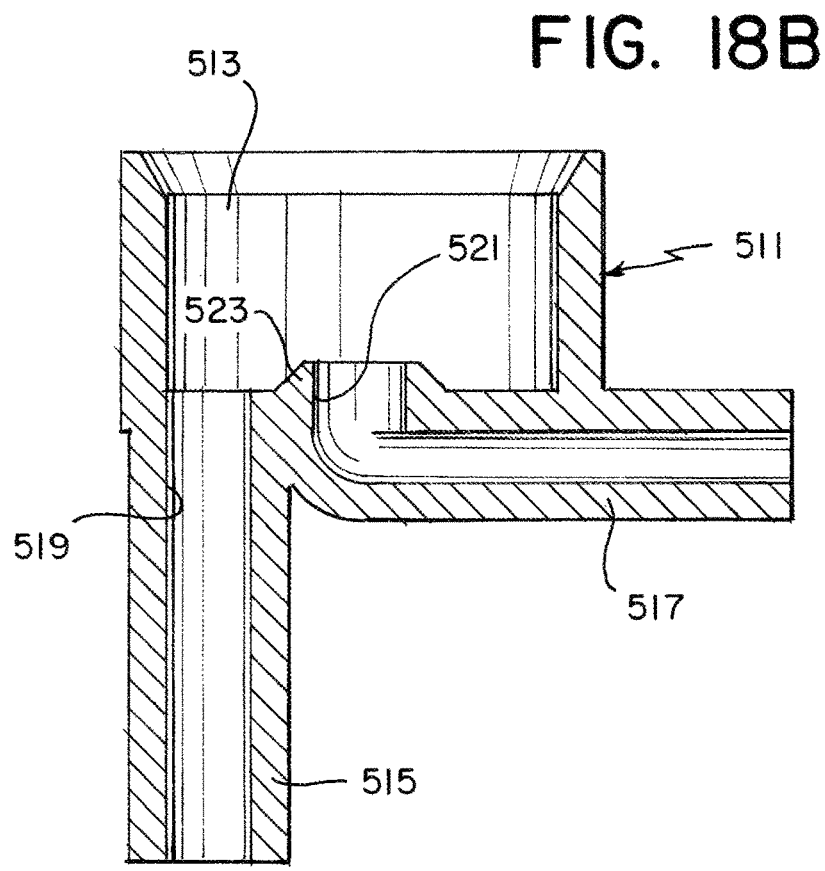
FIG. 18B is a cross-sectional view of the pressure control valve base shown in FIGS. 16 and 18A.

Referring to FIGS. 18A and 18B, in one embodiment, the pressure control valve base 511 preferably includes the central chamber 513 that is located between the inlet 515 and the outlet 517. In one embodiment, the upper end of the fluid inlet 515 defines a first opening 519 that enables a fluid to flow into the central chamber 513 of the pressure control valve base 511. The pressure control valve base also preferably includes a second opening 521 that enables the fluid disposed within the central chamber 513 to flow into the proximal end of the fluid outlet 517. The pressure control valve base 511 desirably includes a raised mound 523 that surrounds the second opening 521 located within the central chamber 513.

Referring to FIG. 18B, in one embodiment, a fluid directed into the fluid inlet 515 desirably flows through the first opening 519 and into the central chamber 513. The fluid may then pass through the second opening 521 at the proximal end of the fluid outlet 517 for flowing out of the pressure control valve base 511. As will be described in more detail herein, until the fluid reaches a predetermined pressure level, the mound 523 preferably seats and/or forms a seal with an underside of a flexible wall of the pressure control valve diaphragm 509 (FIG. 16) for preventing fluid from flowing through the second opening 521 and into the fluid outlet 517. In one embodiment, when the fluid has reached the predetermined pressure level for the fluid, the fluid forces the flexible wall of the pressure control valve diaphragm away from the second opening 521 so that the fluid in the central chamber 513 may flow into the second opening 521. In one embodiment, the pressure control valve 511 preferably functions like an on/off switch that will only turn on or open when the pressure level of the fluid within the pressure control valve 505 (FIG. 16) has reached and/or surpassed the predetermined pressure level for the fluid. If the fluid pressure is below the predetermined pressure level, the pressure control valve is closed and no fluid flows through the pressure control valve. If the fluid pressure is above the predetermined pressure level, the pressure control valve is opened and the fluid flows through the pressure control valve 511 and downstream to the spray tip associated with the pressure control valve.

Figure 19:
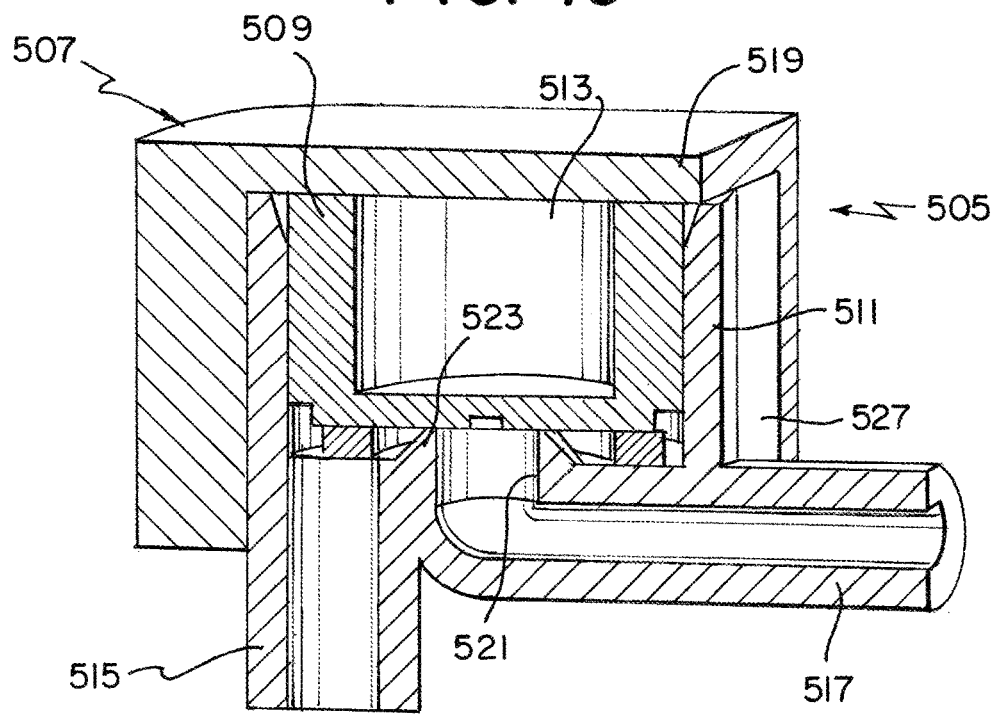
FIG. 19 is a cross-sectional view of a fully assembled pressure control valve including the pressure control valve cap, the pressure control valve diaphragm, and the pressure control valve base shown in FIG. 16, in accordance with one embodiment of the present patent application.

Referring to FIG. 19, in one embodiment, the pressure control valve 505 may be assembled together by positioning the pressure control valve diaphragm 509 inside the central chamber 513 of the pressure control valve base 511. The pressure control valve cap 507 is preferably juxtaposed with the pressure control valve base 511 so that the open end 527 of the pressure control valve cap 507 is aligned with the longitudinal axis of the fluid outlet 517 of the pressure control valve base. The cutout or slot 523 (FIG. 17A) of the pressure control valve cap 507 is preferably slid over the proximal end of the fluid outlet 517 of the pressure control valve base 511. The ceiling 519 of the pressure control valve cap 507 preferably engages the upper end of the pressure control valve diaphragm 509 for holding the pressure control valve diaphragm within the central chamber 513 of the pressure control valve base 511.

In FIG. 19, the underside of flexible wall the pressure control valve diaphragm normally engages the mound 523 surrounding the second opening 521 of the pressure control valve base 511 for closing the second opening 521 and preventing fluid from passing through the second opening. As noted above, the pressure control valve is normally in a closed position, and will only move into the open position when the pressure level of the fluid passing into the fluid inlet 515 of the pressure control valve base 511 exceeds the predetermined pressure level for the fluid. The exact fluid pressure level that is required to move the flexible wall of the pressure control diaphragm between the closed and opened positions may be designed into the pressure control valve diaphragm.

Figure 20:
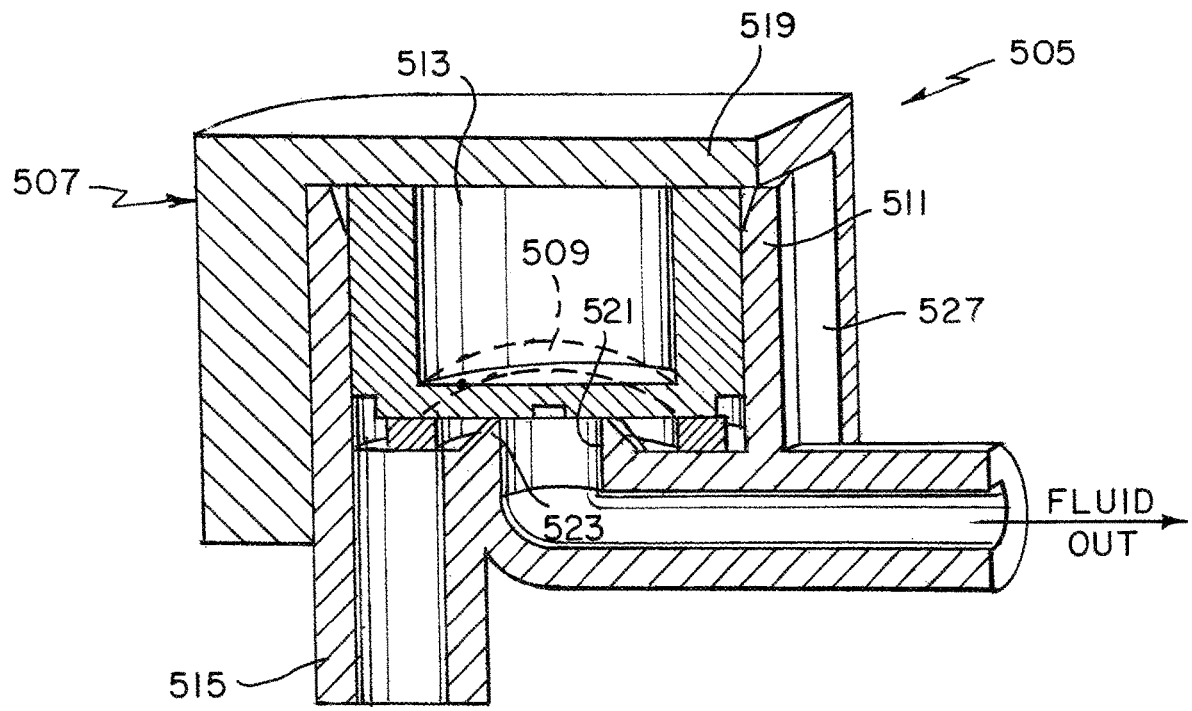
FIG. 20 shows the pressure control valve of FIG. 19 with a fluid flowing through the pressure control valve, in accordance with one embodiment of the present patent application.

Referring to FIG. 20, in one embodiment, once the pressure level of the fluid flowing into the inlet 515 exceeds the predetermined pressure level for the pressure control diaphragm 509, the pressure of the fluid will force the underside of the flexible wall of the pressure control valve diaphragm 509 away from its engagement with the mound 523 of the pressure control valve base 511. Once the flexible wall of the pressure control diaphragm is forced away from the second opening 521, the fluid is now free to pass through the second opening 521 of the pressure control valve base 511 and into the fluid outlet 517 for flowing out of the pressure control valve 505.

In one embodiment, a first pressure control valve for a first fluid may be positioned between a first syringe and a first spray tip, and a second pressure control valve for a second fluid may be positioned between a second syringe and a second spray tip. In one embodiment, the first pressure control valve may open at a first pressure level and the second pressure control valve may open at a second pressure level that is different than the first pressure level.

Figure 21:
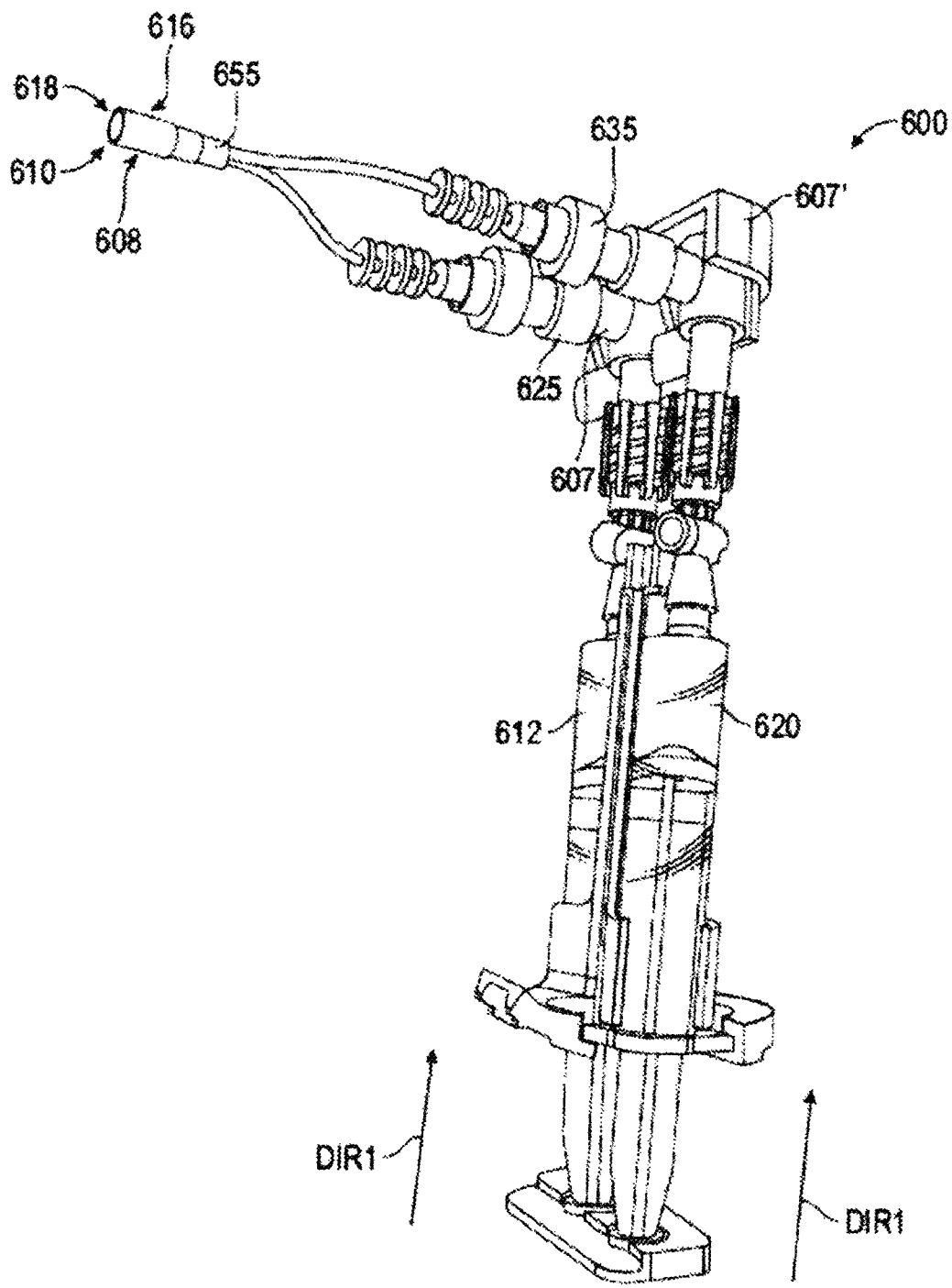
FIG. 21 is a perspective view of a spray device used for open procedures, in accordance with one embodiment of the present patent application.

FIG. 21 shows a spray device 600 used for spraying first and second fluids during an open surgical procedure. The spray device 600 preferably has a first side for a first fluid including a first syringe 612 adapted to hold the first fluid, a first pressure control valve 607, a first one way check valve 625, a manifold 655, and a first spray tip including a first spray housing 608 having a first spray orifice 610. The spray device 600 preferably has a second side for a second fluid including a second syringe 620 adapted to hold the second fluid, a second pressure control valve 607', a second one way check valve 635, the manifold 655, and a second spray tip including a second spray housing 616 having a second spray orifice 618. The spray tips are preferably side-by-side one another at the distal end of the spray device with the spray tips being spaced from one another by a gap that extends between the spray housings. The plungers of the first and second syringes may be simultaneously depressed in the direction DIR1 for spraying the first and second fluids from the distal ends of the respective first and second spray tips.

Figure 22:
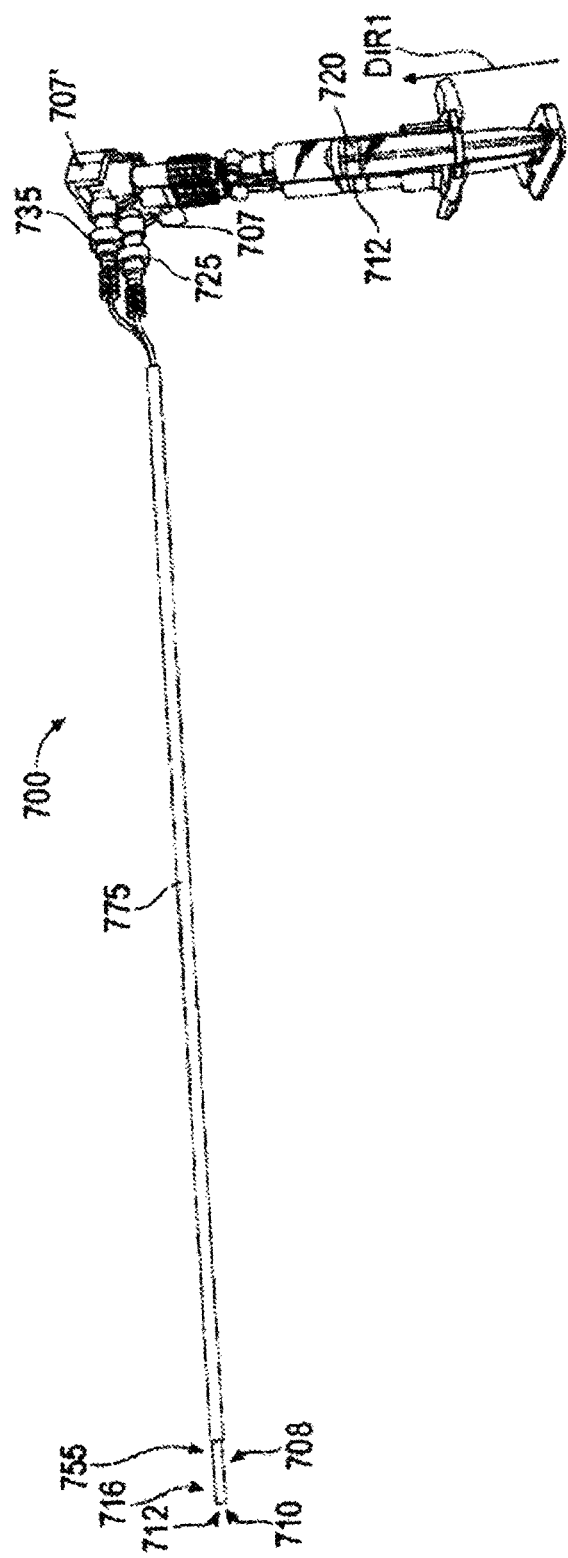
FIG. 22 is a perspective view of a spray device used for laparoscopic procedures, in accordance with one embodiment of the present patent application.

FIG. 22 shows a spray device 700 used for spraying first and second fluids at a surgical site during a closed or laparoscopic surgical procedure. The spray device 700 preferably has a first side for spraying a first fluid including a first syringe 712 adapted to hold the first fluid, a first pressure control valve 707, a first one way check valve 725, an elongated shaft 775 containing a first conduit for the first fluid, a manifold (not shown) and a first spray tip having a first spray housing 708 with a first spray orifice 710 secured to the distal end of the elongated shaft 775. The spray device 700 preferably has a second side for spraying a second fluid including a second syringe 720 adapted to hold a second fluid, a second pressure control valve 707', a second one way check valve 735, the elongated shaft 775 containing a second conduit for the second fluid, a manifold (not shown), and a spray tip including a second spray housing 716 with a second spray orifice 718 secured to the distal end of the elongated shaft 775. The spray tips are preferably side-by-side one another at the distal end of the elongated shaft 775 with the spray tips being spaced from one another by a gap that extends between the spray housings. The plungers of the first and second syringes 712, 720 may be simultaneously depressed in the direction DIR1 for spraying the first and second fluids from the distal ends of the respective first and second spray tips.

Figure 23:
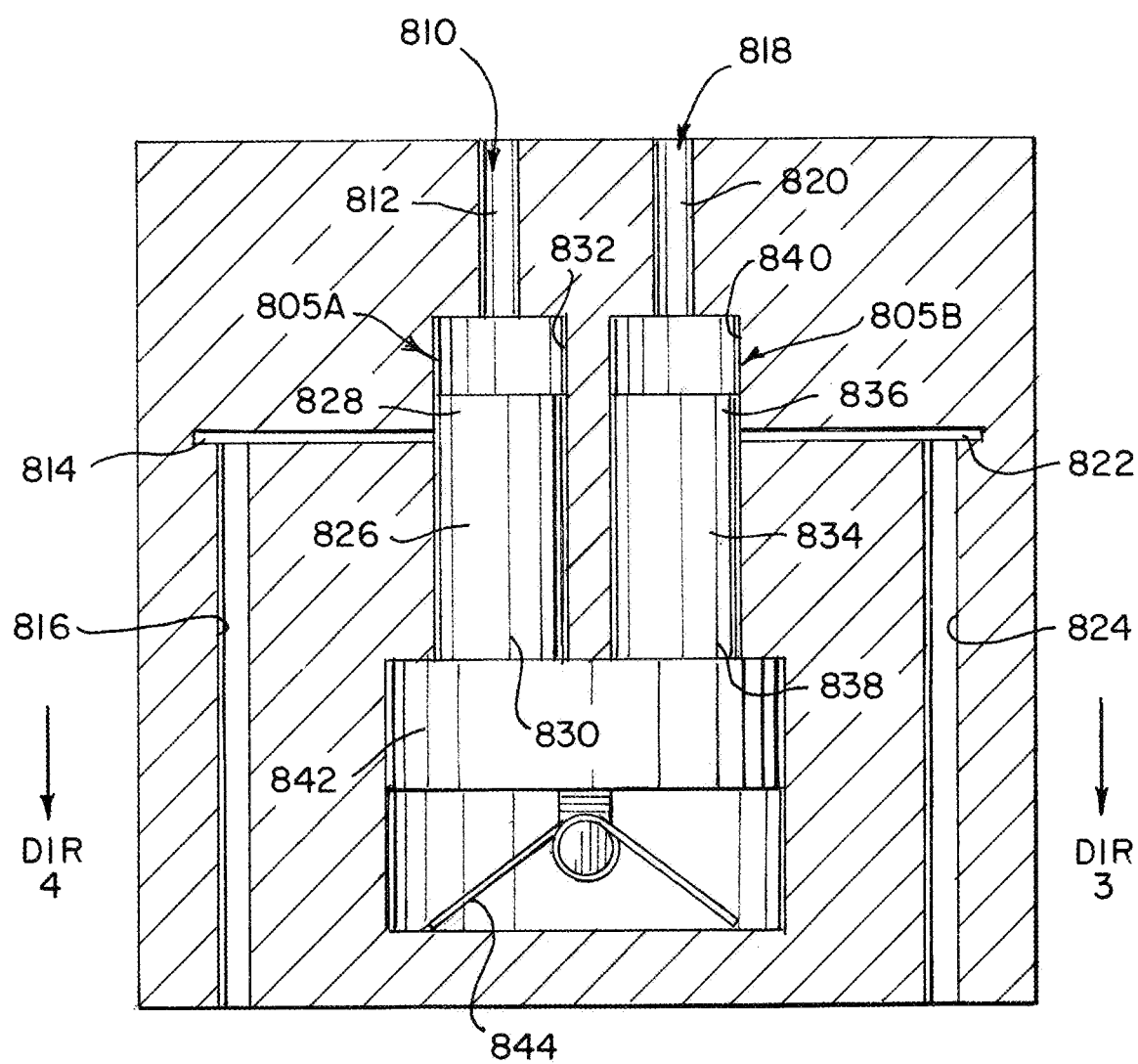
FIG. 23 shows two pressure control valves that are coupled together for moving together between open and closed positions for simultaneously opening and closing first and second fluid flow paths for dispensing first and second fluids, in accordance with one embodiment of the present patent application.

Referring to FIG. 23, in one embodiment, one or more of the spray devices disclosed herein may include two pressure control valves that are coupled together so that they move together between open and closed positions for simultaneously opening and closing first and second fluid flow paths for first and second fluids. In one embodiment, a first pressure control valve 805A is disposed within a first fluid pathway 810 for a first fluid. In one embodiment, the first fluid pathway desirably has an inlet section 812, an intermediate section 814, and an outlet section 816. In one embodiment, a second pressure control valve 805A is disposed within a second fluid pathway 818 for a second fluid. In one embodiment, the second fluid pathway 818 desirably has an inlet section 820, an intermediate section 822, and an outlet section 824.

In one embodiment, the first pressure control valve 805A includes a first piston 826 having an upper end 828 and a lower end 830. A first pressure chamber 832 is located between the inlet section 812 and the intermediate section 814 of the first fluid pathway 810.

In one embodiment, the second pressure control valve 805B includes a second piston 834 having an upper end 836 and a lower end 838. A second pressure chamber 840 is located between the inlet section 820 and the intermediate section 822 of the second fluid pathway 818.

In one embodiment, the lower ends 830, 838 of the respective first and second pistons 826, 834 are connected to a base plate 842, and a spring 844 is secured to an underside of the base plate 842 to provide resistance when the base plate 842 is moved in the direction DIR3 by fluid pressure building up in the first and second pressure chambers 832, 840.

In one embodiment, a first fluid is directed into the inlet section 812 of the first fluid pathway 810, whereupon the first fluid flows into the first pressure chamber 832 that is in fluid communication with the upper end 828 of the first piston 826. In one embodiment, a second fluid is directed into the inlet section 820 of the second fluid pathway 818, whereupon the second fluid flows into the second pressure chamber 840 that is in fluid communication with the upper end 836 of the second piston 834. As the pressure levels of the respective first and second fluids build up within the respective first and second pressure chambers 832, 840, the respective first and second pistons 826, 834 are forced in the direction DIR3 so that the upper ends 828, 836 of the first and second pistons are located below the intermediate sections 814, 822 of the respective first and second fluid pathways 810, 818. In one embodiment, once the upper ends of the first and second pistons 826, 834 are forced below the intermediate sections 814, 822 of the respective first and second fluid pathways, the first and second fluids may flow into the respective outlet sections 816, 824 of the first and second fluid pathways for being dispensed from the spray device.

In one embodiment, when the fluid pressure levels within the first and second pressure chambers 832, 840 falls below a predetermined pressure level, the spring 844 will move the base plate 842 in the direction DIR4 for closing the first and second pressure control valves 805A, 805B.

While the foregoing is directed to embodiments of the present invention, other and further embodiments of the invention may be devised without departing from the basic scope thereof, which is only limited by the scope of the claims that follow. For example, the present invention contemplates that any of the features shown in any of the embodiments described herein, or incorporated by reference herein, may be incorporated with any of the features shown in any of the other embodiments described herein, or incorporated by reference herein, and still fall within the scope of the present invention.

What is claimed is:

1. A spray device comprising:
   a first spray tip including a first fluid pathway that defines a first flow area, wherein the first fluid pathway comprises a first swirl chamber having an outer perimeter and flutes having inner ends that direct a first fluid into the outer perimeter of said first swirl chamber for rotating the first fluid in a circular pattern within said first swirl chamber;
   a second spray tip including a second fluid pathway that defines a second flow area that is larger than the first flow area of said first spray tip, wherein the second fluid pathway comprises a second swirl chamber having an outer perimeter and flutes having inner ends that direct a second fluid into the outer perimeter of said second swirl chamber for rotating the second fluid in a circular pattern within said second swirl chamber; and
   said first and second spray tips being side-by-side and spaced from one another at a distal end of said spray device.

2. The spray device as claimed in claim 1, wherein when the first fluid having a volumetric flow rate is introduced into said first spray tip and the second fluid having the same volumetric flow rate as the first fluid is introduced into said second spray tip, the first fluid will flow through the first fluid pathway of said first spray tip at a greater velocity than the second fluid will flow through the second fluid pathway of said second spray tip.

3. The spray device as claimed in claim 2, further comprising:
   said first spray tip including a first spray housing and a first orifice cup assembled with a distal end of said first spray housing, wherein said first orifice cup has a distal end wall with an inner face having the first fluid pathway formed therein; and
   said second spray tip including a second spray housing and a second orifice cup assembled with a distal end of said second spray housing, wherein said second orifice cup has a distal end wall with an inner face having the second fluid pathway formed therein.

4. The spray device as claimed in claim 3, wherein the first fluid pathway formed in the inner face of said distal end wall of said first orifice cup comprises said first swirl chamber.

5. The spray device as claimed in claim 4, wherein the second fluid pathway formed in the inner face of said distal end wall of said second orifice cup comprises said second swirl chamber.

6. The spray device as claimed in claim 5, wherein the inner ends of said flutes that direct the first fluid into the outer perimeter of said first swirl chamber define a first cross-sectional area and the inner ends of said flutes that direct the second fluid into the outer perimeter of said second swirl chamber define a second cross-sectional area that is different than the first cross-sectional area.

7. The spray device as claimed in claim 6, wherein the second cross-sectional area of said flutes of the second fluid pathway is at least twice as large as the first cross-sectional area of said flutes of the first fluid pathway.

8. The spray device as claimed in claim 7, wherein the second cross-sectional area of said flutes of the second fluid pathway is at least four times as large as the first cross-sectional area of said flutes of the first fluid pathway.

9. The pray device as claimed in claim 5, wherein said first swirl chamber has a first diameter and said second swirl chamber has a second diameter that is the same as the first diameter of said first swirl chamber.

10. The spray device as claimed in claim 4, wherein said first orifice cup comprises:
    a cylindrical outer wall having a proximal end with a proximal opening and a distal end that is closed by said distal end wall;
    a first spray opening that passes through said distal end wall and that is in fluid communication with said first swirl chamber.

11. The spray device as claimed in claim 10, wherein said first spray housing comprises:
    a first tubular body having a proximal end with a proximal opening, a distal end with a distal opening and an elongated conduit extending from the proximal opening to the distal opening of said first tubular body; and
    a first cylindrical insert disposed within said elongated conduit and located at the distal end of said first tubular body, said first cylindrical insert having a distal end wall at the distal end thereof, wherein said first orifice cup is assembled with said first cylindrical insert so that said distal end of said first cylindrical insert is disposed inside said cylindrical outer wall of said first orifice cup with the inner face of said distal end wall of said first orifice cup in contact with an outer surface of said distal end wall of said first cylindrical insert.

12. The spray device as claimed in claim 11, wherein said first swirl chamber and said flutes of said first orifice cup are disposed between the outer surface of said distal end wall of said first cylindrical insert and said distal end wall of said first orifice cup.

13. The spray device as claimed in claim 12, wherein said flutes of said first orifice cup comprise:
    a first flute having an outer end adjacent said cylindrical outer wall of said first orifice cup and an inner end located at the outer periphery of said first swirl chamber; and a second flute having an outer end adjacent said cylindrical outer wall of said first orifice cup and an inner end located at the outer periphery of said first swirl chamber, wherein said first and second flutes direct the first fluid into the outer perimeter of said first swirl chamber for rotating the first fluid within said first swirl chamber in the circular pattern.

14. The spray device as claimed in claim 4, wherein said second orifice cup comprises:
a cylindrical outer wall having a proximal end with a proximal opening and a distal end that is closed by said distal end wall; and
a second spray opening that passes through said distal end wall and that is in fluid communication with said second swirl chamber.

15. The spray device as claimed in claim 14, wherein said second spray housing comprises:
a second tubular body having a proximal end with a proximal opening, a distal end with a distal opening, and an elongated conduit extending from the proximal opening to the distal opening of said second tubular body; and
said second spray housing having a second cylindrical insert disposed within said elongated conduit and located at the distal end of said second tubular body, said second cylindrical insert having a distal end wall at the distal end thereof, wherein said second orifice cup is assembled with said second cylindrical insert so that said distal end of said second cylindrical insert is disposed inside said cylindrical outer wall of said second orifice cup with the inner face of said distal end wall of said second orifice cup in contact with an outer surface of said distal end wall of said second cylindrical insert.

16. The spray device as claimed in claim 15, wherein said second swirl chamber and said flutes of said second orifice cup are disposed between the outer surface of said distal end wall of said second cylindrical insert and said distal end wall of said second orifice cup.

17. The spray device as claimed in claim 16, wherein said flutes of said second orifice cup comprise:
a first flute having an outer end adjacent said cylindrical outer wall of said second orifice cup and an inner end located at the outer periphery of said second swirl chamber;
a second flute having an outer end adjacent said cylindrical outer wall of said second orifice cup and an inner end located at the outer periphery of said second swirl chamber;
a third flute having an outer end adjacent said cylindrical outer wall of said second orifice cup and an inner end located at the outer periphery of said second swirl chamber; and
a fourth flute having an outer end adjacent said cylindrical outer wall of said second orifice cup and an inner end located at the outer periphery of said second swirl chamber, wherein said first, second, third and fourth flutes direct the second fluid into the outer perimeter of said second swirl chamber for rotating the second fluid within said second swirl chamber in the circular pattern.

18. The spray device as claimed in claim 1, wherein the first fluid comprises Fibrinogen and the second fluid comprises Thrombin.

19. A spray device comprising:
a first syringe containing a higher viscosity fluid;
a second syringe containing a lower viscosity fluid that reacts with the higher viscosity fluid;
a first spray tip for spraying the higher viscosity fluid, wherein said first spray tip includes a first fluid pathway that defines a first flow area, wherein the first fluid pathway comprises a first swirl chamber having an outer perimeter and flutes having inner ends that direct a first fluid into the outer perimeter of said first swirl chamber for rotating the first fluid in a circular pattern within said first swirl chamber;
a second spray tip for spraying the lower viscosity fluid, wherein said second spray tip includes a second fluid pathway that defines a second flow area that is larger than the first flow area of said first spray tip, wherein the second fluid pathway comprises a second swirl chamber having an outer perimeter and flutes having inner ends that direct a second fluid into the outer perimeter of said second swirl chamber for rotating the second fluid in a circular pattern within said second swirl chamber; and
said first and second spray tips being side-by-side and spaced from one another at a distal end of said spray device.

20. The spray device as claimed in claim 19, wherein when the higher viscosity fluid is directed into said first spray tip at a volumetric flow rate and the lower viscosity fluid is directed into said second spray tip at the same volumetric flow rate that is used for the higher viscosity fluid, the higher viscosity fluid will flow through the first fluid pathway of said first spray tip at a greater velocity than the lower viscosity fluid will flow through the second fluid pathway of said second spray tip.

* * * * *